US012649761B2

(12) United States Patent
Zhong et al.

(10) Patent No.: US 12,649,761 B2
(45) Date of Patent: Jun. 9, 2026

(54) SYNTHESIS OF OLIGONUCLEOTIDES AND RELATED COMPOUNDS

(71) Applicant: JANSSEN BIOPHARMA, INC., San Francisco, CA (US)

(72) Inventors: Minghong Zhong, San Bruno, CA (US); Yi Jin, Carlsbad, CA (US); Dinesh Gala, Monroe, CA (US); Marija Prhavc, Encinitas, CA (US)

(73) Assignee: Janssen BioPharma, Inc., San Francisco, CA (US)

(*) Notice: Subject to any disclaimer, the term of this patent is extended or adjusted under 35 U.S.C. 154(b) by 819 days.

(21) Appl. No.: 17/916,064

(22) PCT Filed: Mar. 30, 2021

(86) PCT No.: PCT/IB2021/052595

§ 371 (c)(1),
(2) Date: Mar. 13, 2023

(87) PCT Pub. No.: WO2021/198883

PCT Pub. Date: Oct. 7, 2021

(65) Prior Publication Data

US 2024/0092821 A1 Mar. 21, 2024

Related U.S. Application Data

(60) Provisional application No. 63/003,067, filed on Mar. 31, 2020.

(51) Int. Cl.

*C07H 21/02* (2006.01)
*C07H 19/067* (2006.01)
*C07H 19/167* (2006.01)

(52) U.S. Cl.

CPC ........... *C07H 21/02* (2013.01); *C07H 19/067* (2013.01); *C07H 19/167* (2013.01)

(58) Field of Classification Search

CPC ........ C07H 1/00; C07H 21/02; C07H 19/067; C07H 19/167
See application file for complete search history.

(56) References Cited

U.S. PATENT DOCUMENTS

| | | | |
|---|---|---|---|
| 5,753,789 A | 5/1998 | Chu et al. | |
| 6,251,666 B1 | 6/2001 | Beigelman | |
| 6,268,490 B1 | 7/2001 | Imanishi | |
| 6,525,191 B1 | 2/2003 | Ramasamy et al. | |
| 6,770,748 B2 | 8/2004 | Imanishi | |
| 6,794,499 B2 | 9/2004 | Wengel et al. | |
| 6,972,330 B2 * | 12/2005 | Beigelman ............ | C07H 19/06 536/27.11 |
| 7,034,133 B2 | 4/2006 | Wengel et al. | |
| 7,053,207 B2 | 5/2006 | Wengel | |
| 7,084,125 B2 | 8/2006 | Wengel | |
| 7,217,805 B2 | 5/2007 | Imanishi et al. | |
| 7,314,923 B2 | 1/2008 | Kaneko et al. | |
| 7,569,575 B2 | 8/2009 | Sorensen et al. | |
| 7,696,345 B2 | 4/2010 | Allerson et al. | |
| 8,569,476 B2 | 10/2013 | Xi et al. | |
| 9,284,344 B2 | 3/2016 | Kim et al. | |
| 10,214,555 B2 | 2/2019 | Nonogawa et al. | |
| 2018/0282365 A1 | 10/2018 | Hirai et al. | |
| 2018/0291056 A1 | 10/2018 | Yamashita et al. | |

FOREIGN PATENT DOCUMENTS

| | | |
|---|---|---|
| CN | 101684136 A | 3/2010 |
| CN | 101868473 B | 12/2012 |
| EP | 0 540 742 | 5/1993 |
| JP | 2000247940 A | 9/2000 |
| WO | WO 1998/022489 | 5/1998 |
| WO | WO 1998/039352 | 9/1998 |
| WO | WO 1999/014226 | 3/1999 |
| WO | WO 2018/203574 A1 | 8/2018 |
| WO | WO 2021/198883 | 10/2021 |

OTHER PUBLICATIONS

Ellington, Current Protocols in Nucleic Acid Chemistry (2000) A.3C.1-A.3C.22. (Year: 2000).*
Osborn, Tetrahedron vol. 49, No. 14, pp. 2873-2884, 1993. (Year: 1993).*
Matsuno, Org. Lett., 2016, 18, 800-803. (Year: 2016).*
Lönnberg, "Synthesis of oligonucleotides on a soluble support," *Beilstein Journal of Organic Chemistry*, 13, pp. 1368-1387 (Jul. 2017).
Search Report dated Jul. 5, 2024 issued in Chinese Appln. 202180039628.0.
Zhao Xing-xu, *Transgenic Food Biotechnology and Safety*, Beijing: China Light Industry Press, Jul. 30, 2009.
Asseline et al., "Synthesis and physicochemical properties of oligonucleotides built with either α-L or β-L nucleotides units and covalently linked to an acridine derivative," *Nucleic Acids Research*, 19(15), pp. 4067-4074 (1991) (Oxford, England, UK).
Fujimori et al., "Enantio-DNA Recognizes Complementary RNA but Not Complementary DNA," *J. Amer. Chem. Soc.* 112(20), pp. 7436-7438 (1990) (Washington, DC, US).

(Continued)

*Primary Examiner* — Layla D Berry
(74) *Attorney, Agent, or Firm* — Arnold & Porter Kaye Scholer LLP

(57) ABSTRACT

Methods of synthesizing oligonucleotides via new intermediates on a cleavable support having an azidomethyl moiety are disclosed. The method comprises multiple reaction cycles, each of which comprises sequential coupling a nucleoside or oligonucleotide subunit on a cleavable support having an azidomethyl moiety and a nucleoside phosphoramidite or an oligonucleotide phosphoramidite, capping, oxidation/thiolation and deblocking; followed by orthogonal cleavage of the azidomethyl support while keeping all other protecting groups intact. The method can be used in combination with a support moiety for either solid phase or liquid phase oligo synthesis. The soluble support facilitates homogeneous reactions and efficient separations by simple precipitation. The methods also provide novel intermediates useful in the synthesis of oligonucleotide conjugates.

16 Claims, No Drawings

(56) References Cited

OTHER PUBLICATIONS

Garbesi et al., "L-DNAs as potential antimessenger oligonucleotides: a reassessment," *Nucleic Acids Research*, 21(18), pp. 4159-4165 (1993) (Oxford, England, UK).
Urata et al., "Spectroscopic characterization of heterochiral DNAs," *Nucleic Acids Symposium* Ser. No. 29, pp. 69-70 (1993) (Oxford, England, UK).
Molina, A. G., & Sanghvi, Y. S. (2019) *Liquid-phase oligonucleotide synthesis: Past, present, and future predictions. Current Protocols in Nucleic Acid Chemistry*, e82. doi: 10.1002/cpnc.82.
Pon, 1993, *Methods in Molecular Biology*, vol. 20: *Protocols for Oligonucleotides and Analogs*, Humana Press.
Shabarova, Z. and Bogdanov, A. Advanced Organic Chemistry of Nucleic Acids, VCH, New York, 1994.
Written Opinion of the International Searching Authority, dated Jun. 17, 2021, for related PCT/IB2021/052595 application.
V. A. Efimov et al: 11 Synthesis of RNA by 1-32 the Rapid Phosphotriester Method Using Azido-Based 2'-O-Protecting Groups 11, Nucleosides, Nucleotides & Nucleic Acids. vol. 28, No. 9, Sep. 17, 2009 (Sep. 17, 2009), pp. 846-865, XP055304200, US ISSN: 525-7770, DOI: 10.1080/15257770903170286 Scheme 2, p. 850, paragraph 2—p. 852, paragraph second last p. 855, paragraph first.
Kawanaka et al: "Synthesis of dinucleoside phosphates and their analogs by the boranophosphotriester method using azido-based protecting groups", Tetrahedron Letters, Elsevier, Amsterdam, NL, vol. 48, No. 11, Feb. 15, 2007 (Feb. 15, 2007), pp. 1973-1976, XP005890695, ISSN: 0040-4039, DOI: 10.1016/J.TETLET.2007.01.064 tables 1-2 p. 1976, paragraph first.
Wada Takeshi et al: "2-(Azidomethy])benzoyl as a new protecting group in nucleosides", Tetrahedron Letters, vol. 42, No. 6, 2009,—2009, pp. 1069-1072, XP085040739, ISSN: 0040-4039, DOI: 10.1016/S0040-4039(00)02183-3 Scheme 2.

* cited by examiner

SYNTHESIS OF OLIGONUCLEOTIDES AND RELATED COMPOUNDS

INCORPORATION BY REFERENCE TO ANY PRIORITY APPLICATIONS

Any and all applications for which a foreign or domestic priority claim is identified, for example, in the Application Dats Sheet or Request as filed with the present application, are hereby incorporated by reference under 37 CFR 1.57, and Rules 4.18 and 20.6, including U.S. Provisional Application No. 63/003,067, filed Mar. 31, 2020.

TECHNICAL FIELD

The present disclosure relates to synthesis of oligonucleotides via a cleavable support having an azidomethyl moiety. This disclosure also includes novel intermediates useful in the synthesis of oligonucleotides.

BACKGROUND

The following description of the background is provided simply as an aid in understanding the present disclosure and is not admitted to describe or constitute prior art to the present disclosure.

Oligonucleotides have been known to have important diagnostic and therapeutic applications. Currently, oligonucleotides are often produced using automated solid phase synthesis, and the development of an economic large-scale oligo synthesis has been an important issue for pharmaceutical industry. Some methods involve affixing the nucleotide to a support to facilitate the purification and elongation steps of the oligo synthesis process. However, removal of the support often results in loss of the important protecting groups on the oligos. In addition, many method for oligonucleotide synthesis often require large excess of expensive reagents and are difficult to scale up. Thus, there is a need to develop improved methods for synthesizing oligonucleotides, including improved supports that are stable during synthesis but can be removed under mild conditions.

SUMMARY

Provided herein are novel methods of synthesizing oligonucleotides via new intermediates on a cleavable support having an azidomethyl moiety are disclosed. In some embodiments, the method can comprise multiple reaction cycles (e.g., four-reaction cycles), each of which comprises sequential coupling a nucleoside or oligonucleotide subunit on a cleavable support having an azidomethyl moiety and a nucleoside phosphoramidite or an oligonucleotide phosphoramidite, capping, oxidation/thiolation and deblocking; followed by orthogonal cleavage of the azidomethyl support while keeping all other protecting groups intact. The method can be used in combination with a support moiety for either solid phase or liquid phase oligo synthesis. The soluble support facilitates homogeneous reactions and efficient separations by simple precipitation. The methods also provide novel intermediates useful in the synthesis of oligonucleotide conjugates.

Some embodiments relate to a compound represented by Formula (I) or (II):

(I)

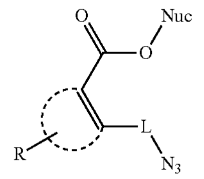

(II)

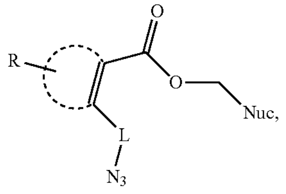

or a salt thereof, wherein

Nuc is a monomer nucleoside or nucleotide or an oligomer nucleoside or nucleotide, L is $C_{1-4}$ alkyl optionally substituted with one or more substituents selected from halogen, the dashed curve

represents a cyclic moiety; and

R is a support moiety optionally attached through one or more linkers to the cyclic moiety.

Some embodiments relate to a method of selectively conjugating an oligomer represented by Formula (I-A) or (II-A) having protected nucleobases, (I-A)

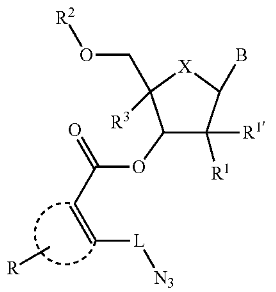

(II-A)

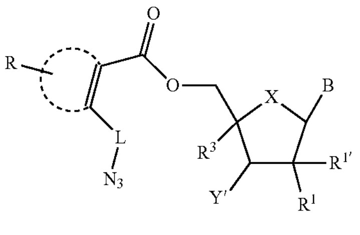

(a) reacting the oligomer represented by Formula (I-A) or (II-A) having protected nucleobases to form the following Formula (III):

(III)

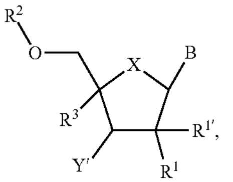

wherein B is a protected natural or unnatural nucleobase; Y' is OH, OR", or NHR"; R" is independently selected from H, aryl, a lower alkyl, and a $C_{1-4}$ haloalkyl; and (b) reacting the compound of Formula (III) at the 3' position to form a new covalent bond to a second compound.

Some embodiments relate to a compound of the following formula:

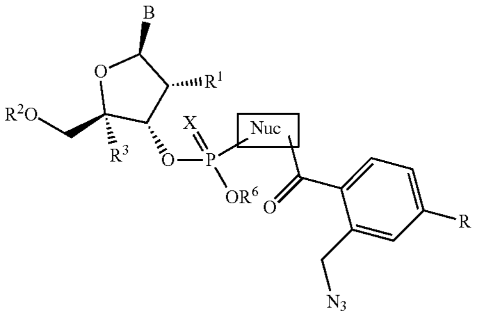

or

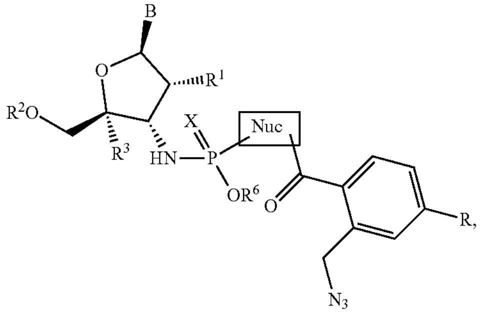

wherein

Nuc is an oligonucleotide subunit having 1-30 linked nucleosides;

B is a protected natural or unnatural nucleobase;

X is absent, O or S;

$R^1$ is selected from H, OPG, F, OR", and $O(CR'_2)_{1-2}OCR'_3$;

$R^2$ is selected from H and PG;

$R^3$ is selected from H, OPG, F, and OR", or $R^1$ and $R^3$ together form an optionally substituted 2-4 atom bridge;

R' is independently selected from H, F, aryl, a lower alkyl, and a lower haloalkyl;

R" is independently selected from H, aryl, a lower alkyl, and a lower haloalkyl;

PG is a protecting group;

$R^6$ is selected from a counterion, a methyl and a 2-cyanoethyl; and

R is a solid support or a soluble support moiety optionally attached through one or more linkers to the cyclic moiety.

DETAILED DESCRIPTION

Recent progress in various types of oligonucleotide therapeutics, such as antisense, aptamer, siRNA and miRNA, has led to growing demand for economical and/or large scale production. The methods described herein provide a viable approach for both solid-phase and liquid-phase oligonucleotide synthesis. The synthesis methods and compounds described herein can be used with soluble supports or solid supports. Particularly, when the method described herein are used with a soluble support, the resulting liquid phase synthesis approach can avoid the use of heterogenous reactions, reduce manufacture cost, and thus provide an efficient approach towards large scale production.

The methods described herein can be used to selectively prepare 3' and/or 5' substituted nucleotides and oligonucleotides. Another advantage of using the synthesis method described herein lies in that the protecting groups on nucleosides and phosphorous backbone can be left intact, and the protecting groups may be selectively cleaved under conditions different than the ones used for removal of the support. Selective modification at the 3' and/or 5' position of the nucleotides and selective removal of protecting groups on the nucleotides are described below in more details.

Synthetic Intermediates

The present disclosure provides methods of synthesizing oligonucleotides via novel intermediates.

Compounds of the present disclosure, which may be synthetic intermediates, include compounds represented by Formula (I) or (II):

(I)

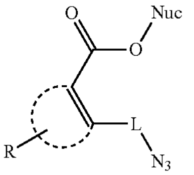

(II)

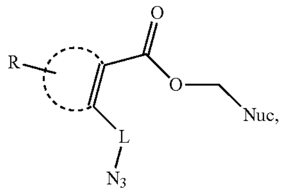

or a salt thereof, wherein

Nuc is a monomer nucleoside or nucleotide or an oligonucleotide,

L is $C_{1-4}$ alkyl optionally substituted with one or more substituents selected from halogen, the dashed curve

represents a cyclic moiety;

R is a support moiety optionally attached through one or more linkers to the cyclic moiety.

Compounds of the present disclosure, which may be synthetic intermediates, include compounds represented by Formula (I-A) or (II-A)_

(I-A)

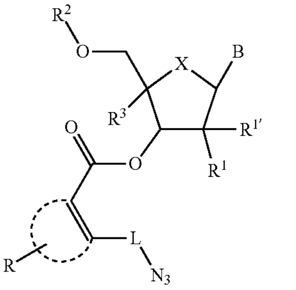

(II-A)

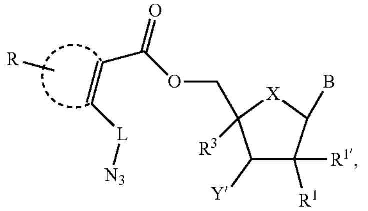

or a salt thereof, wherein

X is selected from O, S, NR" and $C(R')_2$;

Y is selected from OH, OR", OPG, NHPG, a ligand moiety, and NHR';

B is an optionally protected nucleobase;

$R^1$ and $R^{1'}$ are independently selected from H, OPG, F, OR", and $O(CR'_2)_{1-2}OCR'_3$;

$R^2$ is selected from H, a lower alkyl, a lower haloalkyl, PG, an optionally protected nucleotide, a prodrug moiety, a ligand moiety, and an optionally protected oligonucleotide;

$R^3$ is selected from H, OPG, F, and OR", or $R^1$ and $R^3$ together form an optionally substituted 2-4 atom bridge;

R' is independently selected from H, F, aryl, a lower alkyl, and a lower haloalkyl;

R" is independently selected from H, aryl, a lower alkyl, and a lower haloalkyl; and PG is a protecting group Compounds of the present disclosure, which may be synthetic intermediates, include compounds represented by Formula (I-1) or (II-1):

(I-1)

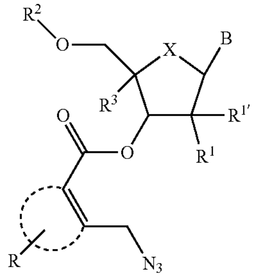

-continued (II-1)

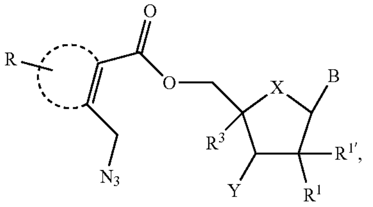

or a salt thereof, wherein

X is selected from O, S, NR" and $C(R')_2$;

Y is selected from OH, OR", OPG, NHPG, NHR" and an oligonucleotide;

B is an optionally protected natural or unnatural nucleobase;

$R^1$ and $R^{1'}$ are independently selected from H, OPG, F, OR", and $O(CR'_2)_{1-2}OCR'_3$;

$R^2$ is selected from H, a lower alkyl, a lower haloalkyl, PG, an optionally protected nucleotide, a prodrug moiety, and an optionally protected oligonucleotide;

$R^3$ is selected from H, OPG, F, and OR", or $R^1$ and $R^3$ together form an optionally substituted 2-4 atom bridge;

R' is independently selected from H, F, aryl, a lower alkyl, and a lower haloalkyl;

R" is independently selected from H, aryl, a lower alkyl, and a lower haloalkyl;

PG is a protecting group;

the dashed curve

represents a cyclic moiety;

R is a support moiety optionally attached through one or more linkers to the cyclic moiety.

In some embodiments, L has the structure of

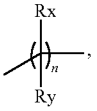

wherein Rx and Ry are independently selected from a group consisting of H, Me, Et, Pr and Bu; or Rx, C and Ry together form a 4-6-membered ring, and no is an integer between 1 and 4. In some embodiments, L is an optionally substituted $C_{1-2}$ alkyl. In some embodiments, L is a methylene. In some embodiments, L is an ethylene.

Other embodiments include compounds represented by Formula (Ia) or (IIa)

(Ia)

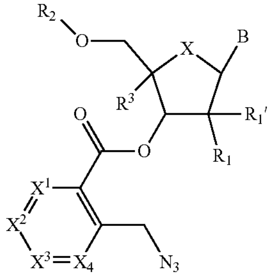

(IIa)

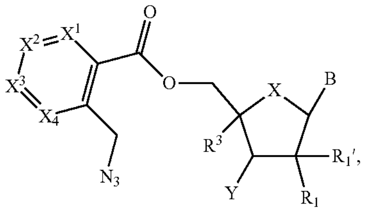

wherein $X^1$, $X^2$, $X^3$, and $X^4$ are independently selected from CR, $CR^4$ and N, where at least one of $X^1$, $X^2$, $X^3$, and $X^4$ is CR, and two adjacent $X^1$, $X^2$, $X^3$, and $X^4$ optionally form a substituted ring that may be substituted;

$R^1$ and $R^{1'}$ are independently selected from H, OPG, F, OR", and $O(CR'_2)_{1-2}OCR'_3$;

$R^2$ is selected from H, a lower alkyl, a lower haloalkyl, PG, an optionally protected nucleotide, a prodrug moiety, and an optionally protected oligonucleotide;

$R^3$ is selected from H, OPG, F, and OR", or $R^1$ and $R^3$ together form an optionally substituted 2-4 atom bridge;

R' is independently selected from H, F, aryl, a lower alkyl, and a lower haloalkyl;

R" is independently selected from H, aryl, a lower alkyl, and a lower haloalkyl;

PG is a protecting group $R^4$ is independently selected from H, alkyl, alkoxyl, aryl, halide, $NO_2$, and substituted carbonyl.

The support moiety may be a solid support moiety or a soluble support moiety. Attaching the soluble support moiety to the compound described herein (e.g., nucleotide, nucleoside or oligonucleotide) can provide an attunable solubility under certain conditions. In some embodiments, the soluble support moiety allows the compound to have attunable solubility upon change of the polarity of the solvent system. In some embodiments, the said solvent system can be a single solvent or a mixture of solvents. In some embodiments, the compound having a soluble support moiety is soluble in less polar solvent, and precipitates upon an increase of the polarity of the solvent system (e.g., by addition of more polar solvent(s)). In other embodiments, the compound having a soluble support moiety is soluble in a polar solvent and precipitates upon a decrease of the polarity of the solvent system (e.g., by addition of less polar solvent(s)). In some embodiments, the soluble support moiety allows the compound to be soluble or freely soluble in dichloromethane (DCM), and allows the compound to be practically insoluble or insoluble in dioxane/water (9:1).

In some embodiments, the support moiety is attached through one or more (e.g., 1, 2 or 3) linkers. Certain embodiments include where R is represented by:

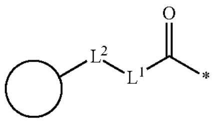 or 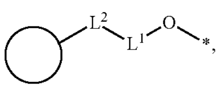

$L^1$ and $L^2$ are optional linkers, and the circle is a moiety that is connected to a solid support or a moiety that provides selective solubility to the compound. For example, in some embodiments, R is represented by:

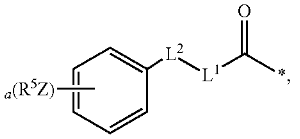 or

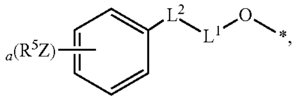

wherein $L^1$ is selected from a bond, an optionally substituted $C_{1-6}$ alkylene group, an optionally substituted $C_{2-6}$ alkenylene group, an optionally substituted $C_{2-6}$ alkynylene group, an optionally substituted cycloalkyl group, an optionally substituted $C_{6-10}$ aryl, an optionally substituted 5-10 membered heteroaryl, and an optionally substituted 4-8 membered heterocyclic group;

$L^2$ is selected from a single bond, —O— or —N(R')—, and C(O);

each Z independently is selected from O, NR", and a bond;

each $R^5$ is independently selected from an alkyl group, an alkenyl group, an alkynyl group, and an ethylene glycol group; and a is an integer of 1-5.

In some embodiments, $L^1$ is a saturated heterocyclic group composed of one or more nitrogen atom (e.g., 1, 2, or 3 N atoms) and carbon atoms and/or having from 5 to 7 ring atoms, and $L^2$ is selected from a single bond, —O— or —N(R')—, and C(O). In some embodiments, Z is O and $R^5$ is a $C_{10-40}$ alkyl group. In some embodiments, a is an integer of 1-3.

R can represent the support moiety applicable for the methods described herein. Some embodiments include where R is represented by:

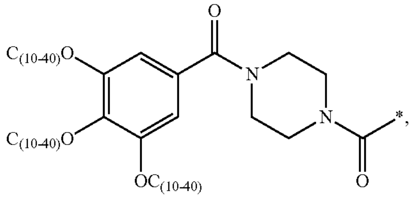 such as

-continued

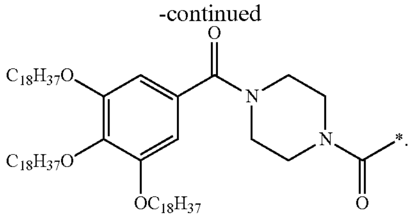

Other support groups and linkers are disclosed, e.g., in US Pub. No. 2018/0291056, US Pub. No. 2018/0282365, U.S. Pat. Nos. 10,214,555, 9,284,344, WO/2018/203574, each of which is incorporated by reference. Other applicable soluble support includes the support used in liquid phase synthesis including polymer based liquid synthesis; ionic liquid tag-assisted synthesis, fluorous tag-assisted synthesis, tetravalent cluster synthesis, adamntylmethylester synthesis, alkyl chain-assisted synthesis, product anchored sequential synthesis (PASS) method, solution-phase synthesis using polymer-supported, and AJIPHASE® for oligonucleotide synthesis. The liquid phase synthesis and reagents described in *Synthesis of Therapeutic Oligonucleotides,* 2018, ISBN: 978-981-13-1911-2 are incorporated by reference. Examples of the soluble support include polyvinyl alcohol, PEG, cellulose-based polymer, pentaerythritol-based support, cyclodextrin and cyclodextrin derivatives, Ajiphase anchor, (adman-1-yl)acetyl based support, imidazolium ion tag, ASS+ Z-ACSS supports, tetrapodal pentaerythritol-based support, tetrakis(triazoylphenyl)-adamantine derived support. Applicable supports can be found in Molina, A. G., & Sanghvi, Y. S. (2019). *Liquid-phase oligonucleotide synthesis: Past, present, and future predictions. Current Protocols in Nucleic Acid Chemistry*, e82. doi: 10.1002 cpnc.82, which is incorporated herein by reference.

In some embodiments, X is O, $R^1$ is F or OR" and $R^{1'}$ is H. Some embodiments also $R^2$ is an optionally protected nucleotide or an optionally protected oligonucleotide. The optionally protected oligonucleotide may include 2 to 40 nucleotides, which are optionally modified in the same manner as the cyclic portion in Formula (I) or (II). In other words, the nucleotides may be modified with X, Y, $R^1$, $R^{1'}$, $R^2$ and $R^3$ as disclosed for Formula (I) or (II). The nucleotides can include intersubunit linkages selected from phosphodiester, thiophosphate, phosphoramidate, and thiophosphoramidate linkages. The nucleobases of the nucleotides may be optionally protected natural or unnatural nucleobases. In one embodiment, all nucleobases are protected.

Other embodiments include where the compound is represented by the following Formula (Ib) or Formula (Ic):

(Ib)

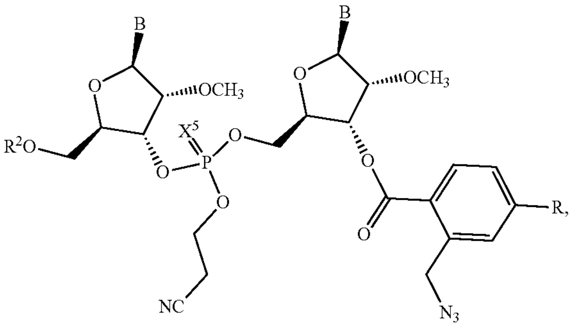

(Ic)

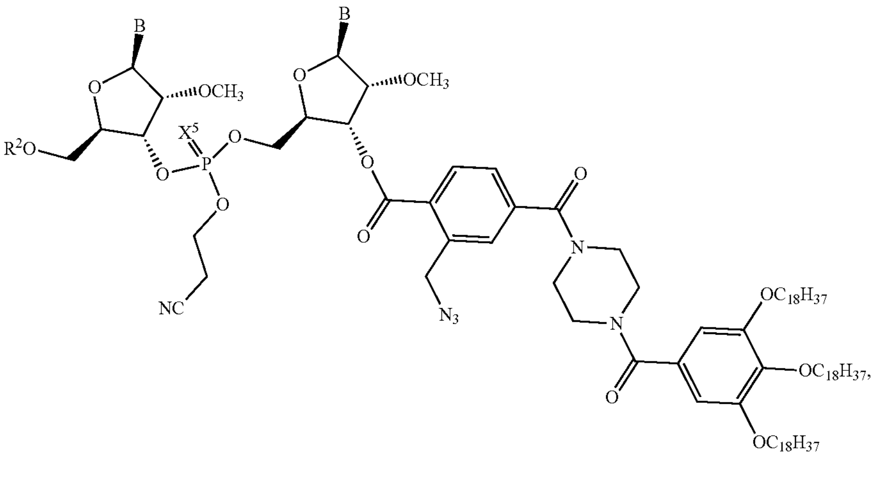

wherein $X^5$ is absent, O or S and the remaining substituents are the same as Formula (I) or Formula (II) (or sub embodiments disclosed herein).

Other embodiments include a compound of the following formula (Id) or (Ie):

(Id)

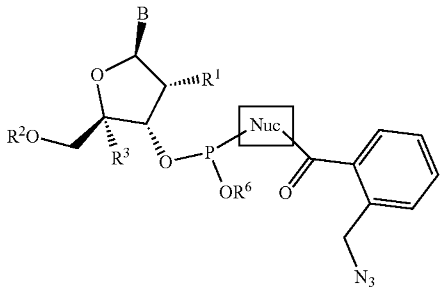

or (Ie)

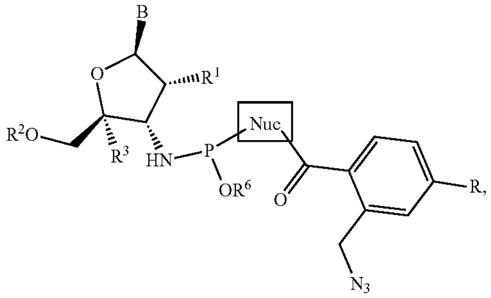

wherein

Nuc is an oligonucleotide subunit having 1-30 linked nucleosides;

B is a protected natural or unnatural nucleobase;

$R^1$ is selected from H, OPG, F, OR", and $O(CR'_2)_{1-2}OCR'_3$;

$R^2$ is selected from H and PG;

$R^3$ is selected from H, OPG, F, and OR", or $R^1$ and $R^3$ together form an optionally substituted 2-4 atom bridge;

R' is independently selected from H, F, aryl, a lower alkyl, and a lower haloalkyl;

R" is independently selected from H, aryl, a lower alkyl, and a lower haloalkyl;

PG is a protecting group;

$R^6$ is selected from a counterion, an alkyl (e.g., a methyl), and a 2-cyanoethyl; and R is a solid support or a soluble support moiety optionally attached through one or more linkers to the cyclic moiety.

Methods of Preparation

The present disclosure also includes methods of selectively conjugating an oligomer, such as an oligonucleotide. Certain embodiments relate to a method of selectively conjugating an oligomer represented by Formula (I-A) or (II-A) having protected nucleobases, (I-A)

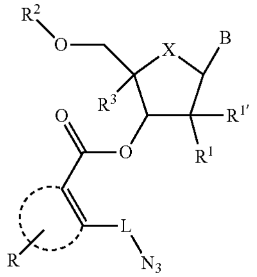

or (II-A)

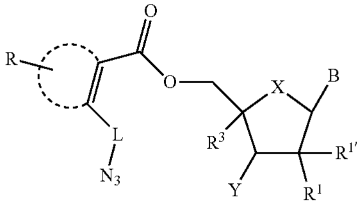

or a salt thereof, wherein

X is selected from O, S, NR" and $C(R')_2$;

B is a protected nucleobase;

$R^1$ and $R^{1'}$ are independently selected from H, OPG, F, OR", and $O(CR'_2)_{1-2}OCR'_3$;

$R^2$ is an optionally protected nucleotide or an oligonucleotide that is protected at the 5' position comprising protected nucleotides;

$R^3$ is selected from H, OPG, F, and OR", or $R^1$ and $R^3$ together form an optionally substituted 2-4 atom bridge;

R' is independently selected from H, F, aryl, a lower alkyl, and a lower haloalkyl;

R" is independently selected from H, aryl, a lower alkyl, and a $C_{1-4}$haloalkyl;

PG is a protecting group;

Y is selected from OH, OR", OPG, NHPG, NHR", an optionally protected nucleotide, and an optionally protected oligonucleotide;

L is $C_{1-4}$ alkyl optionally substituted with one or more substituents.

In some embodiments, L is CRxRy, wherein Rx and Ry are independently selected from the group consisting of H, Me, Et, Pr, and Bu; or Rx, C and Ry together form a 3 to 6-membered ring. In some embodiments, L is an optionally substituted $C_{1-2}$ alkyl. In some embodiments, L is a methylene. In some embodiments, L is an ethylene.

the dashed curve

represents a cyclic moiety;

R is a support moiety optionally attached through one or more linkers to the cyclic moiety, the method comprising (a) reacting the oligomer represented by Formula (I-A) or (II-A) having protected nucleobases to form the following Formula (III):

(III)

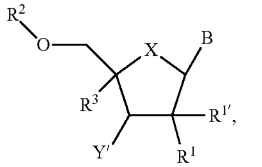

and wherein B is a protected natural or unnatural nucleobase; Y' is OH, OR", or NHR"; R" is independently selected from H, aryl, a lower alkyl, and a $C_{1-4}$ haloalkyl; and (b) reacting the compound of Formula (III) at the 3' position to form a new covalent bond to a second compound, Certain embodiments include a method of selectively conjugating an oligomer represented by Formula (I-1) having protected nucleobases, (I-1)

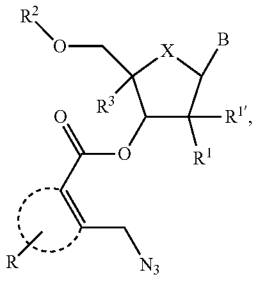

or a salt thereof, wherein

X is selected from O, S, NR" and $C(R')_2$;

B is a protected natural or unnatural nucleobase;

$R^1$ and $R^{1'}$ are independently selected from H, OPG, F, OR", and $O(CR'_2)_{1-2}OCR'_3$;

$R^2$ is an oligonucleotide that is protected at the 5' position comprising protected natural or unnatural nucleobases;

$R^3$ is selected from H, OPG, F, and OR", or $R^1$ and $R^3$ together form an optionally substituted 2-4 atom bridge;

R' is independently selected from H, F, aryl, a lower alkyl, and a lower haloalkyl;

R" is independently selected from H, aryl, a lower alkyl, and a lower haloalkyl;

PG is a protecting group;

the dashed curve

represents a cyclic moiety;

R is a support moiety optionally attached through one or more linkers to the cyclic moiety, comprising (a) reacting the oligomer represented by Formula (I-1) having protected nucleobases to form the following Formula (III):

(III)

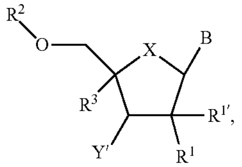

and wherein B is a protected natural or unnatural nucleobase; Y' is OH, OR", or NHR"; R" is independently selected from H, aryl, a lower alkyl, and a $C_{1-4}$ haloalkyl; and (b) reacting the compound of Formula (III) at the 3' position to form a new covalent bond to a second compound.

In some embodiments, the compound of Formula (I) is represented by the following Formula (If):

(If)

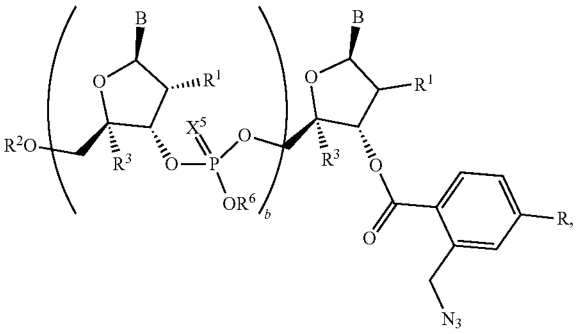

wherein $X^5$ is O or S;

$R^2$ is PG;

$R^6$ is selected from a counterion, a methyl and a 2-cyanoethyl; and b is an integer of 1 to 30.

In certain embodiments, step (b) comprises reacting the compound of Formula (III) at the 3' position to form a covalent bond with the second compound. In some embodiments, step (b) comprises reacting the compound of Formula (III) at the 3' position with a protecting group, followed by deprotecting the compound at the 5' position and reacting the resulting compound at the 5' position to form a covalent bond with the second compound.

Certain embodiments include removing the support, e.g., through a Staudinger-type reaction. For example, the support may be removed by contacting the compound with $Ph_3P$. In some embodiments, the support is removed without removing protecting groups from the nucleobases. Further embodiments include deprotecting the nucleobases of the oligonucleotide after removal of the support.

Some embodiments relate to a method of coupling a first nucleoside subunit and a nucleoside phosphoramidite, the method comprising (a) reacting the first nucleoside subunit with the nucleoside phosphoramidite, wherein the first nucleoside subunit is covalently bound to the following moiety (A):

(A)

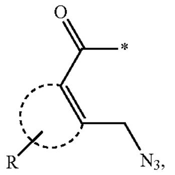

where R is a support moiety optionally attached through one or more linkers to the cyclic moiety, and the dashed lines represent additional bonds and the * represents the point where the moiety is bound to the first nucleoside.

In some embodiments, R is represented by

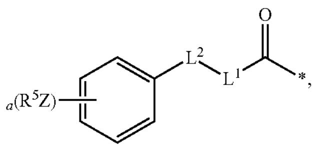

or

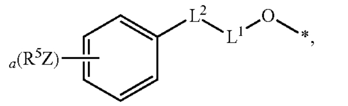

wherein $L^1$ is selected from a bond, an optionally substituted $C_{1-6}$ alkylene group, an optionally substituted $C_{2-6}$ alkenylene group, an optionally substituted $C_{2-6}$ alkynylene group, an optionally substituted cycloalkyl group, an optionally substituted $C_{6-10}$ aryl, an optionally substituted 5-10 membered heteroaryl, and an optionally substituted 4-8 membered heterocyclic group;

$L^2$ is selected from a single bond, —O— or —N(R')—, and C(O);

Z is selected from O, NR", and a bond;

$R^5$ is selected from an alkyl group, an alkenyl group, an alkynyl group, and an ethylene glycol group; and a is an integer of 1-3

Other embodiments include a method of coupling a first nucleoside subunit and a nucleoside phosphoramidite, the method comprising (A) reacting the first nucleoside subunit with the nucleoside phosphoramidite, wherein the first nucleoside subunit is covalently bound to the following moiety (A):

(A)

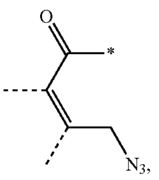

where the dashed lines represent additional bonds and the * represents the point where the moiety is bound to the first nucleoside. In some embodiments the additional bonds are not to hydrogen. In some embodiments, the * is attached at the 3' or 5' point of a nucleotide. In some embodiments, the moiety (A) has the following structure:

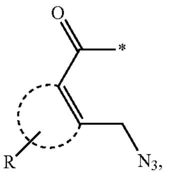

wherein R is a support moiety optionally attached through one or more linkers to the cyclic moiety.

In some embodiments, the resulting compound can have the structure of

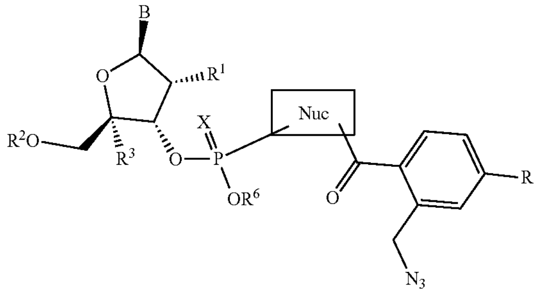

or

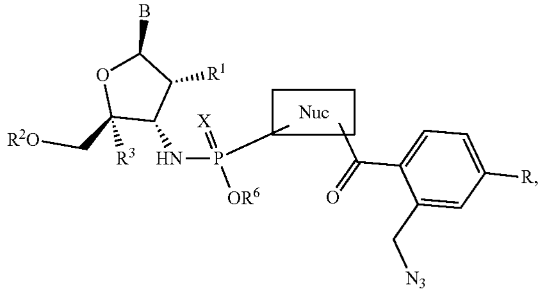

wherein

Nuc is an oligonucleotide subunit having 1-30 linked nucleosides;

B is a protected natural or unnatural nucleobase;

X is absent, O or S;

$R^1$ is selected from H, OPG, F, OR", and $O(CR'_2)_{1-2}OCR'_3$;

$R^2$ is selected from H and PG;

$R^3$ is selected from H, OPG, F, and OR", or $R^1$ and $R^3$ together form an optionally substituted 2-4 atom bridge;

R' is independently selected from H, F, aryl, a lower alkyl, and a lower haloalkyl;

R" is independently selected from H, aryl, a lower alkyl, and a lower haloalkyl;

PG is a protecting group;

$R^6$ is selected from a counterion, a methyl and a 2-cyanoethyl; and

R is a solid support or a soluble support moiety optionally attached through one or more linkers to the cyclic moiety In some embodiments, the resulting coupled nucleoside has the following structure:

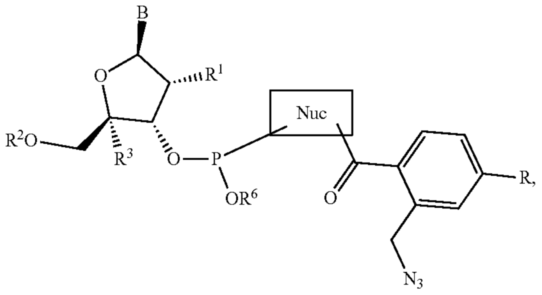

wherein Nuc is an oligonucleotide subunit having 1-30 linked nucleosides,

B is a protected natural or unnatural nucleobase;

In some embodiments, the methods of synthesizing an oligonucleotide via a convergent synthesis further comprises reacting the resulting 5'-deblocked product having a support moiety optionally attached through one or more linkers with a third nucleotide, and oxidizing or thiolating the resulting product. In some embodiments, this step is performed more than once. In some embodiments, the third nucleotide comprises two or more nucleotides. In some embodiments, the methods of synthesizing an oligonucleotide via a convergent synthesis comprise coupling dimers, trimers, and/or 4-mers to synthesize an oligonucleotide of a desirable length.

It is to be understood that the above steps can be performed as needed for a convergent synthesis. For example, the following embodiment shows an exemplary convergent synthesis of a 21-mer nucleotide.

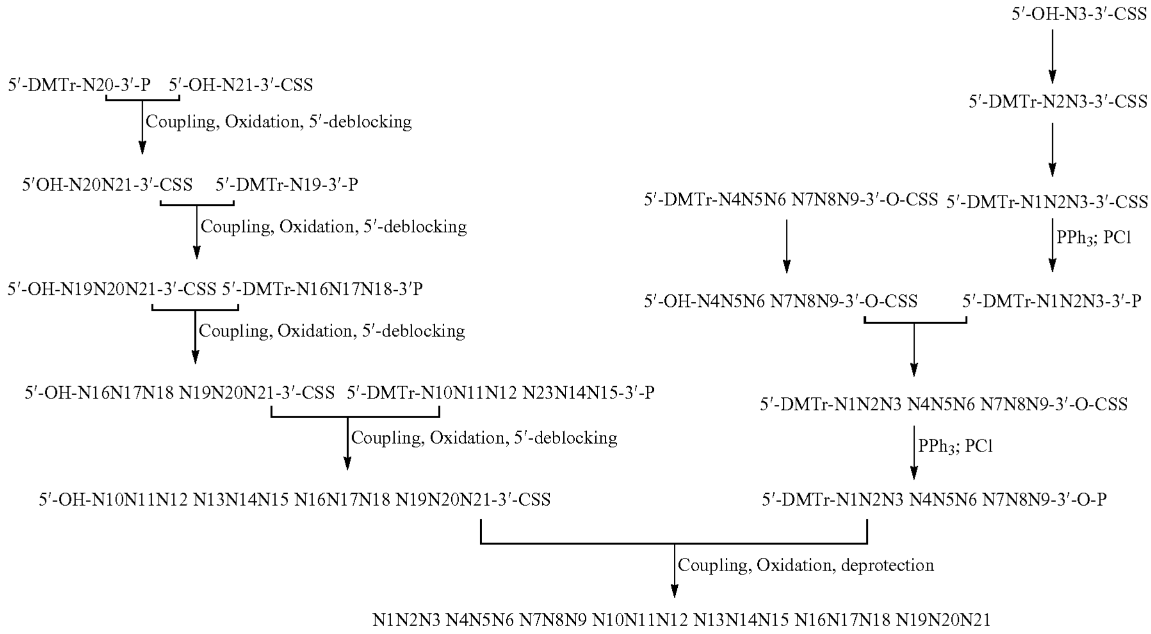

CSS = Cleaveable support
P = Phosphramidite $R^1$ is selected from H, OPG, F, OR", and $O(CR'_2)_{1-2}OCR'_3$;

$R^2$ is selected from H and PG;

$R^3$ is selected from H, OPG, F, and OR", or $R^1$ and $R^3$ together form an optionally substituted 2-4 atom bridge;

R' is independently selected from H, F, aryl, a lower alkyl, and a lower haloalkyl;

R" is independently selected from H, aryl, a lower alkyl, and a lower haloalkyl;

PG is a protecting group;

$R^6$ is selected from a counterion, a methyl and a 2-cyanoethyl; and

R is a support moiety optionally attached through one or more linkers to the cyclic moiety.

Embodiments disclosed herein include methods of synthesizing an oligonucleotide via a convergent synthesis, comprising coupling a first nucleotide with a second nucleotide having a support moiety optionally attached through one or more linkers; oxidizing the resulting product and deblocking the resulting product at the 5' position.

In the convergent synthesis scheme described above, the protected nucleotide N20 can be coupled with nucleotide N21 which is attached to a cleavable support (e.g., soluble support), the resulted dimer then undergoes oxidation and 5'-deblocking to provide a dimer N20N21 that is attached to the cleavable support. The dimer is then coupled to N19 through a similar process to produce a trimer N19N2N21. The trimer is then coupled to another trimer to produce a hexamer that is attached to the cleavable support. The hexamer can then be coupled to another hexamer to produce a 12mer. The scheme above shows an example of the preparation of a 21mer, and the process can be adjusted to prepare an oligomer of any desired length. The cleavable support attached to the oligomer can be a soluble support moiety, which can be cleaved from the oligonucleotide and then recovered from the reaction through selective precipitation.

In addition, the process described above can be particularly suitable for preparation of oligomers containing nucleotide repeats such oligomer consisted of AC repeats, AG repeats, CG repeats, AT repeats or other nucleotide repeats. Once a dimer is formed after the initial coupling step, the dimer can be then coupled repeatedly to form an oligomer having the dimer nucleotide repeats. In the scheme above, CSS is a cleavable support, and one example of the CSS is

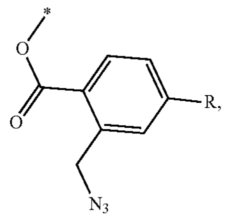

and P is a phosphoramidite (e.g.,

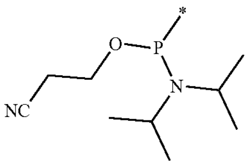

), and PCI is a phosphitylation reagent.

Definitions

It is to be understood that the terminology used herein is for the purpose of describing particular embodiments only and is not intended to limit the scope of the present disclosure. The following definitions shall apply unless otherwise indicated.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

Generally, reference to a certain element such as hydrogen or H is meant to include all isotopes of that element. For example, if an R group is defined to include hydrogen or H, it also includes deuterium and tritium. Hence, isotopically labeled compounds are within the scope of the disclosure.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

Alkyl groups include straight chain and branched alkyl groups having from 1 to about 40 carbon atoms, e.g., 1 to about 20 carbon atoms, such as, from 1 to 12 carbons or, in some embodiments, from 1 to 8, 1 to 6, or 1 to 4 carbon atoms. Alkyl groups further include cycloalkyl groups as defined below. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above. Lower alkyl may be optionally substituted and includes from 1 to 12 carbons or, in some embodiments, from 1 to 8, 1 to 6, or 1 to 4 carbon atoms.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include mono-, bicyclic and polycyclic ring systems, such as, for example bridged cycloalkyl groups as described below, and fused rings, such as, but not limited to, decalinyl, and the like. In some embodiments, polycyclic cycloalkyl groups have three rings. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-, 2,5- or 2,6-disubstituted cyclohexyl groups, which may be substituted with substituents such as those listed above.

Aryl groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. In some embodiments, heterocyclyl groups include 3 to 20 ring members, whereas other such groups have 3 to 6, 3 to 10, 3 to 12, or 3 to 15 ring members. Heterocyclyl groups encompass unsaturated, partially saturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. However, the phrase does not include heterocyclyl groups that have other groups, such as alkyl, oxo or halo groups, bonded to one of the ring members. Rather, these are referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridyl, pyridazinyl, pyrimidinyl, pyrazinyl, thiophenyl, benzothiophenyl, furanyl, benzofuranyl, indolyl, azaindolyl (pyrrolopyridyl), indazolyl, benzimidazolyl, imidazopyridyl (azabenzimidazolyl), pyrazolopyridyl, triazolopyridyl, benzotriazolyl, benzoxazolyl, benzothiazolyl, benzothiadiazolyl, imidazopyridyl, isoxazolopyridyl, thianaphthalenyl, purinyl, xanthinyl, adeninyl, guaninyl, quinolinyl, isoquinolinyl, tetrahydroquinolinyl, quinoxalinyl, and quinazolinyl groups. Although the phrase "heteroaryl groups" includes fused ring compounds such as indolyl and 2,3-dihydro indolyl, the phrase does not include heteroaryl groups that have other groups bonded to one of the ring members, such as alkyl groups. Rather, heteroaryl groups with such substitution are referred to as "substituted heteroaryl groups." Representative substituted heteroaryl groups may be substituted one or more times with various substituents such as those listed above.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

"Carbonyl" refers to the divalent group —C(O)— which is equivalent to —C(═O)—. Substituted carbonyl means a carbonyl attached to an atom and attached at the other valent point to a moiety disclosed herein (e.g., optionally substituted alkyl, aryl, herteroaryl, etc.).

The term "amine" (or "amino") as used herein refers to —$NHR^4$ and —$NR^5R^6$ groups, wherein $R^4$, $R^5$ and $R^6$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is $NH_2$, methylamino, dimethylamino, ethylamino, diethylamino, propylamino, isopropylamino, phenylamino, or benzylamino.

"Halo" or "halide" or "halogen" refers to fluoro, chloro, bromo and iodo. IN some embodiments, the halide is F.

"Optionally substituted" refers to a group selected from that group and a substituted form of that group. A "substituted" group, refers to that group substituted with any substituent described or defined below. In one embodiment, substituents are selected from, for example, $CF_3$, $OCF_3$, halo, haloaryl, alkoxy, aryloxy, haloalkoxy, dihydroxy, aminohydroxy, carboxy, amido, sulfoxy, sulfonyl, haloaryloxy, aryl, benzyl, benzyloxy, heteroaryl, nitrile, $C_1$-$C_6$ alkyl, $C_1$-$C_6$ alkenyl, $C_1$-$C_6$ alkynyl, $C_3$-$C_6$ cycloalkyl, $C_1$-$C_6$ haloalkyl, $C_1$-$C_6$ haloalkenyl, $C_1$-$C_6$ haloalkynyl, $C_3$-$C_6$ halocycloalkyl, $C_6$-$C_{10}$ aryl, $C_3$-$C_8$ cycloalkyl, $C_2$-$C_{10}$ heterocyclyl, $C_1$-$C_{10}$ heteroaryl, —$N_3$, nitro, —$CO_2H$ or a $C_1$-$C_6$ alkyl ester thereof, any of the functional groups described or defined below, or combinations thereof.

"Cyclic moiety" refers to a cycloalkyl, aryl, heteroaryl, or heterocyclyl, each of which may be optionally substituted.

"Support moiety" refers to a moiety attached to a nucleotide that allows for separation of the support-anchored oligonucleotide chain from the monomeric building block and other small molecular reagents and byproducts after, e.g., a coupling, oxidation and deprotection step. Support moiety includes solid support moieties and soluble support moieties.

"Solid support moiety" has its usual meaning as understood by those skilled in the art of organic synthesis conducted on solid phase supports. A number of different solid supports suitable for the synthesis of oligonucleotides and methods for preparation are given by Pon, 1993, *Methods in Molecular Biology, vol.* 20*: Protocols for Oligonucleotides and Analogs*, Humana Press, which is incorporated herein by reference in its entirety. In particular, solid supports include controlled pore glass or a polymeric support, such as a bead, including a polyvinyl acetate or a polystyrene bead.

As used herein, "soluble support moiety" means a support moiety that is capable of being selectively solubilized in a solvent system under certain conditions or solvent polarity and to be insoluble and to precipitate out of solution under different conditions or different solvent polarity in that solvent system and to allow for substantial recovery of all the support moiety from solution by precipitation. Examples of the soluble support include polyvinyl alcohol, PEG, cellulose-based polymer, pentaerythritol-based support, cyclodextrin and cyclodextrin derivatives, Ajiphase anchor, (adman-1-yl)acetyl based support, imidazolium ion tag, ASS+ Z-ACSS supports, tetrapodal pentaerythritol-based support, tetrakis(triazoylphenyl)-adamantine derived support.

"Linkers" refer to a chemical moiety in a molecule comprising a covalent bond or a chain of atoms that covalently attaches one moiety or molecule to another, e.g. a nucleotide/nucleoside or oligonucleotide. A "cleavable linker" refers to a linker that can be cleaved under specified conditions to allow release of the solid support from the remainder of the reagent. For example, the linker is stable under oligonucleotide synthesis conditions, but is unstable to the conditions used to deprotect the synthetic oligonucleotide (eg, 55° C. or room temperature incubation in ammonium hydroxide). Examples of the cleavable linker can include, but are not limited to, esters, carbonates, diisopropylsiloxy ethers, phosphate ester modifications and the like.

"Nucleoside" refers to a compound consisting of a nucleobase linked to the C-1' carbon of a sugar, such as ribose, arabinose, xylose, and pyranose, in the natural β or the α anomeric configuration. The nucleoside can include naturally occurring nucleoside and also modified nucleoside. The sugar may be substituted or unsubstituted. Substituted ribose sugars include, but are not limited to, those riboses in which one or more of the carbon atoms, for example the 2'-carbon atom, is substituted with one or more of the same or different Cl, F, —R, —OR, —NR2 or halogen groups, where each R is independently X, $C_1$-$C_6$ alkyl or $C_5$-$C_{15}$ aryl. Ribose examples include ribose, 2'-deoxyribose, 2',3'-dideoxyribose, 2'-haloribose, 2'-fluororibose, 2'-chlororibose, and 2'-alkylribose, e.g. 2'-O-methyl, 4'-α-anomeric nucleotides, 1'-α-anomeric nucleotides (Asseline (1991) Nucl. Acids Res. 19:4067-74), 2'-4'- and 3'-4'-linked and other "locked" or "LNA", bicyclic sugar modifications (WO 98/22489; WO 98/39352; WO 99/14226). Sugars include modifications at the 2'- or 3'-position such as methoxy, ethoxy, allyloxy, isopropoxy, butoxy, isobutoxy, methoxyethyl, alkoxy, phenoxy, azido, amino, alkylamino, fluoro, chloro and bromo. Nucleosides and nucleotides include the natural D configurational isomer (D-form), as well as the L, configurational isomer (L-form) (Beigelman, U.S. Pat. No. 6,251,666; Chu, U.S. Pat. No. 5,753,789; Shudo, EP0540742; Garbesi (1993) Nucl. Acids Res. 21:4159-65; Fujimori (1990) J. Amer. Chem. Soc. 112:7435; Urata, (1993) Nucleic Acids Symposium Ser. No. 29:69-70). When the nucleobase is purine, e.g. A or G, the ribose sugar is usually attached to the N9-position of the nucleobase. When the nucleobase is pyrimidine, e.g. C, T or U, the pentose sugar is usually attached to the N1-position of the nucleobase (Kornberg and Baker, (1992) DNA Replication, 2nd Ed., Freeman, San Francisco, Calif.).

"Nucleotide" refers to a phosphate ester of a nucleoside, as a monomer unit or within a nucleic acid or an oligomer. "Nucleotide 5'-triphosphate" refers to a nucleotide with a triphosphate ester group at the 5' position, and are sometimes denoted as "NTP", or "dNTP" and "ddNTP" to particularly point out the structural features of the ribose sugar. The triphosphate ester group may include sulfur substitutions for the various oxygens, e.g. α-thio-nucleotide 5'-triphosphates. For a review of nucleic acid chemistry, see: Shabarova, Z. and Bogdanov, A. Advanced Organic Chemistry of Nucleic Acids, VCH, New York, 1994. The nucleotide can include naturally occurring nucleotide and also modified nucleotide.

As used herein, "oligonucleotide" refers to a single-stranded and double-stranded polymers of nucleotide monomers, including 2'-deoxyribonucleotides (DNA) and ribonucleotides (RNA) linked by internucleotide phosphodiester bond linkages, e.g. 3'-5' and 2'-5', inverted linkages, e.g. 3'-3' and 5'-5', branched structures, or internucleotide analogs. Polynucleotides have associated counter ions, such as H+, NH4+, trialkylammonium, Mg2+, Na+ and the like. A polynucleotide may be composed entirely of deoxyribonucleotides, entirely of ribonucleotides, or chimeric mixtures thereof. Polynucleotides may be comprised of nucleobase and sugar analogs. Polynucleotides typically range in size from a few monomeric units, e.g. 5-40 when they are more commonly frequently referred to in the art as oligonucleotides, to several thousands of monomeric nucleotide units. Unless denoted otherwise, whenever a polynucleotide sequence is represented, it will be understood that the nucleotides are in 5' to 3' order from left to right and that "A" "G" "C" "T", when used in DNA, denote deoxyadenosine, deoxyguanosine, deoxycytidine, and thymidine respectively, and that "A" "G" "C" "U", when used in RNA, denote adenosine, guanosine, cytidine, and uridine respectively.

Those of skill in the art will appreciate that compounds of the disclosure may exhibit the phenomena of tautomerism, conformational isomerism, geometric isomerism and/or optical isomerism. As the formula drawings within the specification and claims can represent only one of the possible tautomeric, conformational isomeric, optical isomeric or geometric isomeric forms, it should be understood that the disclosure encompasses any tautomeric, conformational isomeric, optical isomeric and/or geometric isomeric forms of the compounds having one or more of the utilities described herein, as well as mixtures of these various different forms.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

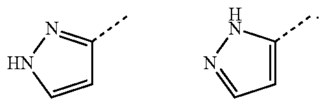

As readily understood by one skilled in the art, a wide variety of functional groups and other structures may exhibit tautomerism, and all tautomers of compounds as described herein are within the scope of the present disclosure.

Stereoisomers of compounds, also known as "optical isomers," include all chiral, diastereomeric, and racemic forms of a structure, unless the specific stereochemistry is expressly indicated. Thus, compounds used in the present disclosure include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these are all within the scope of the disclosure.

A "protecting group" or "PG" intends any protecting group suitable for alcohol(s) and amine(s) and which are well known in the art. Non-limiting examples include 2,2,2-trichloroethyl carbonate (Troc), 2-methoxyethoxymethyl ether (MEM), 2-naphthylmethyl ether (Nap), 4-methoxybenzyl ether (PMB), acetate (Ac), benzoate (Bz), benzyl ether (Bn), benzyloxymethyl acetal (BOM), benzyloxymethyl acetal (BOM), methoxymethyl acetal (MOM), methoxypropyl acetal (MOP), methyl ether, tetrahydropyranyl acetal (THP), triethylsilyl ether (TES), triisopropylsilyl ether (TIPS), trimethylsilyl ether (TMS), tert-Butyldimethylsilyl ether (TBS, TBDMS), or tert-butyldiphenylsilyl ether (TBDPS). In the case of a 1,2 diol or 1,2 aminoalcohols suitable protecting groups include acetonide, benzaldehyde acetal or carbonate and others. These protecting groups and others are well known to the skilled artisan, as evidenced by Green et al: Greene's Protective Groups in Organic Synthesis, Fourth Edition Author(s): Peter G. M. Wuts and Theodora W. Greene First published: 10 Apr. 2006, Copyright © 2007 John Wiley & Sons, Inc, the disclosure of which is incorporated by reference.

"Deprotection," "deprotecting," and the like, intend removal of the protecting group by any conventional means known to the skilled artisan or present in Green et al. It will be readily apparent that the conditions for deprotecting depend upon which protecting group is used.

"Pharmaceutically acceptable" refers to a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. and Drug administration.

"Modified nucleoside" or "unnatural nucleoside" refers to a nucleoside having, independently, a modified sugar moiety and/or modified nucleobase. It is understood that nucleosides can be linked through intersubunit linkages, such as phosphodiester intersubunit linkages, thiophosphate intersubunit linkages, phosphoramidate intersubunit linkages, and thiophosphoramidate intersubunit linkages "Modified nucleotides" may refer to a nucleoside and intersubunit linkage together.

"Unmodified" or "natural" nucleobases include the purine bases adenine (A) and guanine (G), and the pyrimidine bases thymine (T), cytosine (C) and uracil (U). "Modified" or "unnatural" nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($-C\equiv C-CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-am-oelhoxy)-H-pyrimido[5,4-b][1,4]benzoxazin-2(3H)-one), carbazole cytidine (2H-pyrimido[4,5-b]indol-2-one), pyridoindole cytidine (H-pyrido[3,2,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine, and 2-pyridone.

In some embodiments, the modified nucleobase is selected from the group consisting of 5-methylcytosine, 2,6-diaminopurine, 5-methyluracil, and a g-clamp. In some embodiments, the g-clamp is

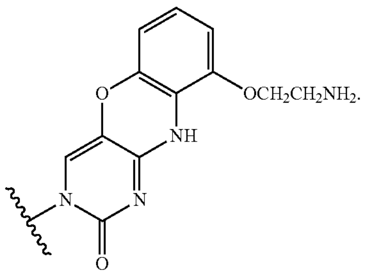

"Conformationally restricted nucleoside" refers to nucleosides having a bridged or bicyclic sugar structure wherein the conformation of the nucleoside may be fixed in a particular configuration. For example, conformationally restricted nucleosides include those with fixed $C_3$'-endo sugar puckering. Exemplary embodiments include bridged nucleic acids (BNAs), e.g., 2',4'-BNA nucleosides such as α-L-Methyleneoxy (4'-$CH_2$—O-2') LNA, β-D-Methyleneoxy (4'-$CH_2$—O-2') LNA, Ethyleneoxy (4'-$(CH_2)_2$—O-2') ENA, 2',4'-$BNA^{NC}$[NH], 2',4'-$BNA^{NC}$[NMe], 2',4'-$BNA^{NC}$[NBn], aminooxy (4'-$CH_2$—O—N(R)-2') BNA, and oxyamino (4'-$CH_2$—N(R)—O-2') BNA. Other exemplary BNA structures include but are not limited to, oligonucleotides having at least one bridge between the 4' and the 2' position of the sugar wherein each of the bridges independently comprises 1 or from 2 to 4 linked groups independently selected from $[C(R_1)(R_2)]_n$—, $C(R_1)=C(R_2)$—, $C(R_1)=N$—, $C(=NR_1)$—, —C(=O)—, —C(=S)—, —O—, $-Si(R_1)_2-$, $-S(=O)_x-$ and $N(R_1)$—; wherein: x is 0, 1, or 2; n is 1, 2, 3, or 4; each $R_1$ and $R_2$ is, independently, H, a protecting group, hydroxyl, $C_1$-$C_{12}$ alkyl, substituted $C_1$-$C_{12}$ alkyl, $C_2$-$C_{12}$alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, a heterocycle radical, a substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(═O)—H), substituted acyl, CN, sulfonyl ($S(=O)_2$-$J_1$), or sulfoxyl (S(═O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(═O)—H), substituted acyl, a heterocycle radical, a substituted heterocycle radical, $C_1$-$C_{12}$ aminoalkyl, substituted $C_1$-$C_{12}$ aminoalkyl or a protecting group. Certain BNAs have been prepared and disclosed in the patent literature as well as in scientific literature (see for example: issued U.S. Pat. Nos. 7,053,207; 6,268,490; 6,770,748; 6,794,499; 7,034,133; 6,525,191; 7,696,345; 7,569,575; 7,314,923; 7,217,805; and 7,084,125, hereby incorporated by reference herein in their entirety. "Conformationally restricted nucleotide" refers to conformationally restricted nucleosides linked through an intersubunit linkage.

In some embodiments, the conformationally restricted nucleoside is selected from optionally substituted LNA or optionally substituted ENA. The optionally substituted LNA or ENA may be substituted by an alkyl moiety, for example a methyl or ethyl on one of the —$CH_2$— moieties.

The following abbreviations are used in this disclosure. 2'-H (deoxyribose) nucleosides are referred to by an uppercase letter corresponding to the nucleobase, e.g., A, C, G, and T. 2'-OH (ribose) nucleosides are referred to by a lowercase r and an uppercase letter corresponding to the nucleobase, e.g., rA, rC, rG, and rU. 2'-O-Me nucleosides are referred to by a lowercase m and an uppercase letter corresponding to the nucleobase, e.g., mA, mC, mG and mU. 2'-MOE nucleosides are referred to by a lowercase "moe" and an uppercase letter corresponding to the nucleobase, e.g., moeA, moeC, moeG and moeU. 2'-ribo-F nucleosides are referred to by a lowercase "f" and an uppercase letter corresponding to the nucleobase, e.g., fA, fC, fG and fU. 2'-arabino-F nucleosides are referred to by a lowercase "af" and an uppercase letter corresponding to the nucleobase, e.g., afA, afC, afG and afU. mA* is 3'-amino-2'-OMe-2,6-Diaminopurine. A* is 3'-amino-2'-deoxy-2,6-Diaminopurine. fA* is 3'-amino-2'-F-2,6-Diaminopurine. LNA nucleosides are referred to by an "L" and an uppercase letter corresponding to the nucleobase, e.g., LA, LC, LG, LT.

For the backbone or intersubunit linkages of the nucleotides, phosphodiester intersubunit linkages are referred to as "po" or are generally not included in sequence details; thiophosphate intersubunit linkages are abbreviated as lowercase "ps"; phosphoramidate intersubunit linkages are abbreviated as lowercase "np"; and thiophosphoramidate intersubunit linkages are abbreviated as lowercase "nps."

N3'→P5' refers to modified nucleotides having intersubunit linkages where the 3' moiety contains N (e.g., NH) and is linked through a P. For example, the following structure has a N3'→P5' linkage:

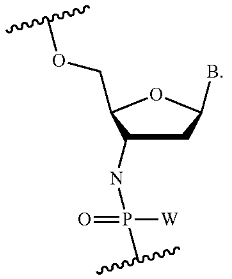

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

This disclosure is not limited to particular embodiments described, as such may vary. It is also to be understood that the terminology used herein is for the purpose of describing particular embodiments only, and is not intended to be limiting, since the scope of the present disclosure will be limited only by the appended claims.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided may be different from the actual publication dates that may need to be independently confirmed.

EXAMPLES

Synthesis

Exemplary compounds useful in methods provided herein are described by reference to the illustrative synthetic schemes for their general preparation below and the specific examples that follow. One skilled in the art will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

Exemplary compounds useful in methods provided herein are described by reference to the illustrative synthetic schemes for their general preparation below and the specific examples to follow.

SCHEME 1

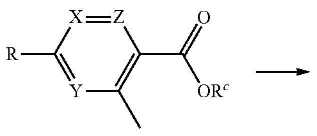

1-I

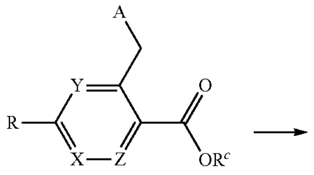

1-II

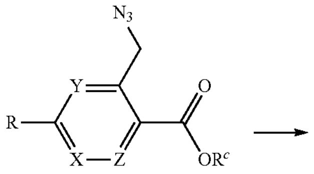

1-III

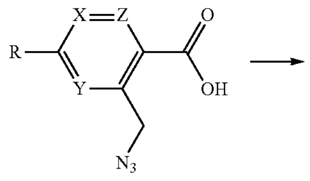

1-IV

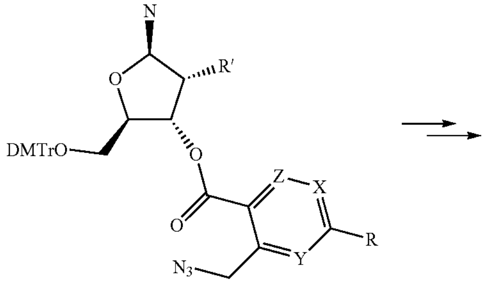

1-V

-continued

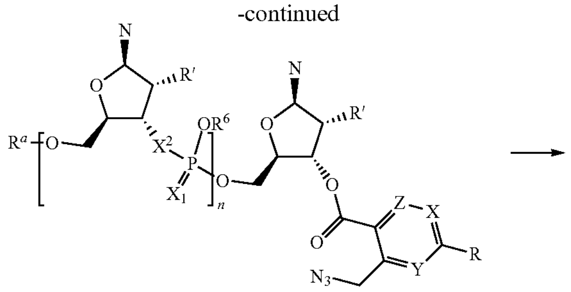

1-VI $R^a$ = DMTr, H

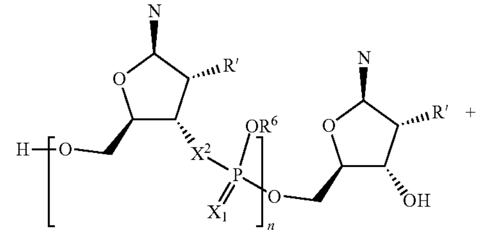

1-VII

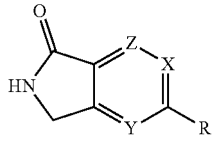

1-VIII

According to SCHEME 1, a commercially available or synthetically accessible compound of formula (1-I), is transformed into an activated intermediate of formula (1-II) positioned for nucleophilic substitution by an azide, employing conditions known to one skilled in the art, to provide a compound of formula (1-III), where A is a halide or mesylate/tosylate/triflate, R is a soluble support or a solid support joined via a spacer, $R^c$ is an alkyl, and X, Y and Z are selected from CH and N, respectively, $X_1$ is O or S, $X_2$ is O or NH, and XZ can be fused with a second ring.

The benzoate ester of formula (1-III) is hydrolyzed, and coupled to 3'-OH of a protected nucleoside employing conditions known to one skilled in the art, to provide a compound of formula (1-V), which is deblocked at 5'-OH and extended to provide a fully protected oligonucleotide of formula (1-VI), according to protocols known to one skilled in the art.

The support of oligonucleotide of formula (1-VI) is selectively cleaved by treatment with a phosphine or hydrogenation, and global deprotection employing conditions known to one skilled in the art, to provide oligonucleotide of formula (1-VII).

SCHEME 2

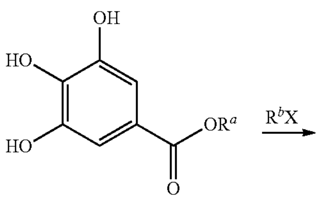

(2-I)

-continued

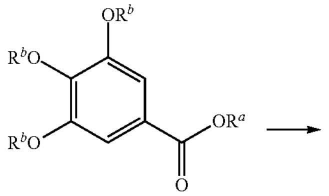

(2-II)

$R^b$ = C10-C18 alkyl, etc

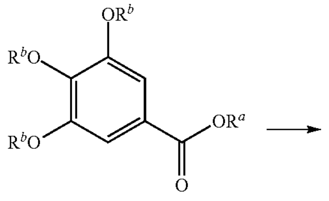

(2-III)

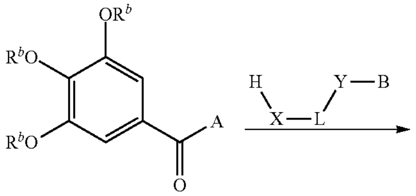

(2-IV)

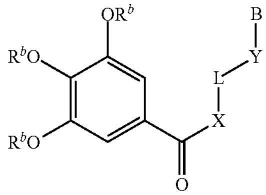

(2-V)

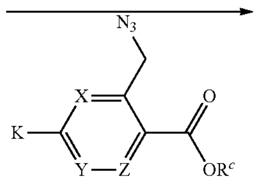

(2-VII)

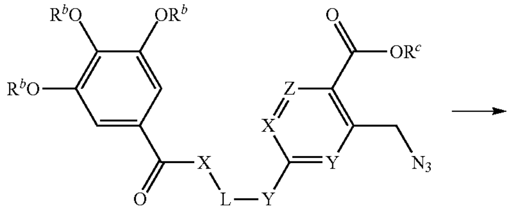

(2-VIII)

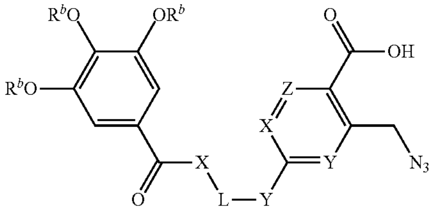

(2-IX)

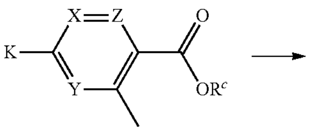

(2-X)

-continued

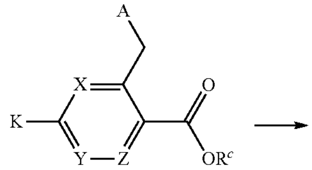

(2-XI)

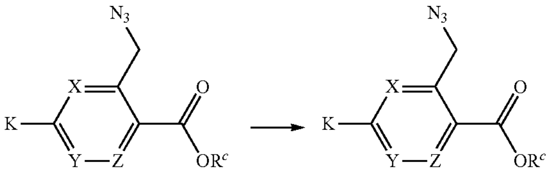

(2-XII) (2-VII)

According to SCHEME 2, a commercially available or synthetically accessible compound of formula (2-I), is alkylated to provide a compound of formula (2-II), which is hydrolyzed and acidified to a benzoic acid of formula (2-III), employing conditions known to one skilled in the art. Activation of compound (2-III) followed by coupling with a spacer leads to the formation of an ester or amide of formula (2-V). Coupling of compound (2-V) with compound (2-VII) gives the azide of formula (2-VIII), employing conditions known to one skilled in the art. Hydrolysis of the benzoate ester of formula (2-VIII) provides a soluble support of formula (2-IX), where A is a halide, and activated leaving group or mesylate/tosylate/triflate, B is a protecting group or a leaving group, K is a nucleophile or a leaving group, $R^a$ and $R^c$ is an alkyl, respectively, $R^b$ is a long chain alkyl (C10-C18) and X, Y and Z are selected from CH and N, respectively, and XZ can be fused with a second ring.

SCHEME 3

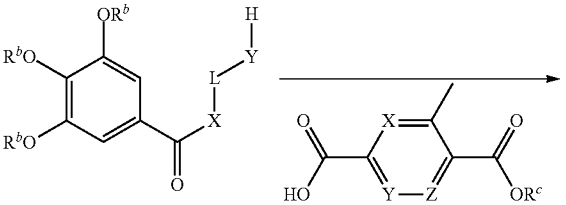

(3-VI) (3-X)

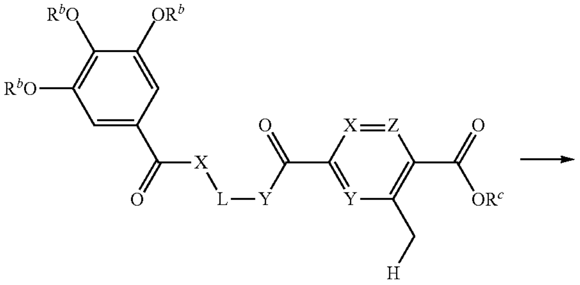

(3-XIII)

-continued
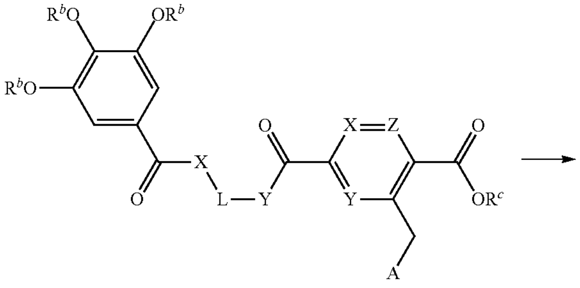
(3-XIV)
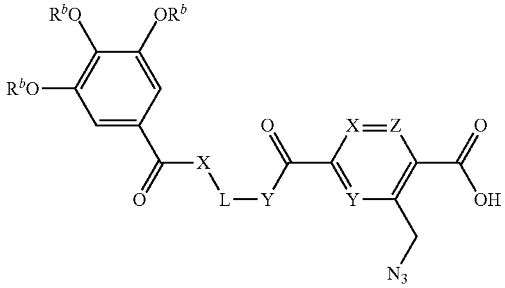
(3-VIII)
Alternatively, according to SCHEME 3, the azido is introduced into the fully constructed molecule scaffold of a soluble support by activation of a substituted toluene, followed by displacement with an azide salt.
SCHEME 4
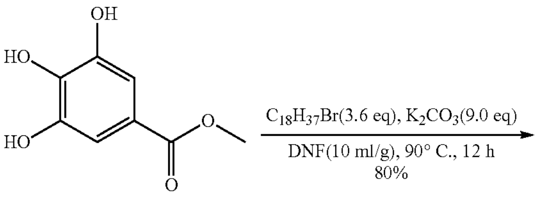
(4-I)
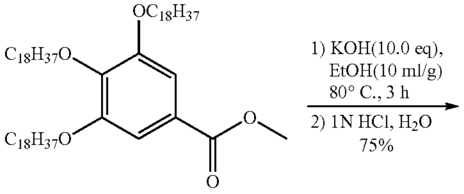
(4-II)
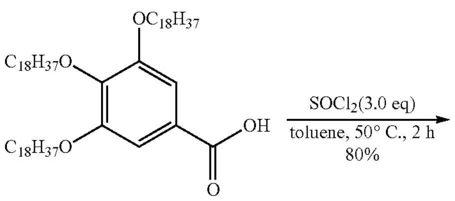
(4-III)
-continued
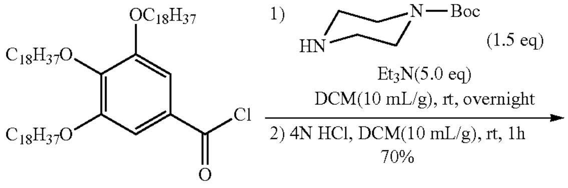
(4-IV)
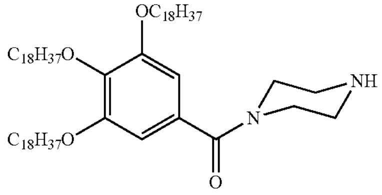
(4-V)
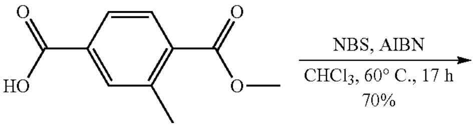
(4-VI)
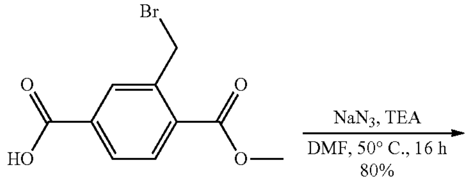
(4-VII)
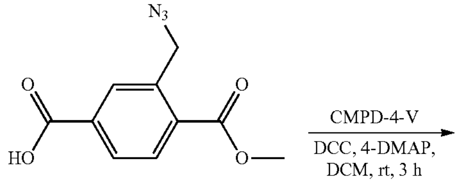
(4-VIII)
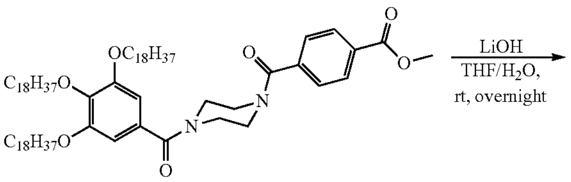
(4-IX)
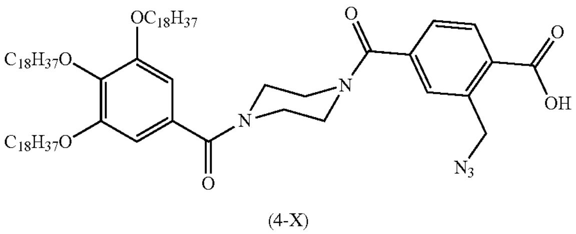
(4-X)

SCHEME 5
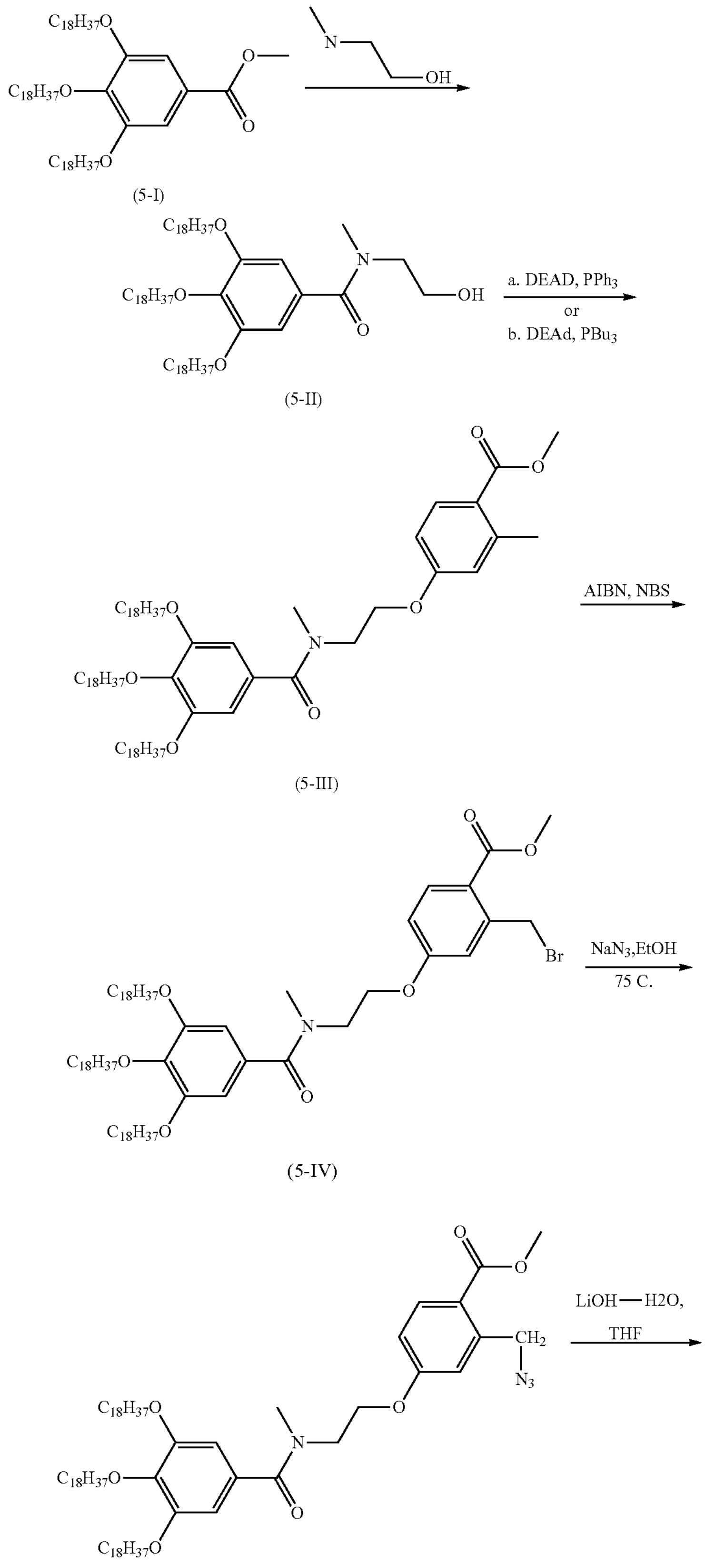
(5-I)
(5-II)
(5-III)
(5-IV)
(5-V)

-continued
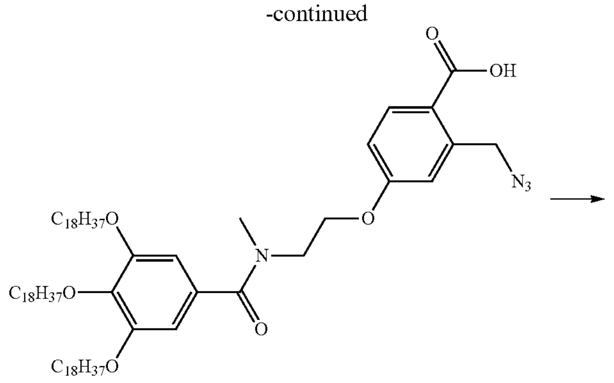
(5-VI)
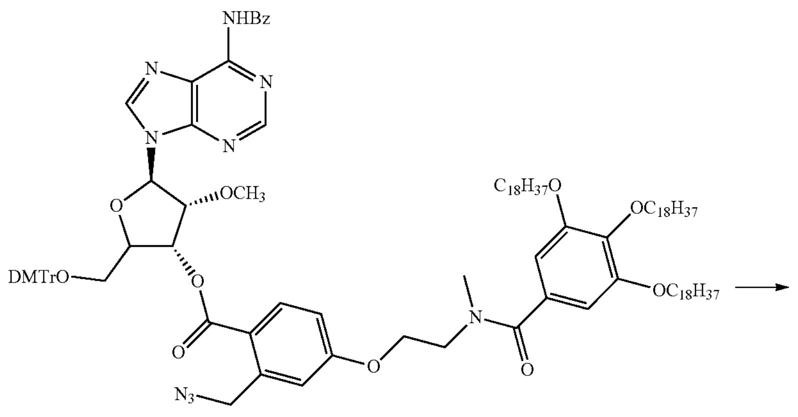
(5-VII)
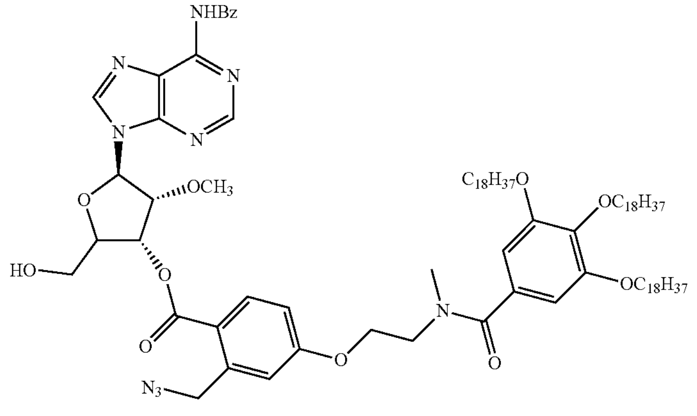
(5-VIII)

SCHEME 6
Cleavage for a monomer:
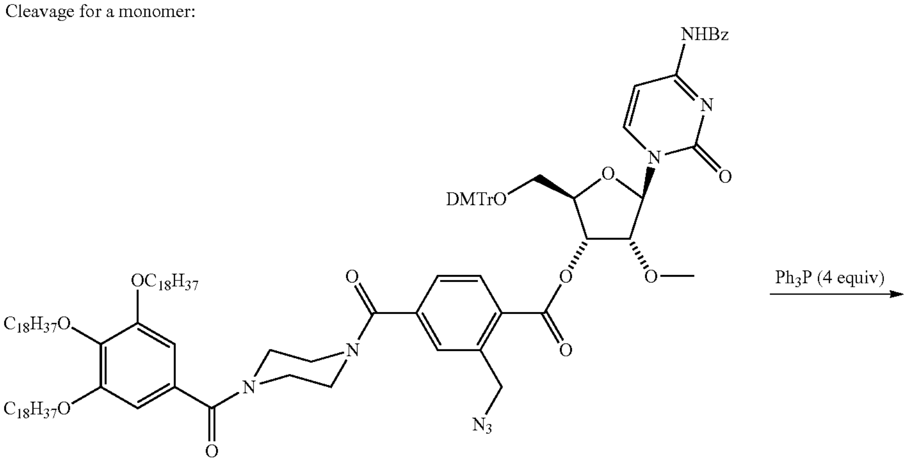
(6-I)
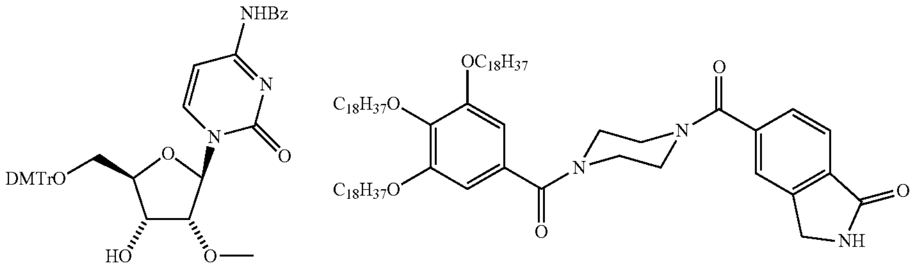
(6-II) (6-III)
Cleavage for a dimer:
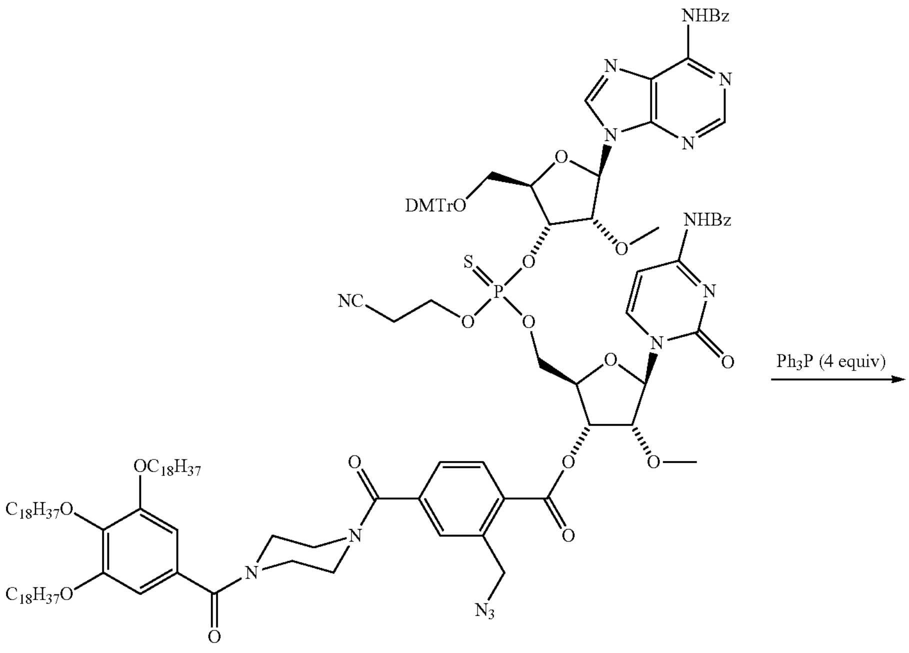
(6-IV-1)

-continued
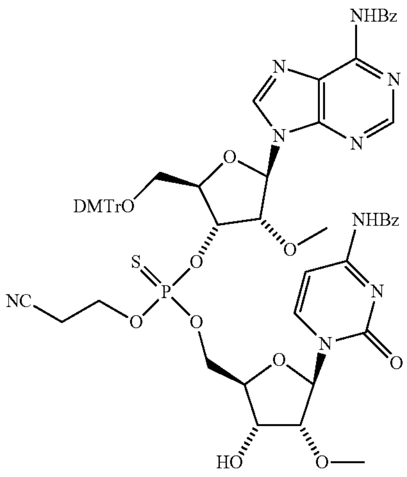
(6-V-1)
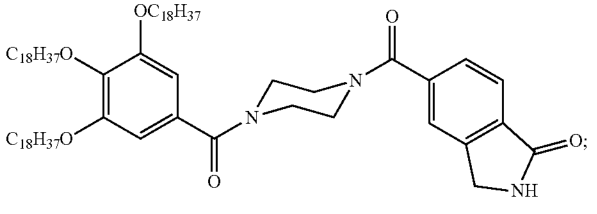
(6-III)
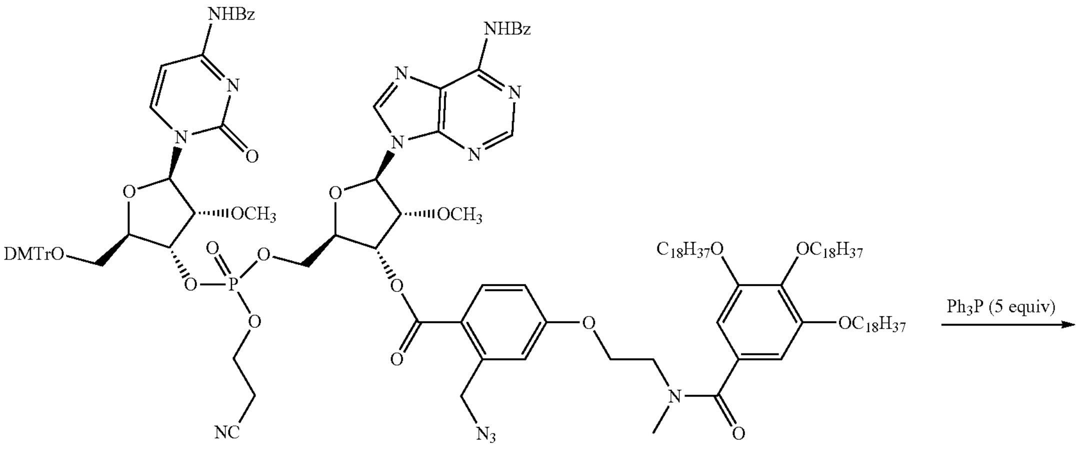
(6-IV-2)
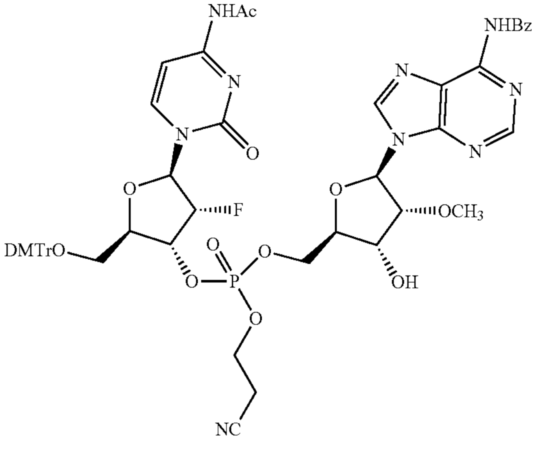
(6-V-2)
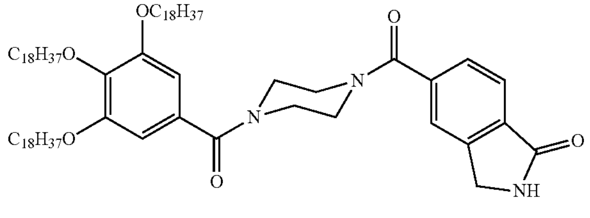
(6-III)

-continued
Cleavage for a tetramer:
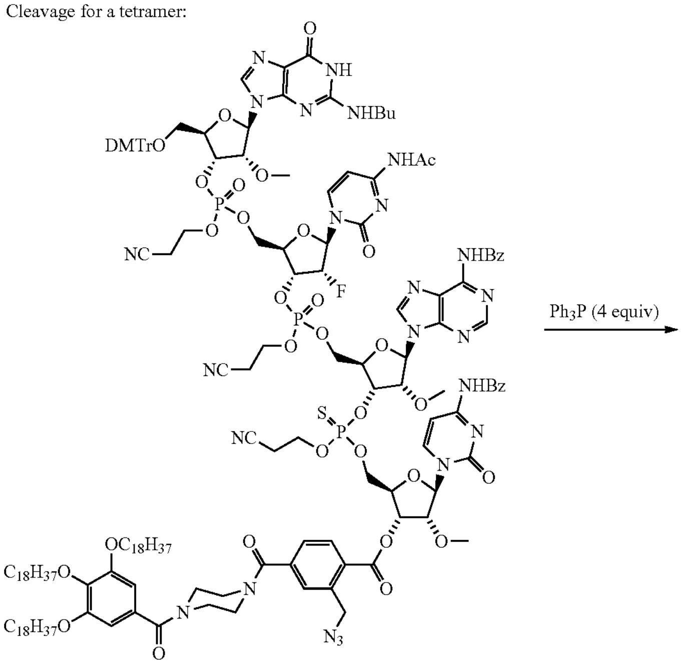
(6-VI)
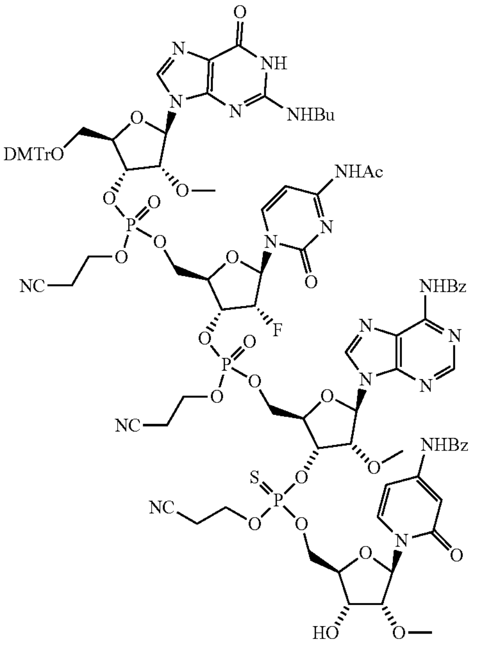
(6-VII)
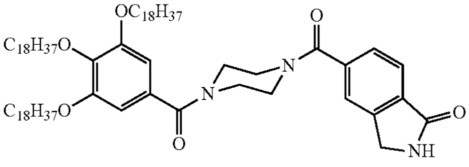
(6-III)

Example 1: 2-(azidomethyl)-4-(4-(3,4,5-tris(octadecyloxy)benzoyl)piperazine-1-carbonyl)benzoic acid

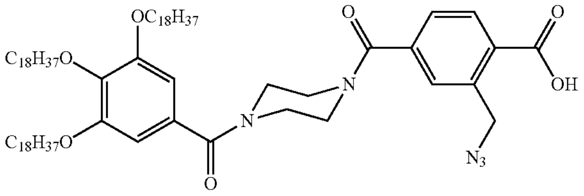

1. Synthesis of CMPD-001-2

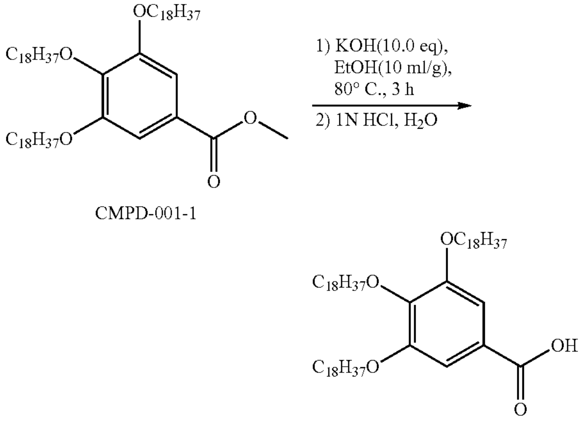

CMPD-001-1

CMPD-001-2

To a solution of CMPD-001-1 (39 g, 41 mmol, 1.0 eq.) in 390 mL of ethanol with an inert atmosphere of nitrogen was added potassium hydroxide (23 g, 414.5 mmol, 10.0 eq.) at room temperature. The resulting solution was stirred for 3 h at 80° C., and concentrated under reduced pressure. The pH value of the solution was adjusted to 1-2 with hydrochloric acid (1 mol/L) and the mixture stirred for 1 h at room temperature. The solids were collected by filtration and washed with acetonitrile, acetone and ethanol respectively. 29 g (76%) of CMPD-001-2 was obtained as a white solid. 1H NMR (300 MHz, Chloroform-d) δ 7.35 (s, 2H), 4.05 (m, 5H), 3.60-3.31 (m, 1H), 1.91-1.70 (m, 6H), 1.50 (m, 6H), 1.28 (s, 84H), 0.96-0.86 (m, 9H).

2. Synthesis of CMPD-002-2

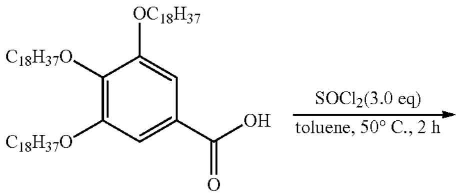

CMPD-001-2

-continued

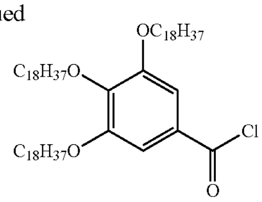

CMPD-002-2

To a solution of CMPD-001-2 (24 g, 25.9 mmol, 1.0 eq.) in 200 mL of toluene with an inert atmosphere of nitrogen, was added thionyl chloride (9 g, 0.77 mol, 3.0 eq.) at room temperature. The resulting solution was stirred for 2 h at 50° C. and concentrated under reduced pressure. 24 g (crude) of CMPD-002-2 was obtained as colorless oil. It was used at next step without further purification.

3. Synthesis of CMPD-002-3

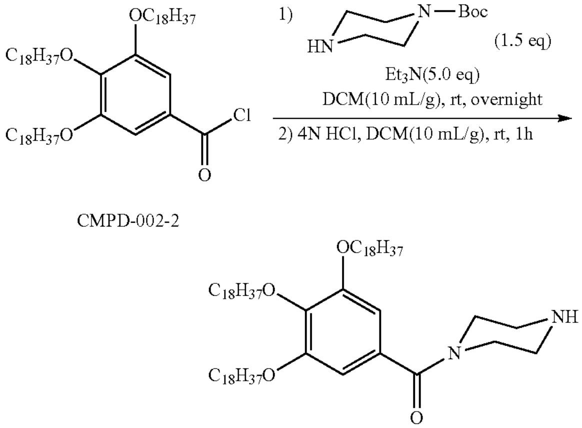

CMPD-002-2

CMPD-002-3

To a solution of CMPD-002-2 (24 g, 25.4 mmol, 1.00 eq.) in 240 mL of dichloromethane was added triethylamine (12.8 g, 127 mmol, 5.0 eq.) and tert-Butyl 1-piperazinecarboxylate (7.1 g, 38.1 mmol, 1.5 eq.) at room temperature. The resulting solution was stirred overnight at room temperature. The pH value of the solution was adjusted to 1-2 with hydrochloric acid (4 mol/L) and the mixture stirred for 1 h at room temperature. The resulting solution was precipitated by addition of acetonitrile. The solids were collected by filtration and washed with acetonitrile, acetone and methanol respectively. 15 g (68% over two steps) of CMPD-002-3 was obtained as a white solid. MS m/z $[M+H]^+$ (ESI): 982. $^1H$ NMR (300 MHz, Chloroform-d) δ 10.14 (s, 1H), 6.59 (s, 2H), 3.98 (m, 10H), 3.25 (s, 4H), 1.79 (m, 6H), 1.45-1.43 (m, 6H), 1.28 (m, 84H), 0.99-0.81 (m, 9H).

4. Synthesis of CMPD-003-21

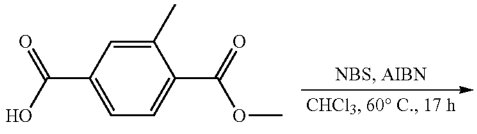

-continued

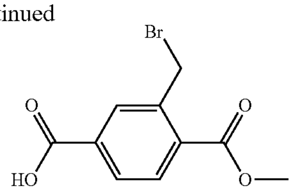

CMPD-003-21

To a solution of 4-(Methoxycarbonyl)-3-Methylbenzoic acid (6.00 g, 31 mmol, 1.0 eq) in 60 mL of chloroform was added N-Bromosuccinimide (6.05 g, 34 mmol, 1.10 eq.) and 2,2'-Azobis(2-methylpropionitrile) (3.05 g, 18.6 mmol, 0.6 eq.) at room temperature. The resulting solution was stirred for 2 h at 65° C. Then cooled to room temperature and concentrated under vacuum. The residue was purified by Flash-Prep-HPLC with the following conditions: Column, C18 silica gel; mobile phase, water (containing 0.05% HCOOH) and acetonitrile; Detector, UV 254 nm. The fractions were diluted with dichloromethane. The organic phase was dried over anhydrous sodium sulfate, filtered and concentrated under reduced pressure. 6 g (71%) CMPD-003-21 was obtained as an off-white solid. MS m/z $[M-H]^-$ (ESI): 271.

5. Synthesis of CMPD-003-22

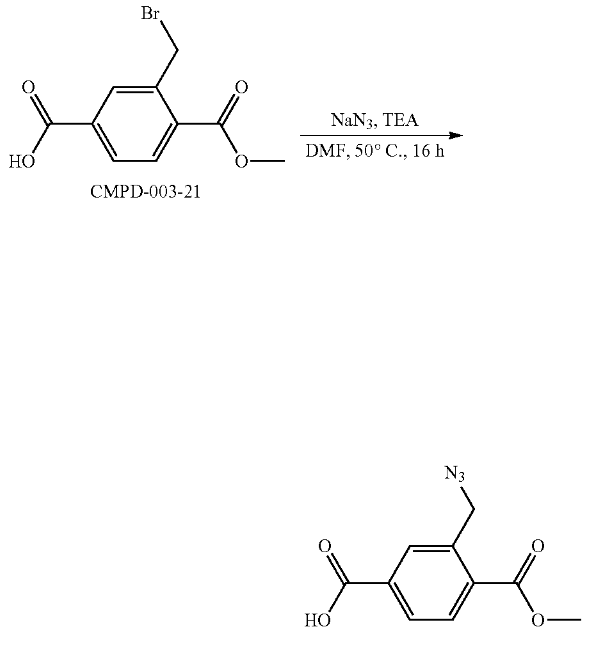

CMPD-003-21

CMPD-003-22

To a solution of CMPD-003-21 (6 g, 22.1 mmol, 1.0 eq.) in 60 mL of N, N-dimethylformamide with an inert atmosphere of nitrogen was added triethylamine (6.7 g, 66.3 mmol, 3.0 eq.) and sodium azide (2.87 g, 44.2 mmol, 2.0 eq.) sequentially at room temperature. The reaction solution was stirred for 2 h at 70° C., and concentrated. The residue was purified by Flash-Prep-HPLC with the following conditions: Column, C18 silica gel; mobile phase, water (containing 0.05% HCOOH) and acetonitrile (5% acetonitrile up to 50% in 15 min; Detector, UV 254 nm. The fractions were diluted with dichloromethane. The organic phase was dried over anhydrous sodium sulfate, filtered and concentrated under reduced pressure. 4.2 g (82%) CMPD-003-22 was obtained as an off-white solid. MS m/z $[M-H]^-$ (ESI): 234. 1H NMR (300 MHz, DMSO-d6) δ 13.42 (s, 1H), 8.09 (s, 1H), 8.01 (s, 2H), 4.86 (s, 2H), 3.89 (s, 3H).

6. Synthesis of CMPD-003-3

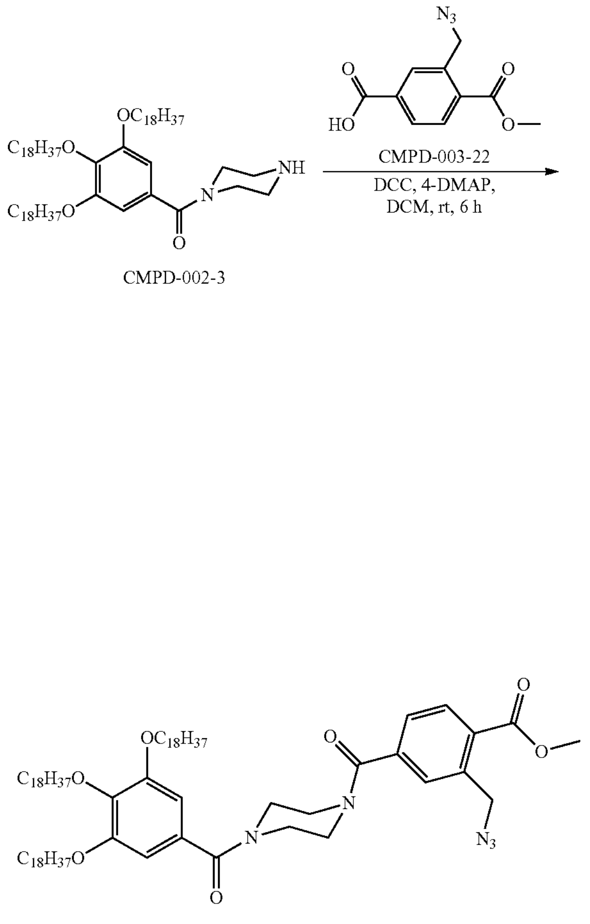

CMPD-002-3

CMPD-003-3

To a solution of CMPD-002-3 (14.8 g, 14.9 mmol, 1.0 eq) in 150 mL of dichloromethane with an inert atmosphere of nitrogen were added CMPD-003-22 (4.2 g, 17.8 mmol, 1.2 eq.), 4-dimethylaminopyridine (3.66 g, 30.0 mmol, 2.0 eq.) and dicyclohexylcarbodiimide (6.0 g, 30.0 mmol, 2.0 eq.) sequentially at room temperature. The resulting solution was stirred for 6 hours at room temperature. The resulting solution was precipitated by addition of acetonitrile. The solids were collected by filtration and washed with ethanol, acetonitrile respectively. 9.0 g (60%) of CMPD-003-3 was obtained as a white solid. MS m/z $[M+H]^+$ (ESI): 1213. 1H NMR (300 MHz, Chloroform-d) δ 8.09 (d, J=8.0 Hz, 1H), 7.58 (s, 1H), 7.44 (d, J=8.0 Hz, 1H), 6.60 (s, 2H), 4.89 (s, 2H), 4.00-3.93 (m, 8H), 3.70 (m, 5H), 3.53-3.39 (m, 2H), 1.86-1.66 (m, 8H), 1.46 (m, 6H), 1.27 (m, 84H), 0.89 (m, 9H).

7. Synthesis of CMPD-003-0

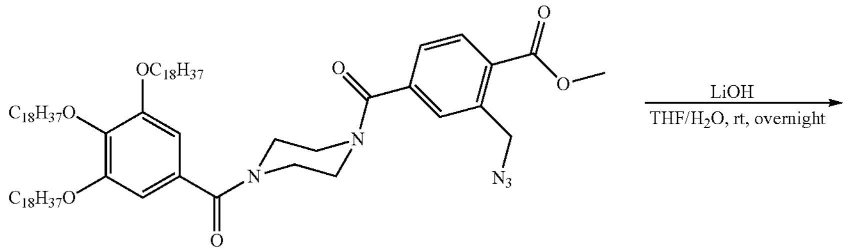

CMPD-003-3

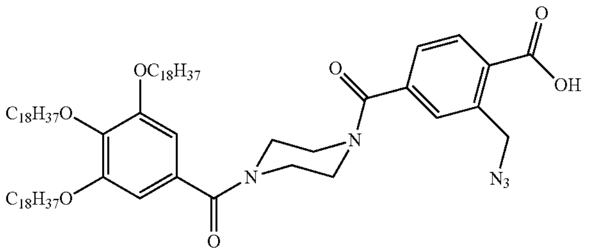

CMPD-003-0

To a solution of CMPD-003-0 (9 g, 7.4 mmol, 1.0 eq.) in 90 mL of tetrahydrofuran/water (5:1) with an inert atmosphere of nitrogen was added lithium hydroxide (7.12 g, 29.7 mmol, 4.0 eq.) at room temperature. The resulting solution was stirred overnight at room temperature. The resulting solution was precipitated by addition of acetonitrile. The pH value of the solution was adjusted to 2 with hydrochloric acid (1 mol/L) and the mixture stirred for 1 h at room temperature. The solids were collected by filtration and washed with water, acetonitrile and acetonitrile respectively. The solids were dried under vacuum at 40° C. for 24 h. 7.5 g (84%) of CMPD-003-0 were obtained as a white solid. MS m/z $[M-H]^-$ (ESI): 1197 $^1H$ NMR (300 MHz, Chloroform-d) δ 7.87 (s, 1H), 7.28 (s, 2H), 6.61 (s, 2H), 4.58 (s, 1H), 4.08-3.86 (m, 6H), 3.54 (d, J=61.9 Hz, 6H), 2.09 (d, J=37.9 Hz, 3H), 1.79 (d, J=12.1 Hz, 7H), 1.44 (s, 6H), 1.40-1.18 (m, 84H), 0.95-0.86 (m, 9H).

Example 2: 2-(azidomethyl)-4-(2-(N-methyl-3,4,5-tris(octadecyloxy)benzamido)ethoxy)benzoic acid

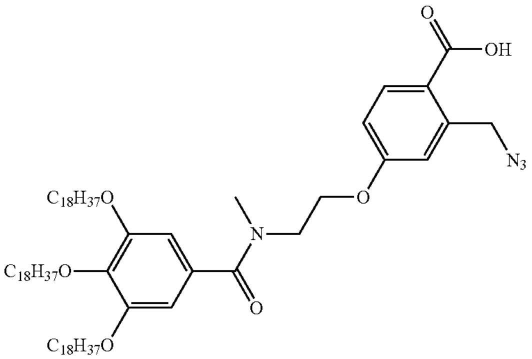

Step A. N-(2-hydroxyethyl)-N-methyl-3,4,5-tris(octadecyloxy)benzamide

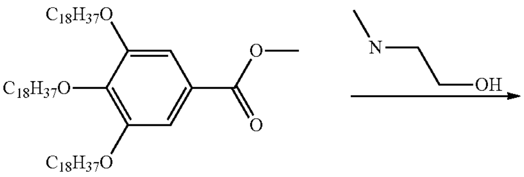

(I)

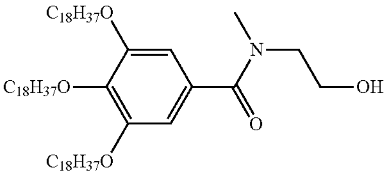

(II)

To I (5.0 g) was added N-Methylethanolamine (60 mL), and the resulting mixture was stirred at 130° C. over the weekend. NMR analysis showed less than half completion, and the reaction temperature was elevated to reflux (180° C. bath). The reaction was then cooled to r.t. and DCM (150 mL) was added, and the mixture was stirred at r.t. The solid, the recovered I, was collected by filtration, and the mother liqor was precipitated by addition of MeOH. The solid was collected and washed with methanol to give 3.4 g of II of 90% NMR purity.

Step B. Methyl 2-methyl-4-(2-(N-methyl-3,4,5-tris(octadecyloxy)benzamido)ethoxy)benzoate

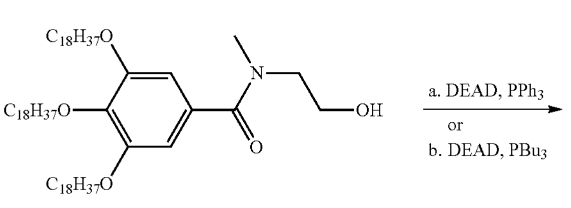

(II)

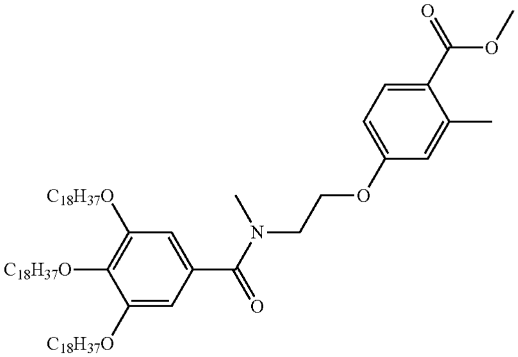

(III)

To II (1.0 g), phenol (0.36 mL) and TPP (0.53 g) dissolved in DCM (10 mL) and stirred at 0° C., was added 40% wt DEAD in toluene (0.93 mL), and the resulting mixture was stirred rt overnight. The reaction mixture was separated by silica gel column chromatograph (EtOAc/hexane, 0-30%) to give 0.31 g of III.

Alternatively, to II (0.5 g), phenol (0.17 g) and TBP (0.25 mL) dissolved in DCM (5 mL) and stirred at 0° C., was added 40% wt DEAD in toluene (0.46 mL), and the resulting mixture was stirred rt overnight. The product was precipitated out by addition of MeOH. The solid was collected and washed with methanol to give 0.25 g of III.

Step C. methyl 2-(bromomethyl)-4-(2-(N-methyl-3,4,5-tris(octadecyloxy)benzamido)ethoxy)benzoate

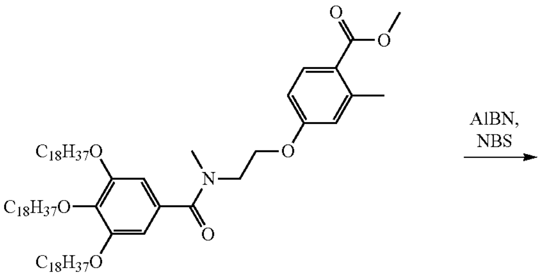

(III)

-continued

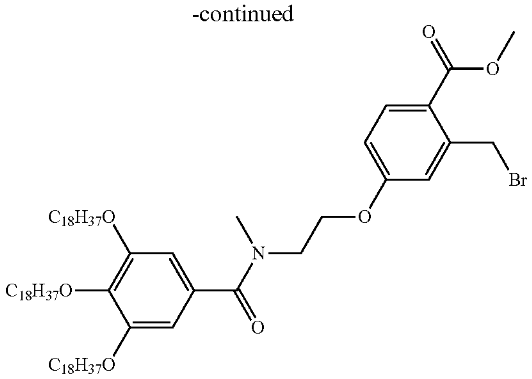

(IV)

To III (0.58 g) and NBS (0.1 g) dissolved in $CCl_4$ (4 mL) was added AIBN (0.05 g), and the reaction was stirred at 65° C. for 3 h. TLC showed nearly completed reaction. To the reaction was added $CH_3CN$ (15 mL), and the mixture was stirred for 15 min. The solid was collected and separated by silica gel column chromatograph (EtOAc/hexane, 0-30%) to give 0.24 g of product IV.

Step D. methyl 2-(azidomethyl)-4-(2-(N-methyl-3,4,5-tris(octadecyloxy)benzamido)ethoxy)benzoate

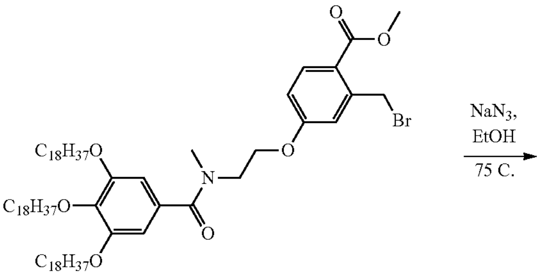

(IV)

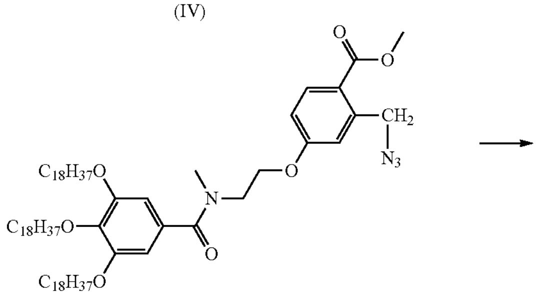

(V)

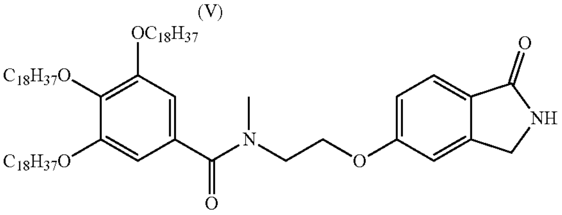

(VI)

A mixture of IV (0.31 g) and $NaN_3$ (83 mg) in ethanol (3 mL) was stirred at 70° C. overnight. The reaction was cooled to rt, and methanol (10 mL) was added. The precipitated solid was collected by filtration and washed with water (3 mL) and methanol to give 0.19 g of crude product V, and a small sample of V was treated with $PhP_3$—$H_2O$ to form VI, which supports the assigned structure.

Step E. 2-(azidomethyl)-4-(2-(N-methyl-3,4,5-tris(octadecyloxy)benzamido)ethoxy)benzoic acid

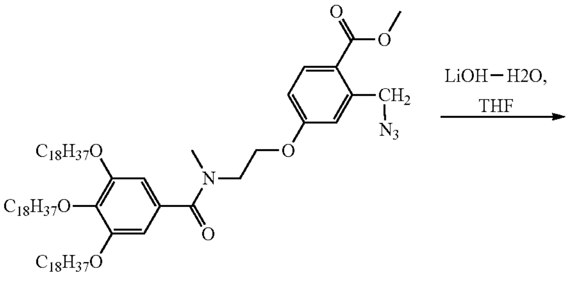

(V)

-continued

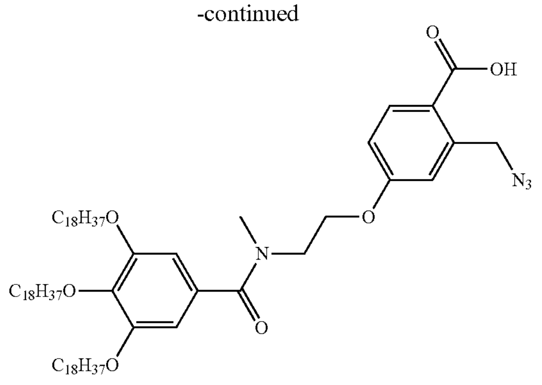

(VI)

To V (0.19 g) in THE (5 mL) was added 1 M LiOH (1.62 mL), and the reaction was stirred at rt overnight. Volatiles were evaporated, and the residue was dissolved in a limited amount of DCM, and MeOH was added, and the precipitated solid was collected by filtration, and washed with 0.1 N HCl (3 mL) and methanol to give the product, 44 mg.

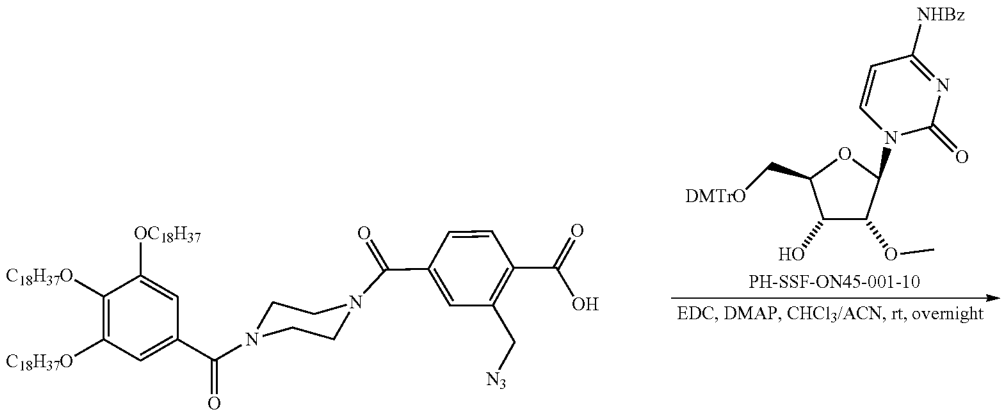

I

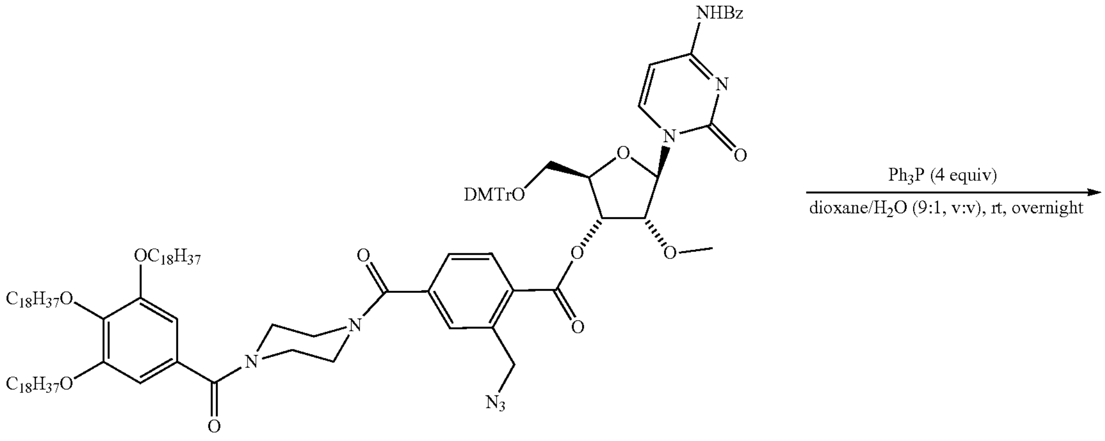

II

-continued
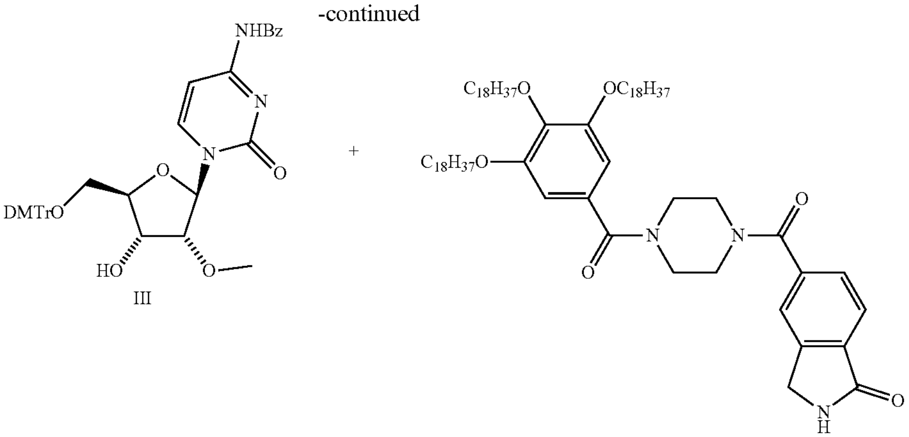
III
IV
Example 3: Mild Cleavage of Soluble Support and the Formation of 5-(4-(3,4,5-tris(octadecyloxy)benzoyl)piperazine-1-carbonyl)isoindolin-1-one
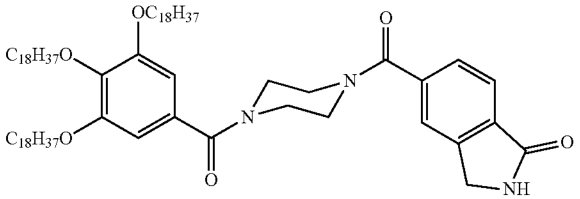
Step A. (2R,3R,4R,5R)-5-(4-benzamido-2-oxopyrimidin-1(2H)-yl)-2-((bis(4-methoxyphenyl)(phenyl)methoxy)methyl)-4-methoxytetrahydrofuran-3-yl 2-(azidomethyl)-4-(4-(3,4,5-tris(octadecyloxy)benzoyl)piperazine-1-carbonyl)benzoate
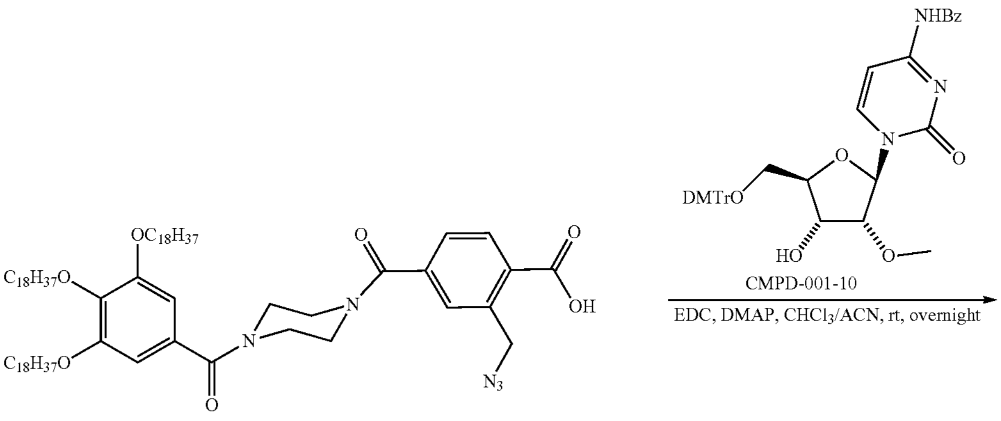
CMPD-003-0

-continued

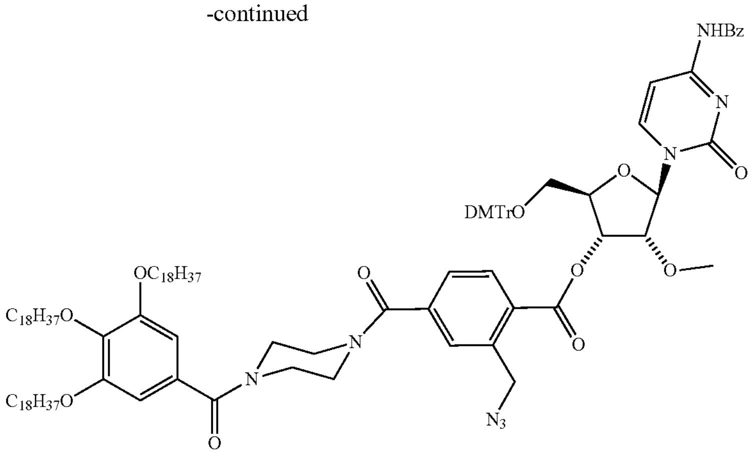

CMPD-003-100

To a solution of CMPD-003-0 (500 mg, 0.42 mmol, 1.0 eq.) in 5 mL of chloroform/acetonitrile (10/1, v/v) with an inert atmosphere of Ar, was added CMPD-001-10 (553 mg, 0.84 mmol, 2.0 eq.), 1-(3-Dimethylaminopropyl)-3-ethyl-carbodiimide hydrochloride (120 mg, 0.63 mmol, 1.5 eq.) and 4-Dimethylaminopyridine (77 mg, 0.63 mmol, 1.5 eq.) sequentially at room temperature. The resulting solution was stirred overnight at room temperature. The resulting solution was precipitated by addition of acetonitrile, and the solid was collected by filtration. 400 mg (70% yield) of CMPD-003-100 was obtained as a white solid. MS m/z $[M-H]^-$ (ESI): 1843.

Step B. 5-(4-(3,4,5-tris(octadecyloxy)benzoyl)piperazine-1-carbonyl)isoindolin-1-one

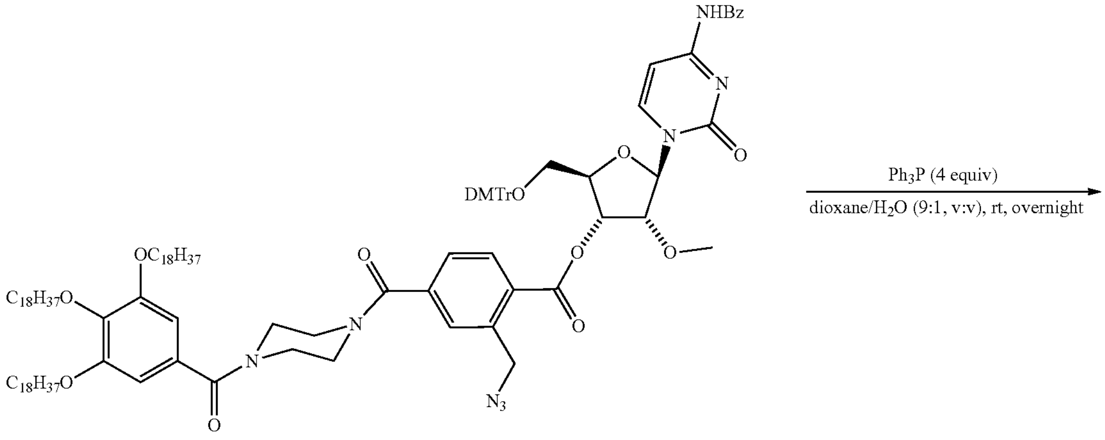

CMPD-003-100

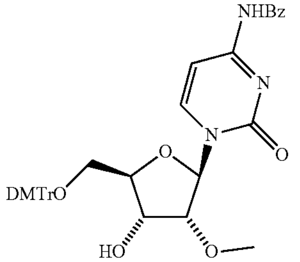

CMPD-001-10

+

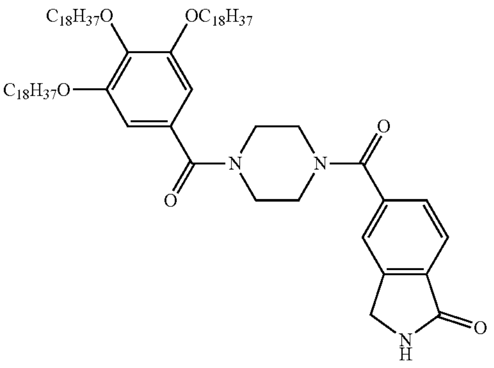

Removed piece

To a solution of CMPD-003-100 (100 mg, 0.05 mmol, 1.0 eq.) in 1 mL of dioxane/water (9/1, v/v) with an inert atmosphere of Ar was added triphenylphosphine (57 mg, 0.2 mmol, 4.0 eq.) at room temperature. The reaction solution was stirred overnight at room temperature. The resulting solution was precipitated by addition of acetonitrile, and the solid was collected by filtration. The solids were washed with acetonitrile, acetone and methanol respectively. 50 mg (80% yield) of Removed piece were obtained as an off-white solid. MS m/z $[M+H]^+$ (ESI): 1155. $^1H$ NMR (300 MHz, Chloroform-d) δ 7.96 (d, J=7.7 Hz, 1H), 7.58 (s, 1H), 7.52 (d, J=7.9 Hz, 1H), 6.62 (m, 3H), 4.52 (s, 2H), 3.98 (m, 6H), 3.68 (m, 8H), 1.83-1.76 (m, 6H), 1.50-1.44 (m, 6H), 1.28 (m, 84H), 0.89 (m, 9H).

Example 4: Mild Cleavage of Soluble Support and the Formation of O-(((2R,3R,4R,5R)-5-(4-benzamido-2-oxopyrimidin-1(2H)-yl)-3-hydroxy-4-methoxytetrahydrofuran-2-yl)methyl) 0-((2R,3R,4R,5R)-5-(6-benzamido-9H-purin-9-yl)-2-((bis(4-methoxyphenyl)(phenyl)methoxy)methyl)-4-methoxytetrahydrofuran-3-yl) 0-(2-cyanoethyl) phosphorothioate

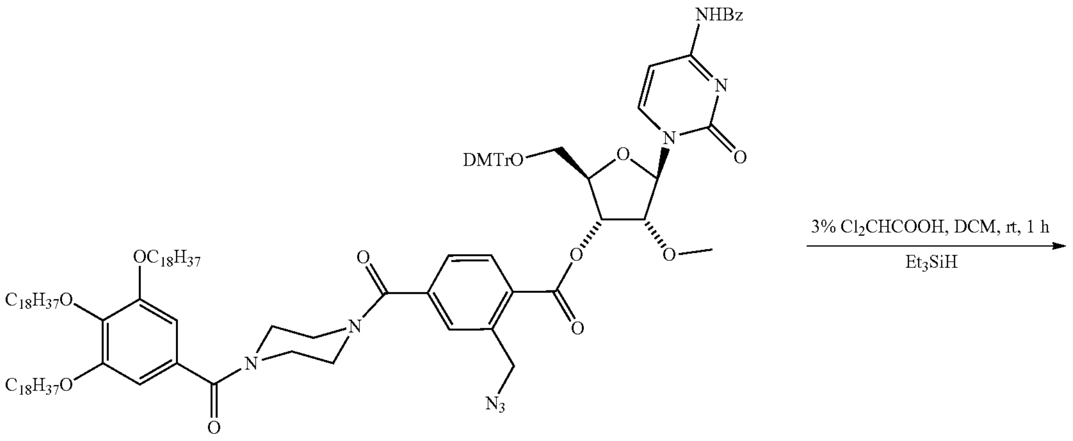

I

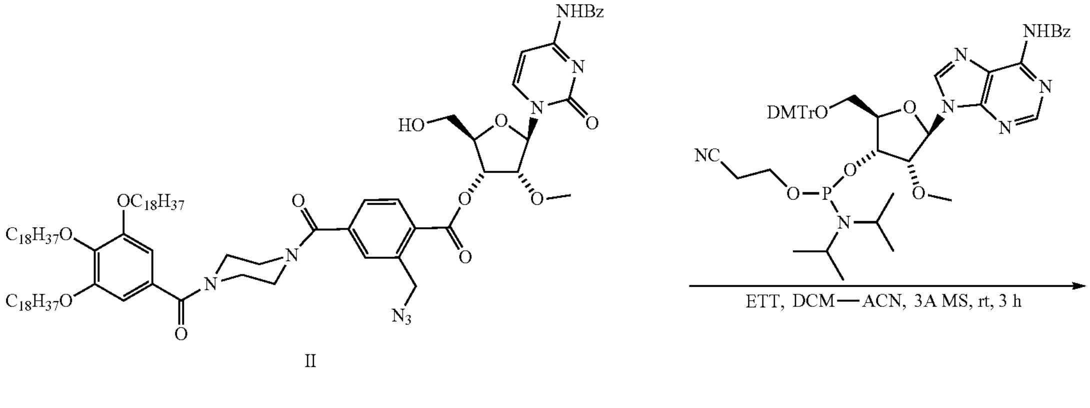

II

-continued
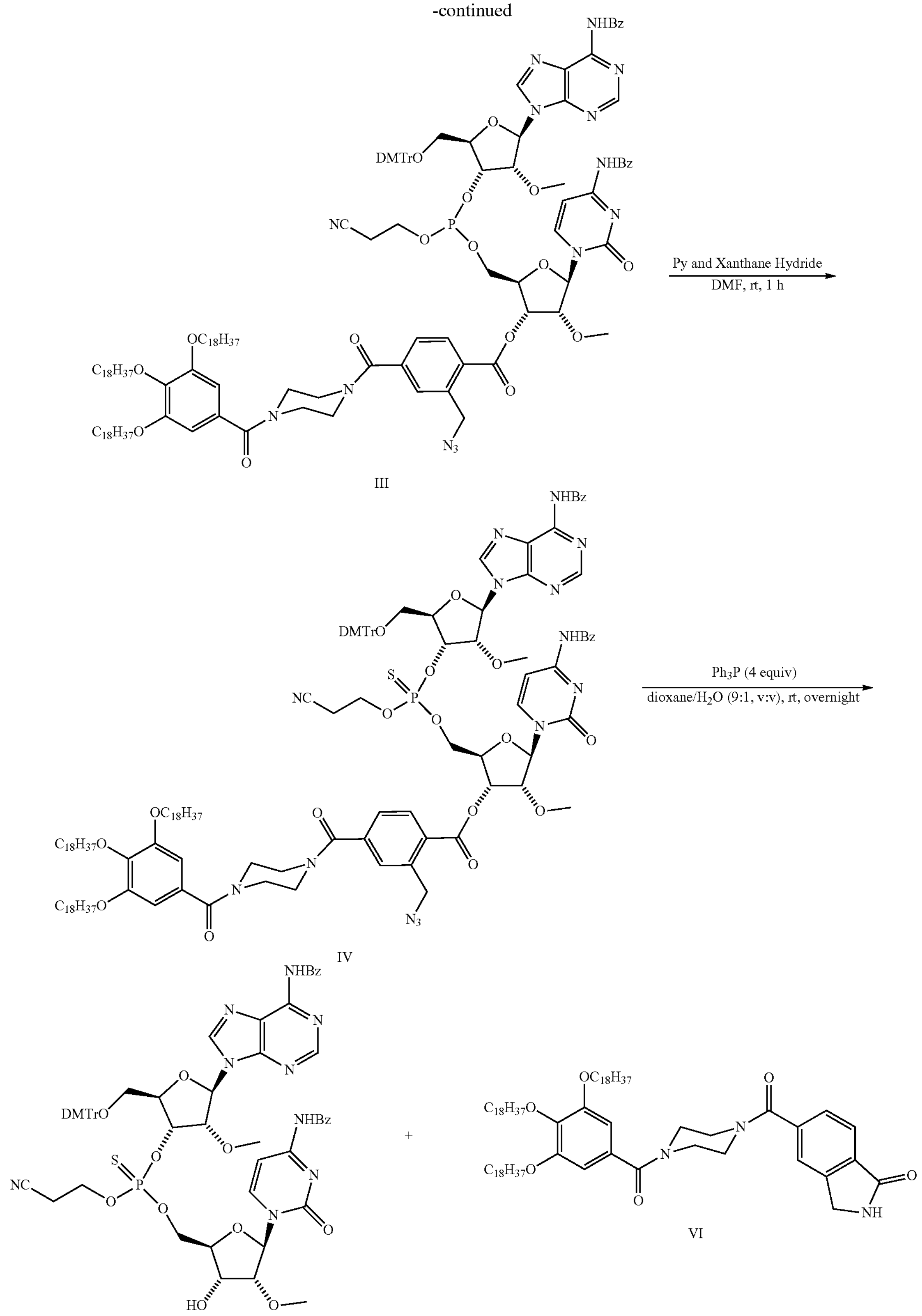
III
IV
V
VI

Step A. (2R,3R,4R,5R)-5-(4-benzamido-2-oxopyrimidin-1(2H)-yl)-2-(hydroxymethyl)-4-methoxytetrahydrofuran-3-yl 2-(azidomethyl)-4-(4-(3,4,5-tris(octadecyloxy)benzoyl)piperazine-1-carbonyl)benzoate

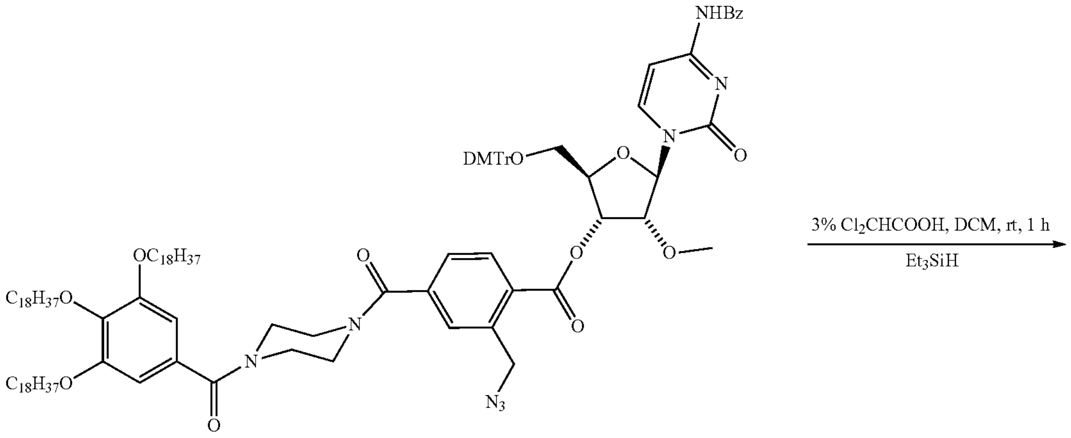

CMPD-003-100

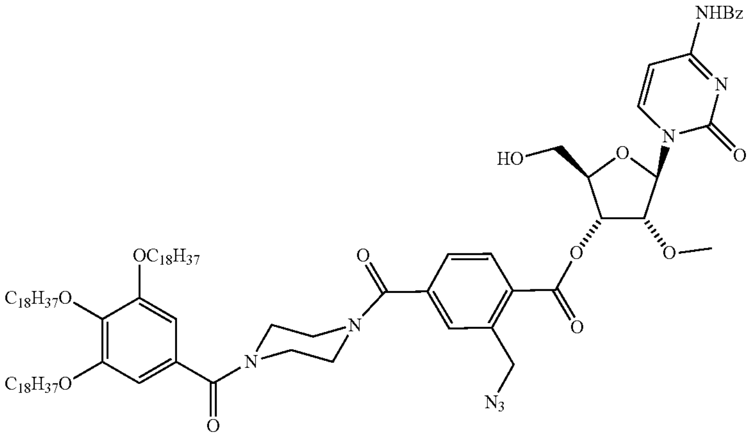

CMPD-003-101

To a solution of CMPD-003-100 (200 mg, 0.11 mmol, 1.0 eq) in 2 mL of dichloromethane was added 0.12 mL of dichloroacetic acid. The resulting solution was stirred for 1 h at 25° C. The resulting solution was precipitated by addition of acetonitrile, and the solid was collected by filtration. 150 mg (90%) of CMPD-003-101 was obtained as an off-white solid. MS m/z $[M+H]^+$ (ESI): 1543.

Step B. (2R,3R,4R,5R)-5-(4-benzamido-2-oxopyrimidin-1(2H)-yl)-2-((((((2R,3R,4R,5R)-5-(6-benzamido-9H-purin-9-yl)-2-((bis(4-methoxyphenyl)(phenyl)methoxy)methyl)-4-methoxytetrahydrofuran-3-yl)oxy)(2-cyanoethoxy)phosphaneyl)oxy)methyl)-4-methoxytetrahydrofuran-3-yl 2-(azidomethyl)-4-(4-(3,4,5-tris(octadecyloxy)benzoyl)piperazine-1-carbonyl)benzoate

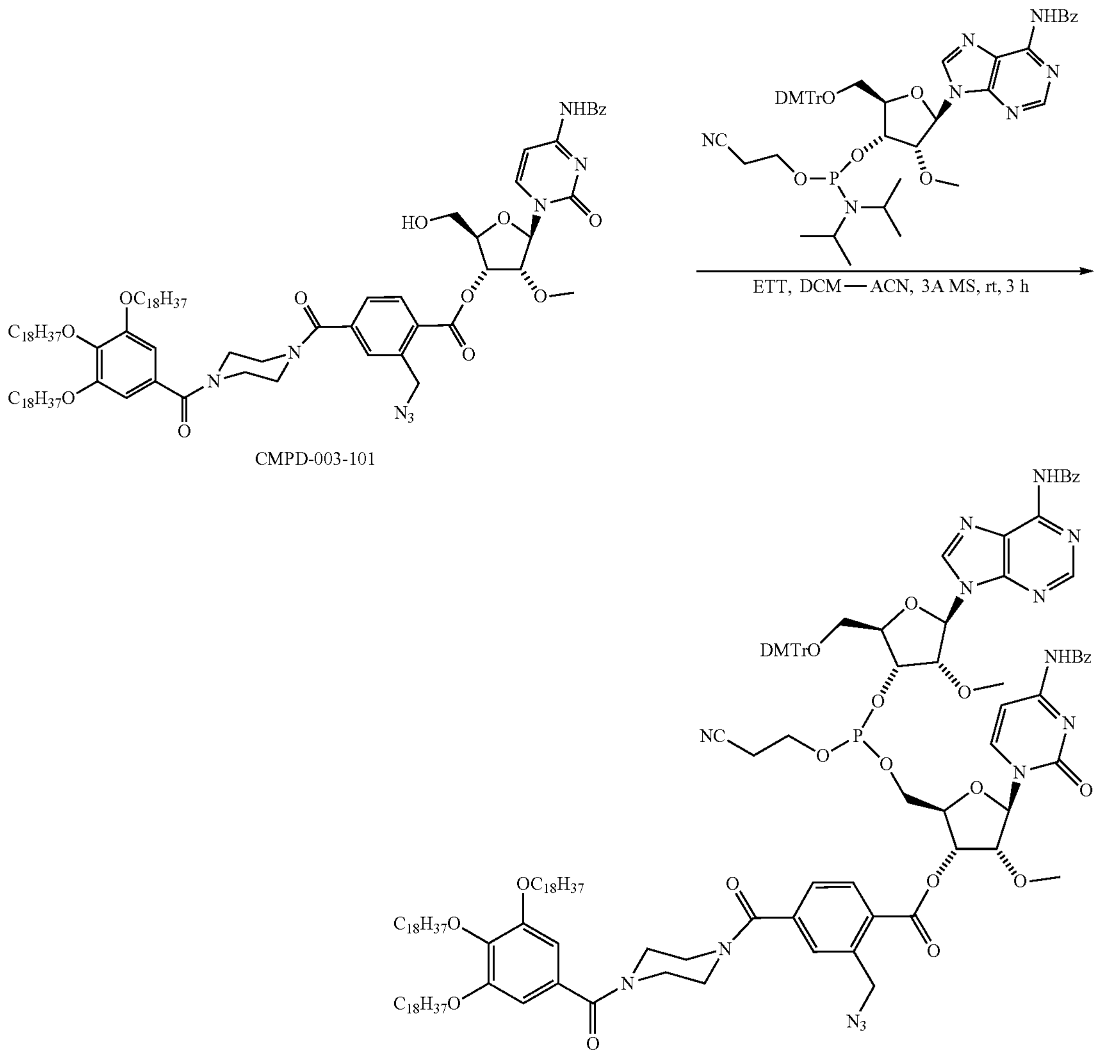

CMPD-003-101

CMPD-003-102

CMPD-003-101 was dried by repeated co-evaporations with dry pyridine and dry toluene. To a solution of CMPD-003-101 (150 mg, 0.1 mmol, 1.0 eq.) in 1.5 mL of dichloromethane with an inert atmosphere of Ar and 3A molecular sieves was added (2R,3R,4R,5R)-5-(6-benzamido-9H-purin-9-yl)-2-((bis(4-methoxyphenyl)(phenyl)methoxy)methyl)-4-methoxytetrahydrofuran-3-yl (2-cyanoethyl) diisopropylphosphoramidite (133 mg, 0.15 mmol, 1.5 eq.) and 5-(Ethylthio)-1H-tetrazole (39 mg, 0.3 mmol, 3.0 eq.) in 0.1 mL of acetonitrile sequentially at room temperature. The resulting solution was stirred for 1.5 h at room temperature and used for next step without further purification.

Step C. (2R,3R,4R,5R)-5-(4-benzamido-2-oxopyrimidin-1(2H)-yl)-2-((((((2R,3R,4R,5R)-5-(6-benzamido-9H-purin-9-yl)-2-((bis(4-methoxyphenyl)(phenyl)methoxy)methyl)-4-methoxytetrahydrofuran-3-yl)oxy)(2-cyanoethoxy)phosphorothioyl)oxy)methyl)-4-methoxytetrahydrofuran-3-yl 2-(azidomethyl)-4-(4-(3,4,5-tris(octadecyloxy)benzoyl)piperazine-1-carbonyl)benzoate

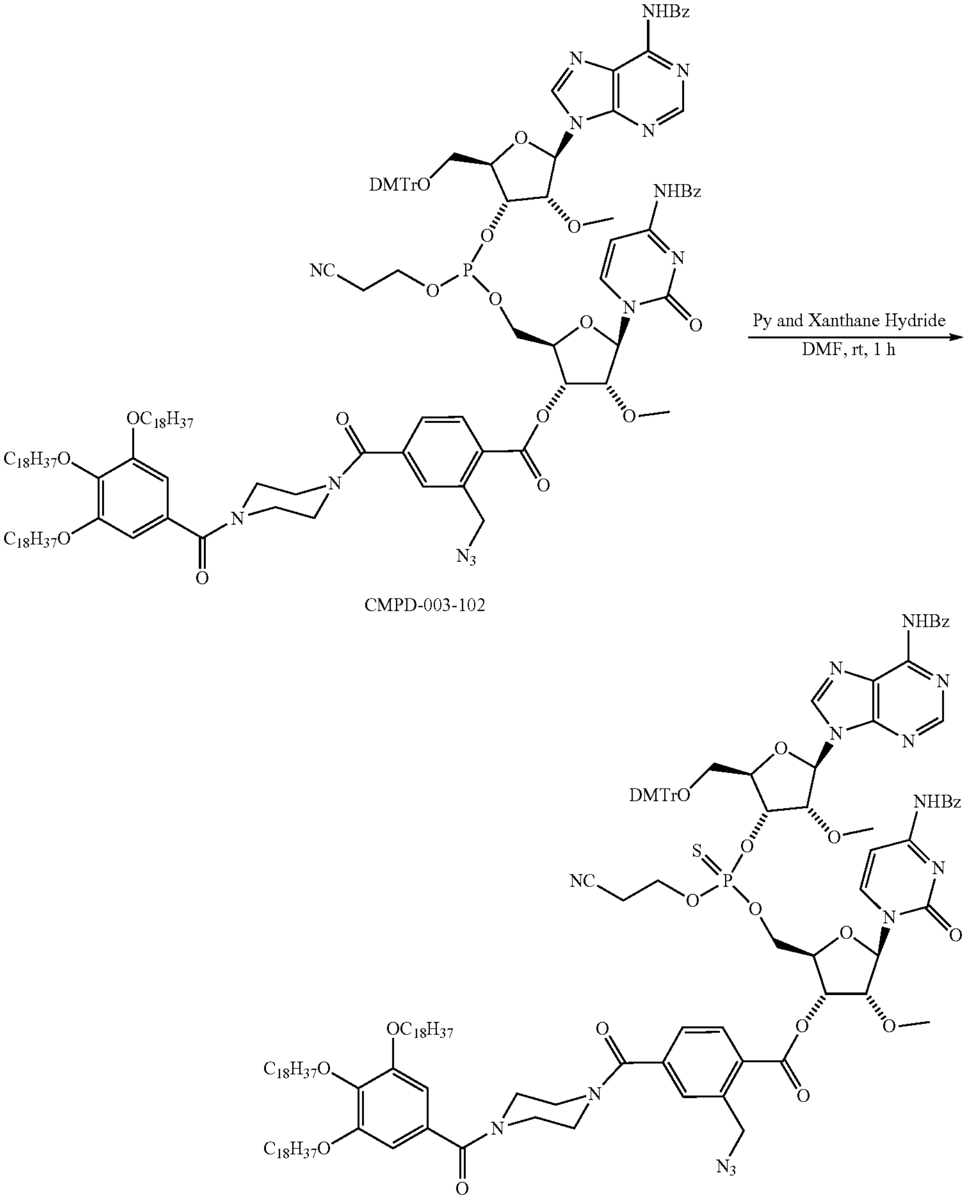

CMPD-003-102

CMPD-003-103

To the resulting solution of CMPD-003-102 (0.1 mmol, 1.0 eq.) with an inert atmosphere of Ar and 3A molecular sieves were added pyridine (80 mg, 1.0 mmol, 10.0 eq.) and Xanthane Hydride (75 mg, 0.5 mmol, 5.0 eq.) sequentially at room temperature. The resulting solution was stirred for 1.5 h at room temperature. The resulting solution was filtrated and precipitated by addition of acetonitrile, and the solid was collected by filtration. 206 mg (over two steps of 90%) of CMPD-003-103 were obtained as a white solid. MS m/z $[M/2+H]^+$ (ESI): 1180.

Step D. O-(((2R,3R,4R,5R)-5-(4-benzamido-2-oxopyrimidin-1(2H)-yl)-3-hydroxy-4-methoxytetrahydrofuran-2-yl)methyl)O-((2R,3R,4R,5R)-5-(6-benzamido-9H-purin-9-yl)-2-((bis(4-methoxyphenyl)(phenyl)methoxy)methyl)-4-methoxytetrahydrofuran-3-yl) 0-(2-cyanoethyl) phosphorothioate and 5-(4-(3,4,5-tris(octadecyloxy) benzoyl)piperazine-1-carbonyl)isoindolin-1-one

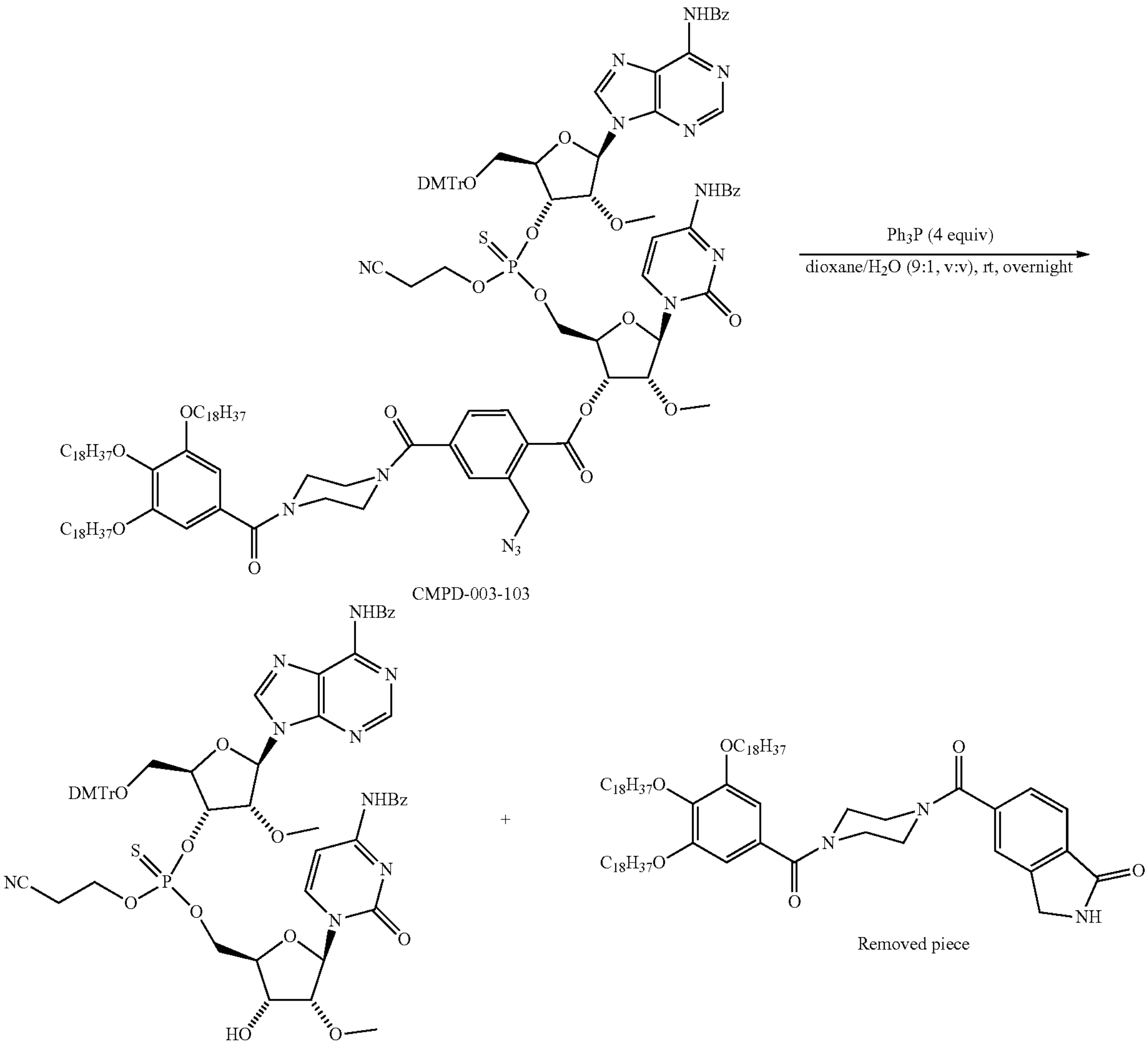

CMPD-003-103

CMPD-003-104

Removed piece

To a solution of CMPD-003-103 (100 mg, 0.05 mmol, 1.0 eq.) in 1 mL of dioxane/water (9/1, v/v) with an inert atmosphere of Ar, was added triphenylphosphine (57 mg, 0.2 mmol, 4.0 eq.) at room temperature. The reaction solution was stirred overnight at room temperature. The resulting solution was precipitated by addition of acetonitrile, and the solid was collected by filtration. The solids were washed with acetonitrile, acetone and methanol respectively. 40 mg (80%) of Removed piece were obtained as an off-white solid. MS m/z $[M+H]^+$ (ESI): 1155.

Cleavage of CMPD-003-120 (6-IV-2) off the soluble support was accomplished in a similar way to cleavage of CMPD-003-103.

Example 5: Fully Protected GCAC-CSS
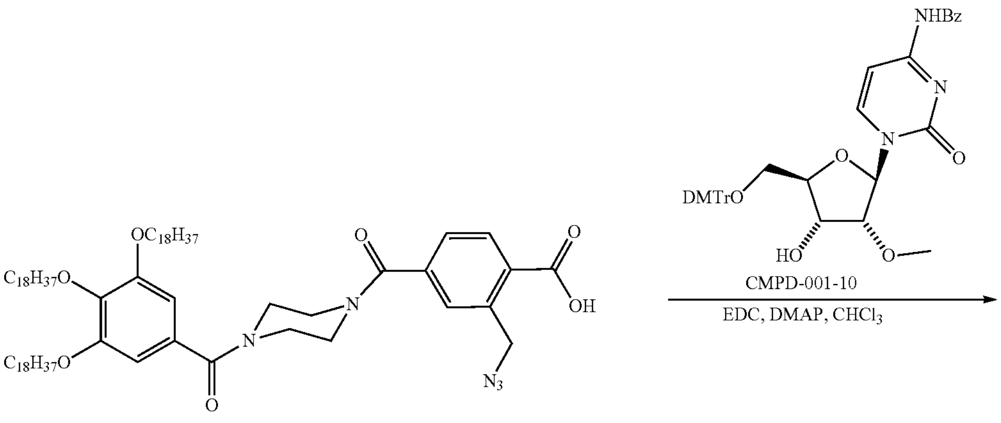
CMPD-003-0
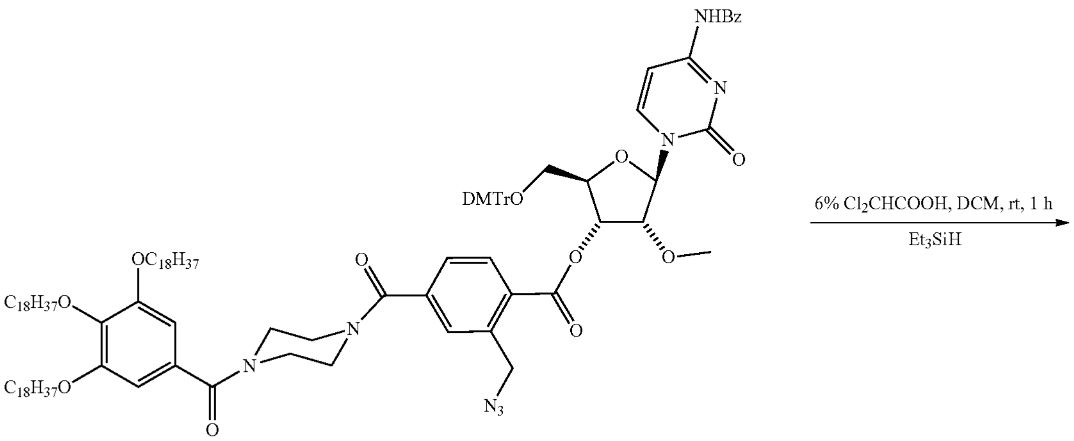
CMPD-003-100
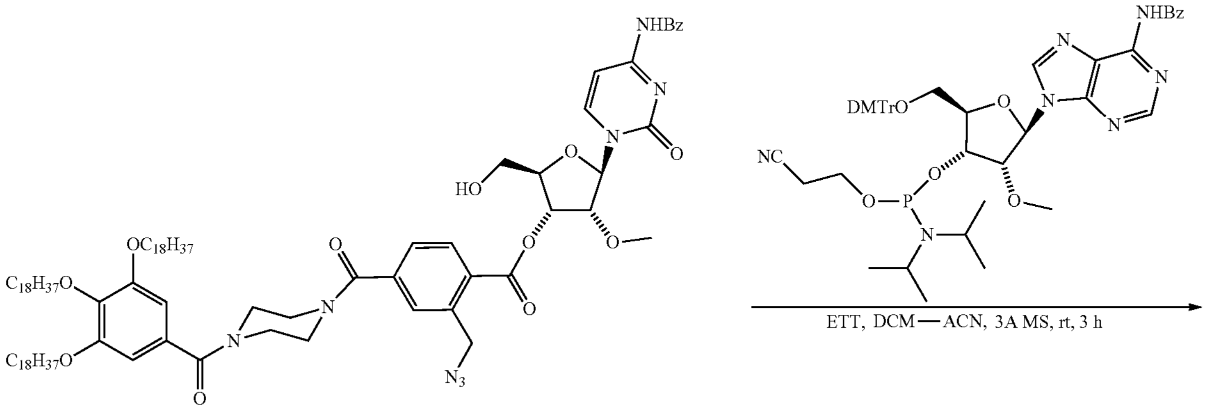
CMPD-003-101

-continued
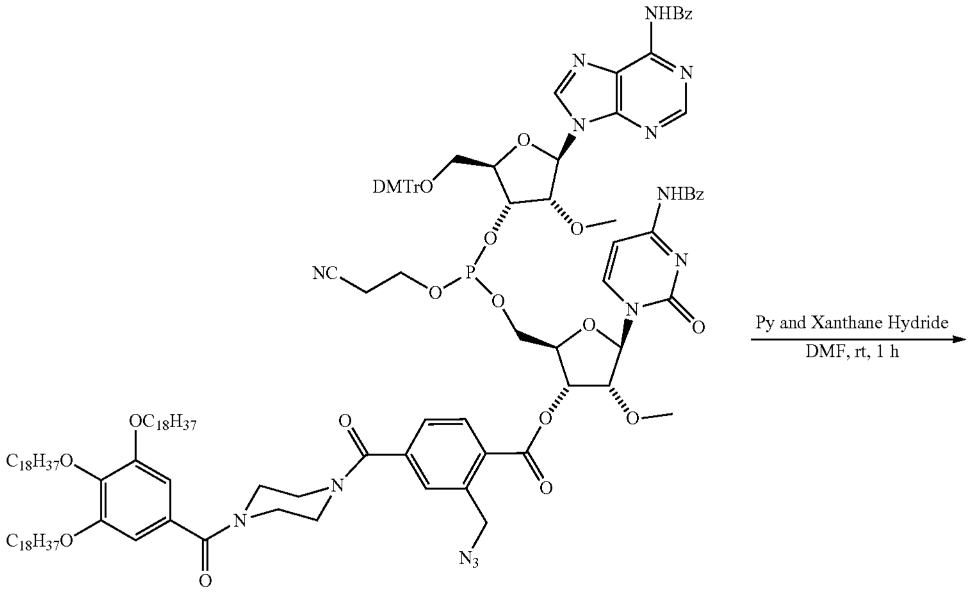
CMPD-003-102
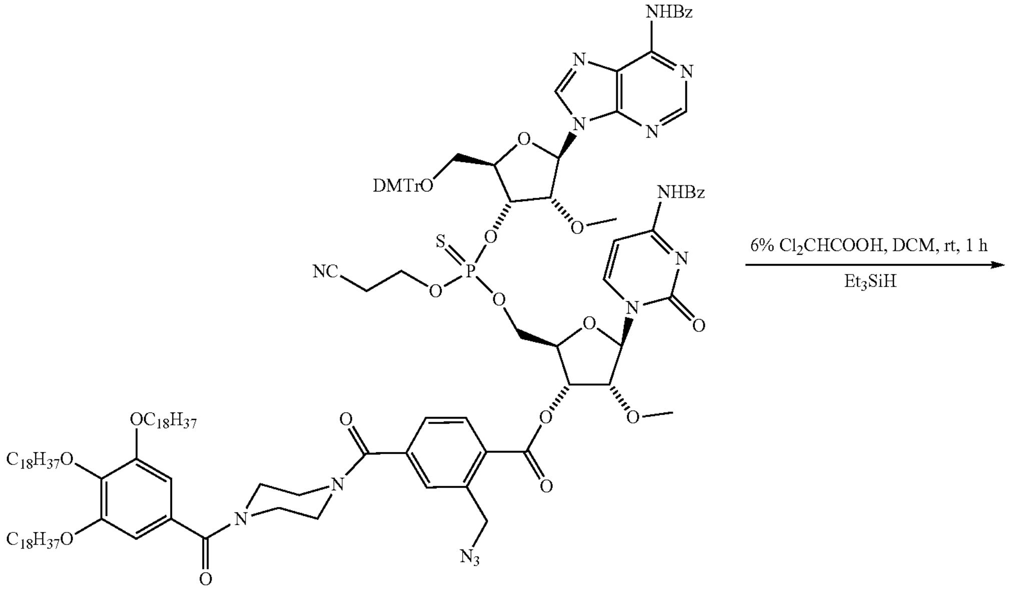
CMPD-003-103

-continued
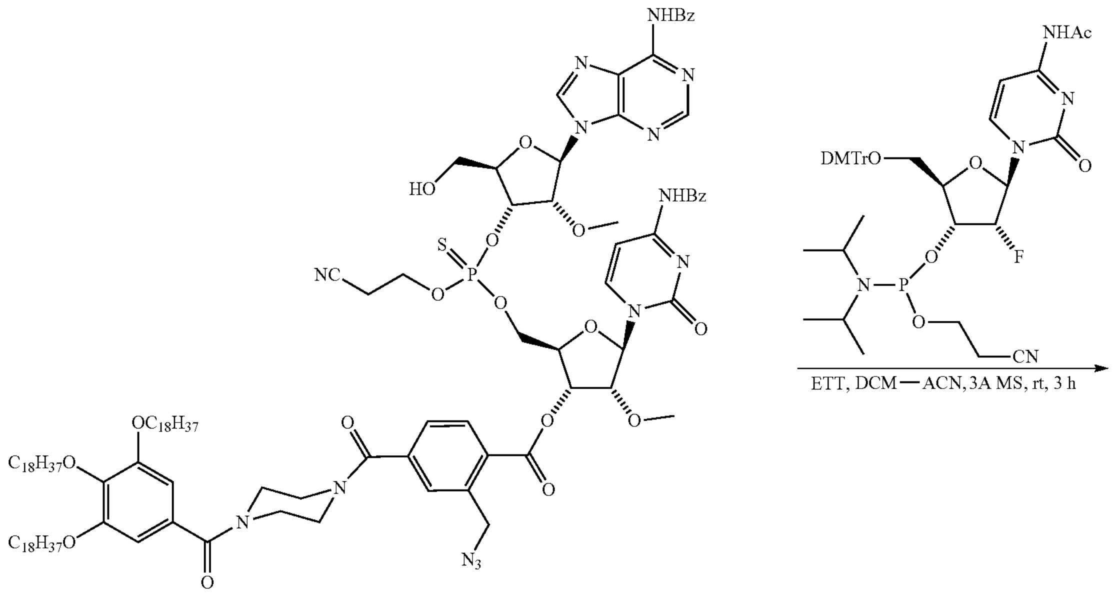
CMPD-003-114
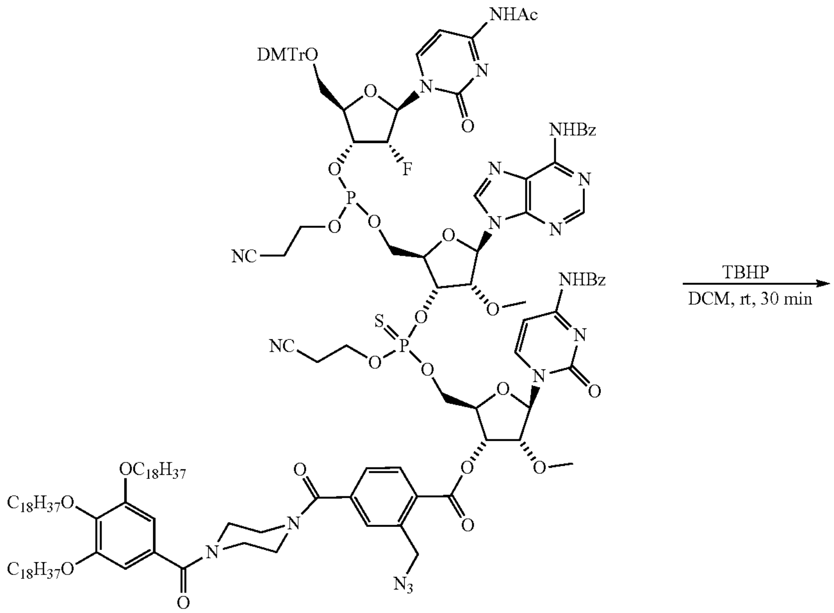
CMPD-003-115

-continued
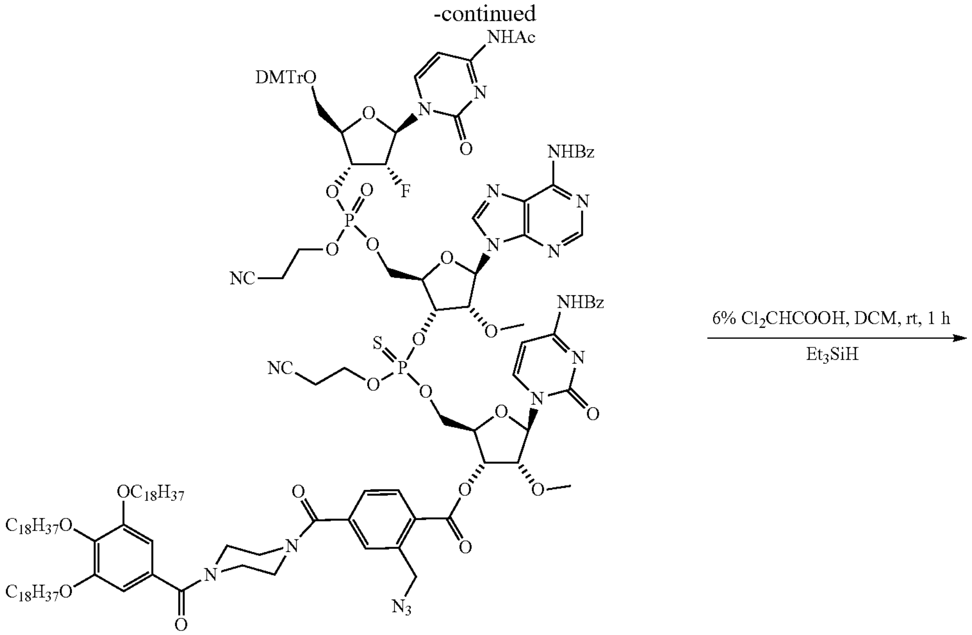
CMPD-003-116
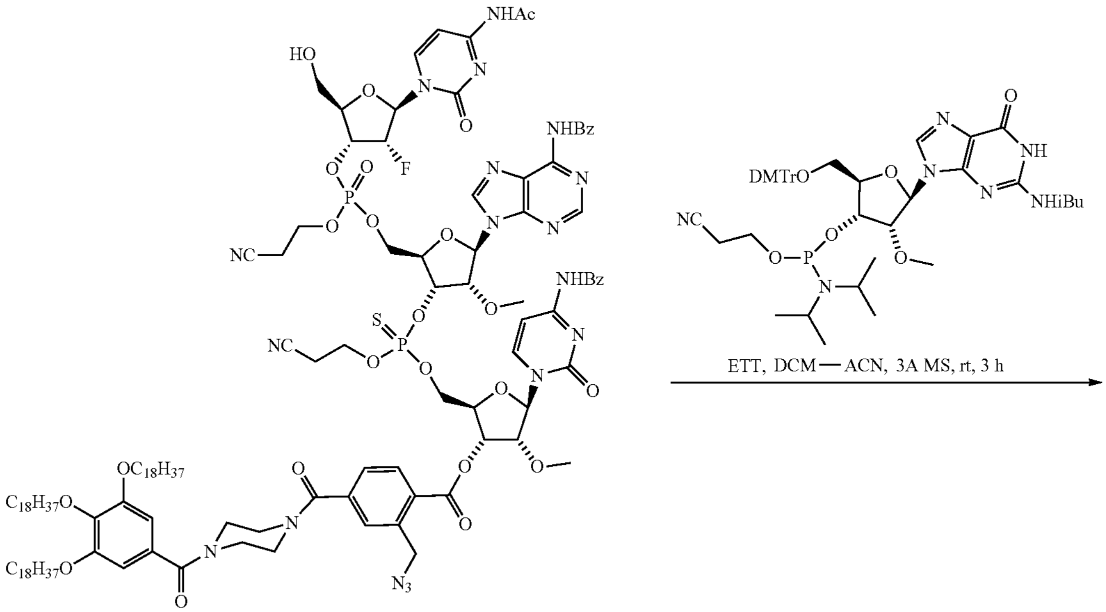
CMPD-003-117

-continued
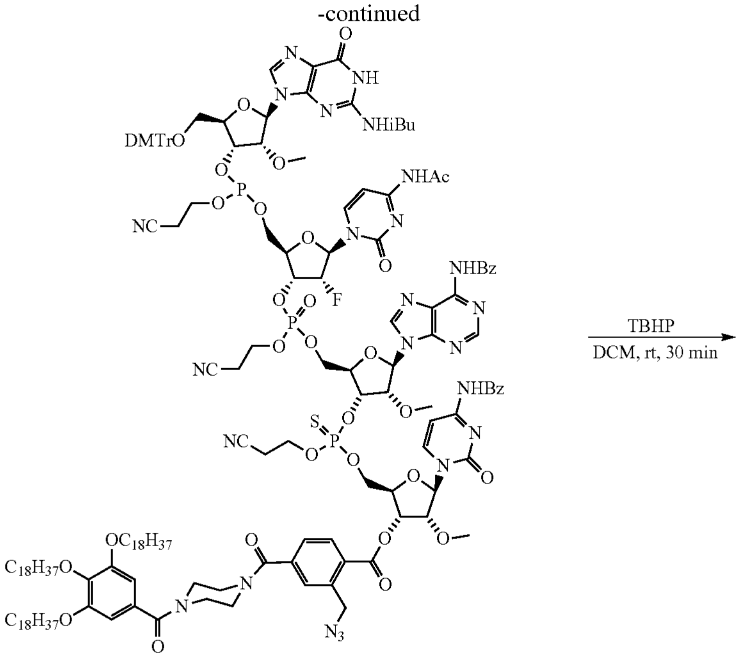
CMPD003-118
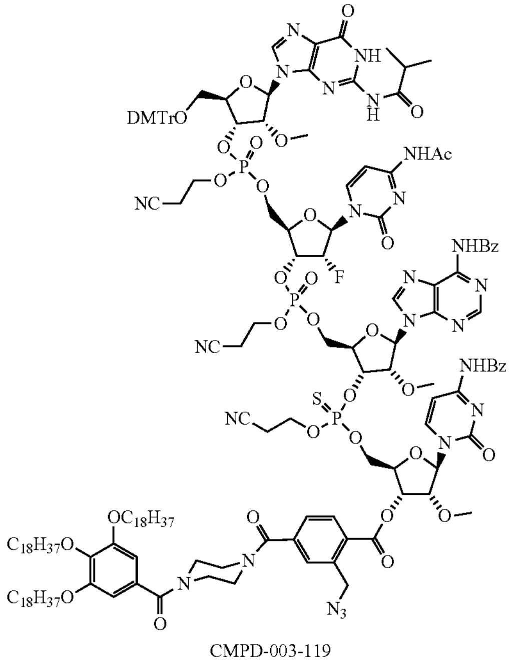
CMPD-003-119

1. Synthesis of CMPD-003-100

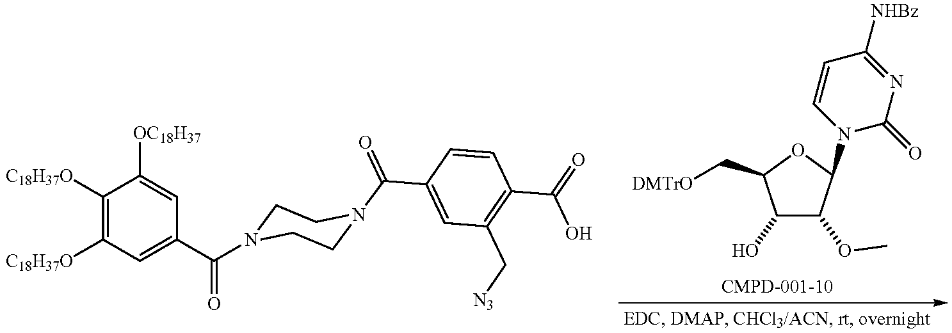

CMPD-003-0

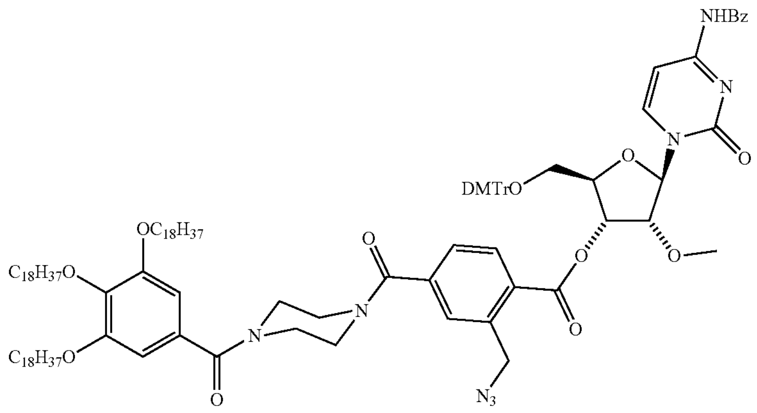

CMPD-003-100

To a solution of CMPD-003-0 (3.2 g, 2.67 mmol 1.0 eq.) in 320 mL of chloroform/acetonitrile (10/1, v/v) with an inert atmosphere of argon was added CMPD-001-10 (3.5 g, 5.34 mmol, 2.0 quiv), 1-(3-Dimethylaminopropyl)-3-ethylcarbodiimide hydrochloride (0.76 g, 4.00 mmol, 1.5 eq.) and 4-Dimethylaminopyridine (0.49 mg, 4.00 mmol, 1.5 eq.) in order at room temperature. The resulting solution was stirred overnight at room temperature. The resulting solution was precipitated by addition of acetonitrile, and the solid was collected by filtration. 3.2 g (65%) of CMPD-003-100 was obtained as a white solid. $[M/2+H]^+$ (ESI): 923.

2. Synthesis of CMPD-003-101

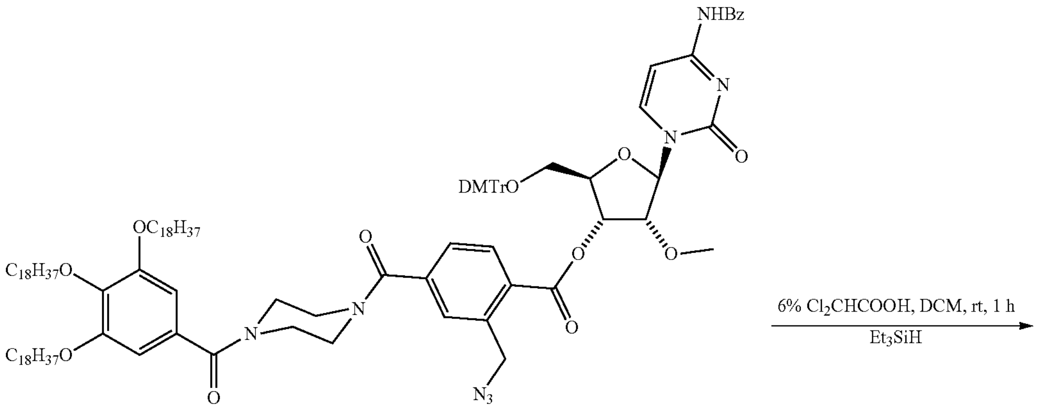

CMPD-003-100

-continued

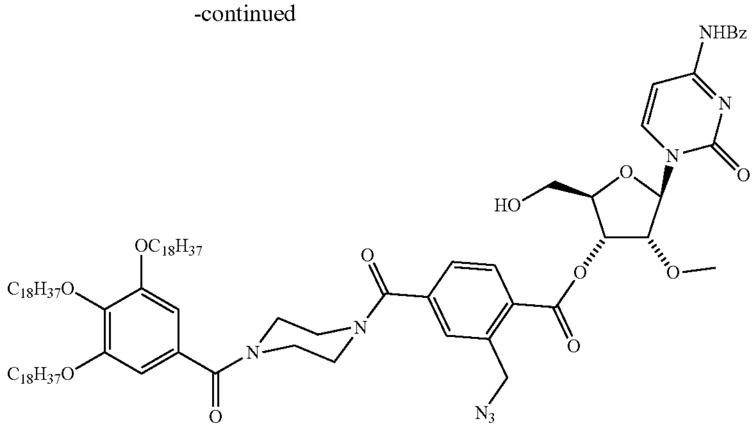

CMPD-003-101

To a solution of CMPD-003-100 (3.2 g, 1.73 mmol, 1.0 eq) in 320 mL of dichloromethane was added 19.2 mL of dichloroacetic acid and triethylsilane (0.5 g, 5.32 mmol, 2.5 eq.) sequentially at room temperature. The resulting solution was stirred for 1 h at 25° C. The resulting solution was precipitated by addition of acetonitrile, and the solid was collected by filtration. 2.5 g (93%) of CMPD-003-101 was obtained as an off-white solid. MS m/z $[M+H]^+$ (ESI): 1543.

3. Synthesis of CMPD-003-102

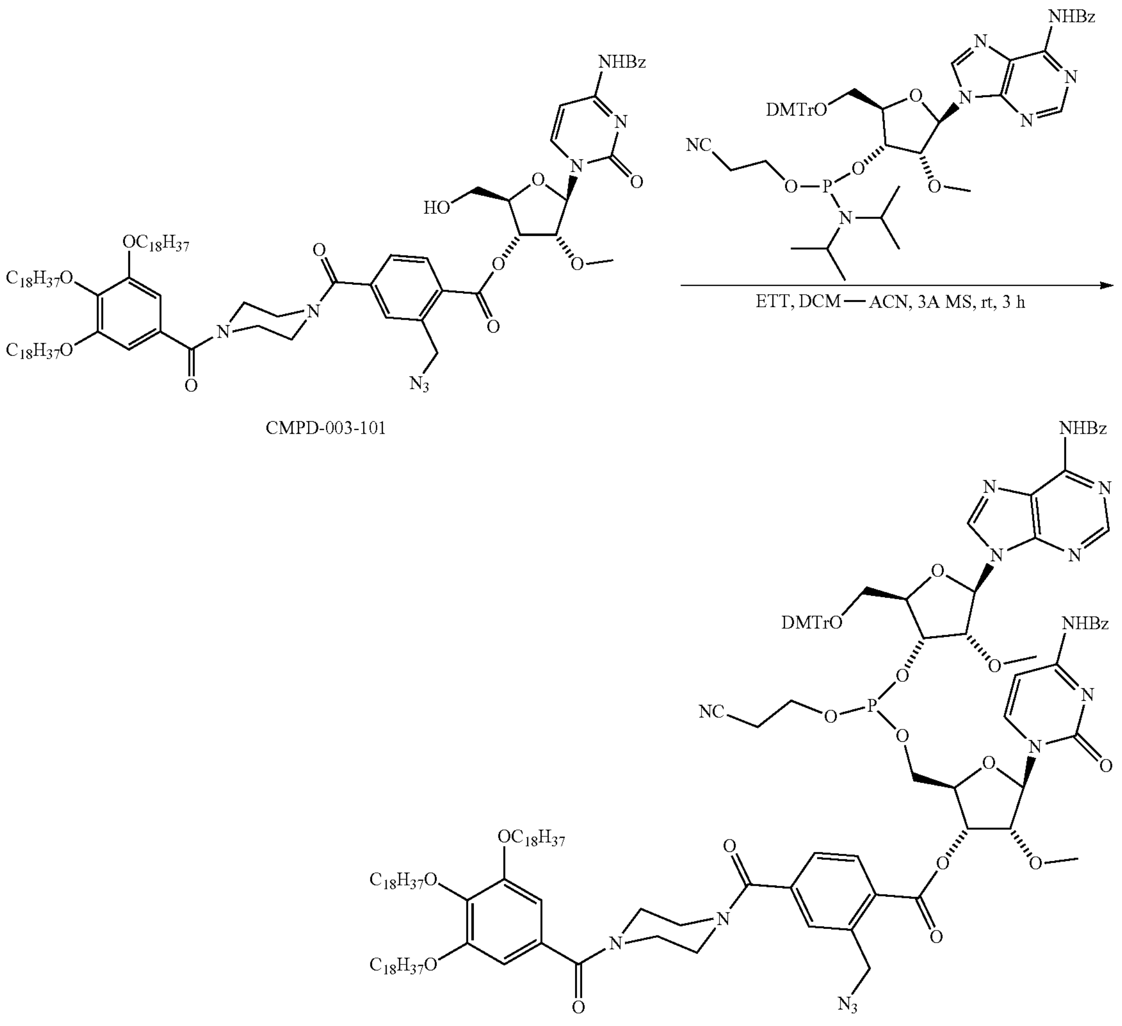

CMPD-003-102

CMPD-003-101 was dried by repeated co-evaporations with dry pyridine and dry toluene. To a solution of CMPD-003-101 (2.5 g, 1.62 mmol, 1.0 eq.) in 25 mL of dichloromethane with an inert atmosphere of argon and 3A molecular sieves was added (2R,3R,4R,5R)-5-(6-benzamido-9H-purin-9-yl)-2-((bis(4-methoxyphenyl)(phenyl)methoxy)methyl)-4-methoxytetrahydrofuran-3-yl (2-cyanoethyl) diisopropylphosphoramidite (2.87 g, 3.24 mmol, 2 eq.) and 5-(Ethylthio)-1H-tetrazole (0.6 g, 4.86 mmol, 3.0 eq.) in 2.5 mL of acetonitrile sequentially at room temperature. The resulting solution was stirred for 3 h at room temperature and used at next step without further purification.

4. Synthesis of CMPD-003-103

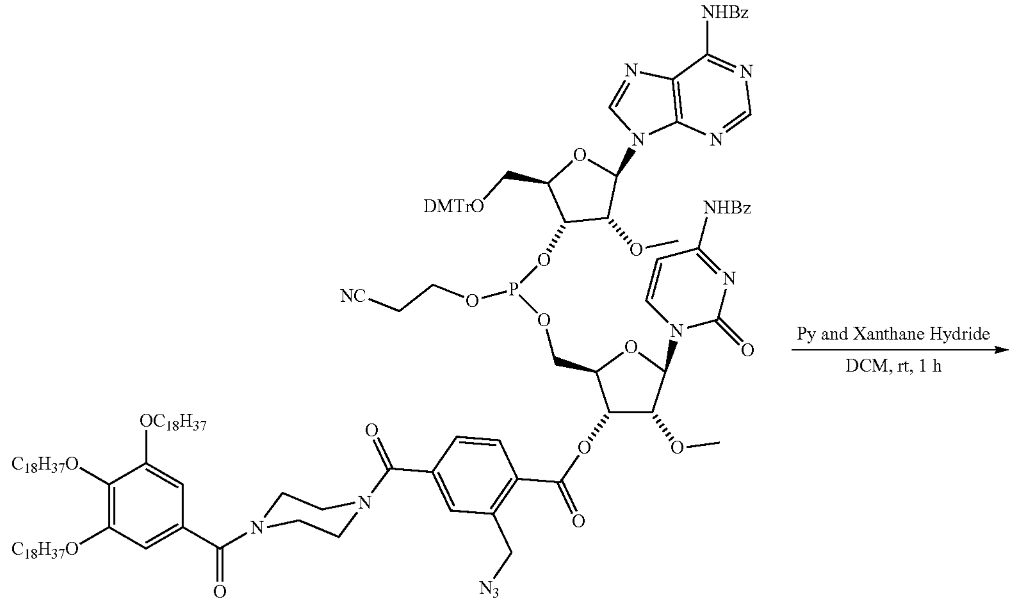

CMPD-003-102

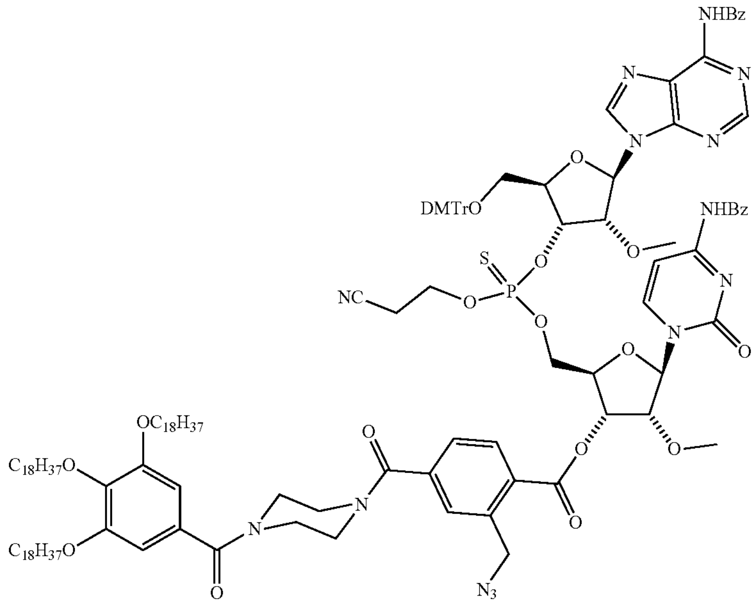

CMPD-003-103

To the resulting solution of CMPD-003-102 (1.62 mmol, 1.0 eq.) with an inert atmosphere of Ar and 3A molecular sieves was added pyridine (96 mg, 16.0 mmol, 10.0 eq.) and Xanthane Hydride (1.2 g, 0.5 mmol, 5.0 eq.) sequentially at room temperature. The resulting solution was stirred for 1 h at room temperature. The resulting solution was filtrated and precipitated by addition of acetonitrile, and the solid was collected by filtration. 2.4 g (over two steps of 65%) of CMPD-003-103 was obtained as a white solid. MS m/z $[M/2+H]^+$ (ESI): 1181.

5. Synthesis of CMPD-003-114

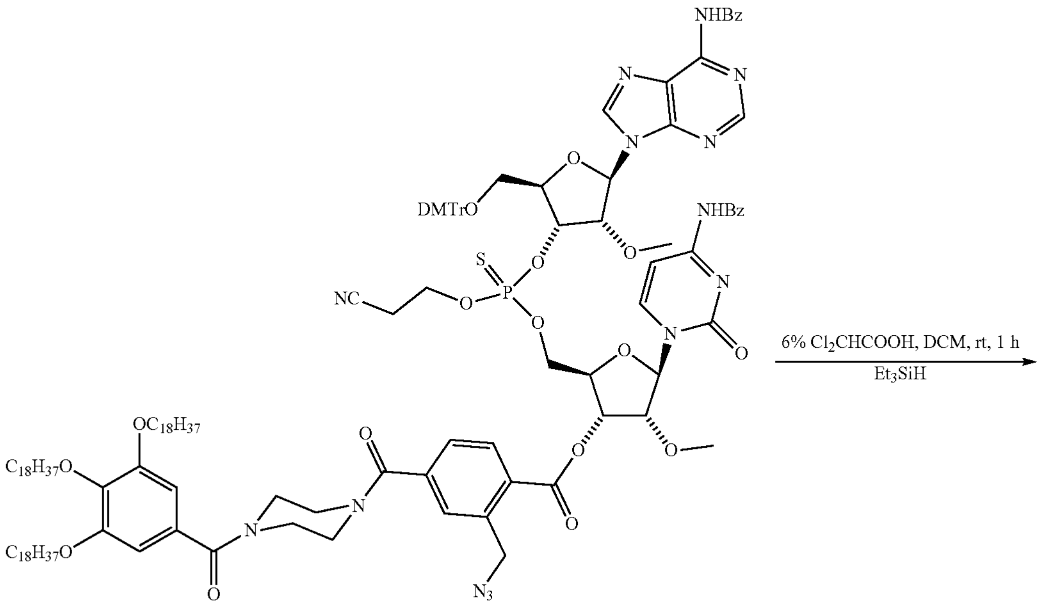

CMPD-003-103

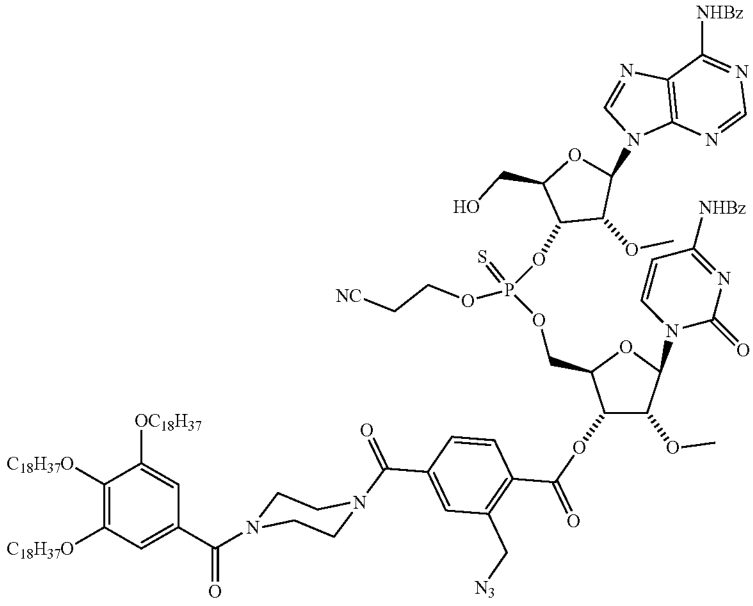

CMPD-003-114

To a solution of CMPD-003-103 (2.4 g, 1.0 mmol, 1.0 eq) in 240 mL of dichloromethane was added 14.4 mL of dichloroacetic acid and triethylsilane (0.29 g, 2.5 mmol, 2.5 eq.). The resulting solution was stirred for 1 h at 25° C. The resulting solution was precipitated by addition of acetonitrile, and the solid was collected by filtration. 1.8 g (90%) of CMPD-003-114 was obtained as an off-white solid. MS m/z $[M/2+H]^+$ (ESI): 1030. $^{31}P$ NMR (121 MHz, DMSO-d6) δ 68.11, 67.68.

6. Synthesis of CMPD-003-115

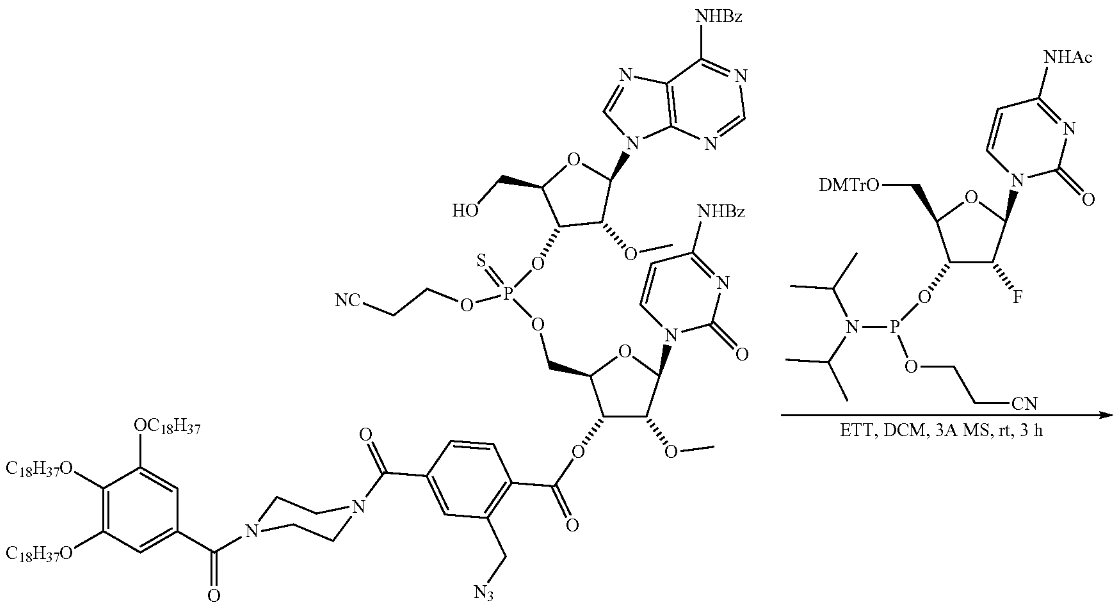

CMPD-003-114

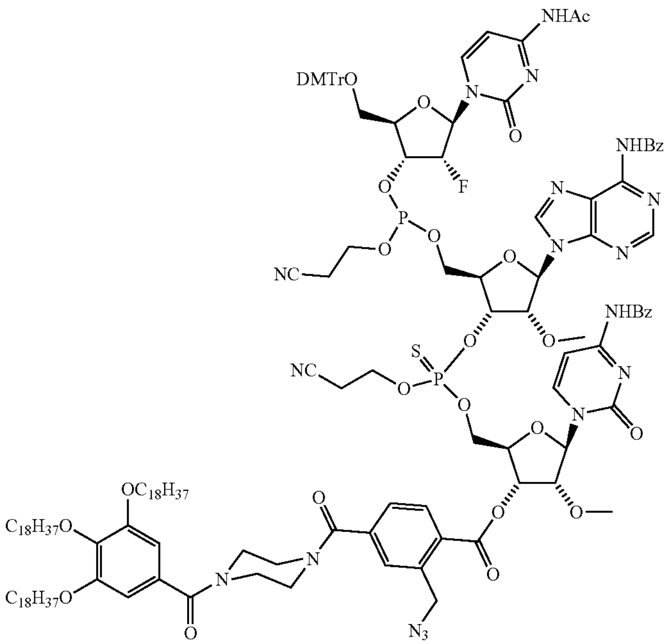

CMPD-003-115

CMPD-003-114 was dried by repeated coevaporations with dry pyridine and dry toluene. To a solution of CMPD-003-114 (1.8 g, 0.87 mmol, 1.0 eq.) in 18 mL of dichloromethane with an inert atmosphere of Ar and 3A molecular sieves was added (2R,3R,4R,5R)-5-(4-acetamido-2-oxopyrimidin-1(2H)-yl)-2-((bis(4-methoxyphenyl)(phenyl)methoxy)methyl)-4-fluorotetrahydrofuran-3-yl (2-cyanoethyl) diisopropylphosphoramidite (1.38 g, 17.5 mmol, 2 eq.) and 5-(Ethylthio)-1H-tetrazole (0.34 g, 2.62 mmol, 3.0 eq.) in 1.8 mL of acetonitrile sequentially at room temperature. The resulting solution was stirred for 3 h at room temperature and used at next step without further purification.

7. Synthesis of CMPD-003-116

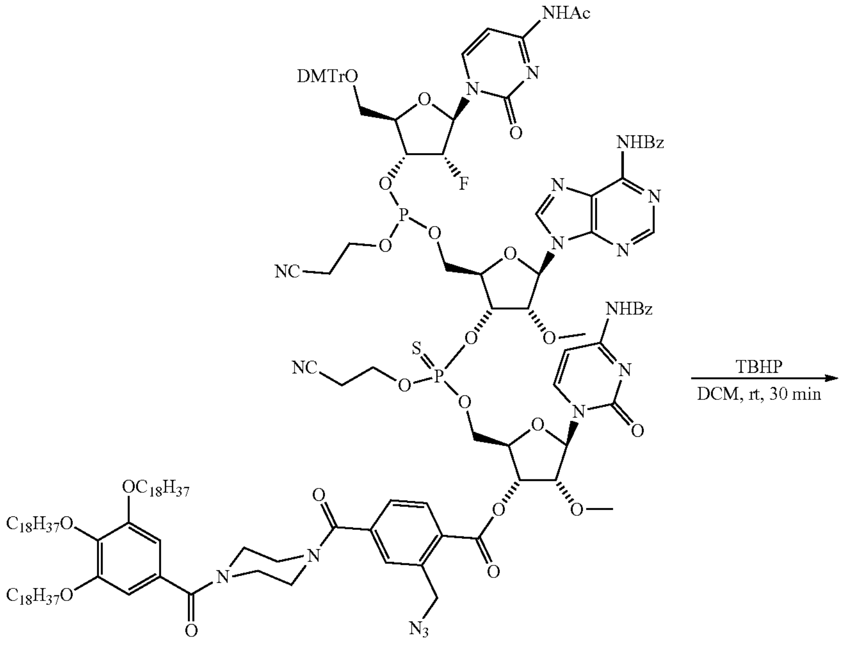

CMPD-003-115

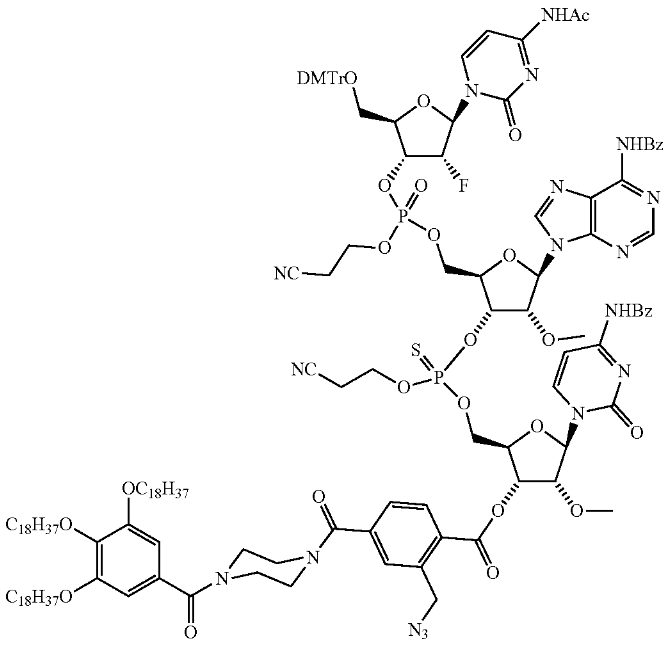

CMPD-003-116

To the resulting solution of CMPD-003-115 (0.87 mmol, 1.0 eq.) with an inert atmosphere of argon was added tert-Butyl hydroperoxide (0.56 g, 4.35 mmol, 5.0 eq.) at room temperature. The resulting solution was stirred for 1 h at room temperature. The resulting solution was filtrated and precipitated by addition of acetonitrile, and the solid was collected by filtration. 1.8 g (over two steps of 75%) of CMPD-003-116 was obtained as a white solid. MS m/z $[M/2+H]^+$ (ESI): 1382.

8. Synthesis of CMPD-003-117

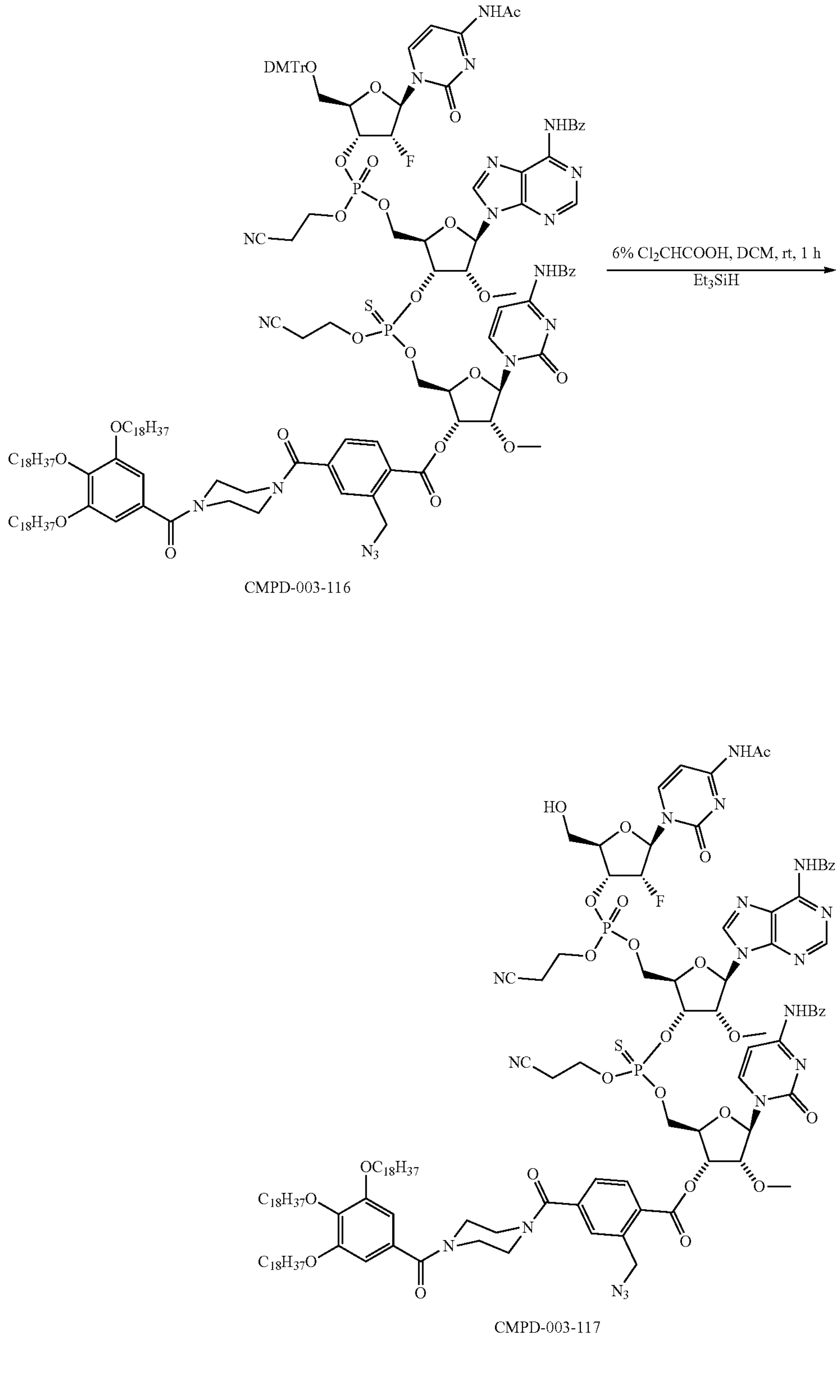

CMPD-003-116

CMPD-003-117

To a solution of CMPD-003-116 (1.8 g, 0.65 mmol, 1.0 eq) in 18 mL of dichloromethane was added 1.08 mL of dichloroacetic acid and triethylsilane (0.19 g, 1.62 mmol, 2.5 eq.) sequentially at room temperature. The resulting solution was stirred for 1 h at 25° C. The resulting solution was precipitated by addition of acetonitrile, and the solid was collected by filtration. 1.5 g (94%) of CMPD-003-117 was obtained as an off-white solid. MS m/z $[M/2+H]^+$ (ESI): 1231. $^{31}P$ NMR (121 MHz, DMSO-d6) δ 67.78, 67.71, 67.38, 67.21, −2.26, −2.50.

9. Synthesis of CMPD-003-118

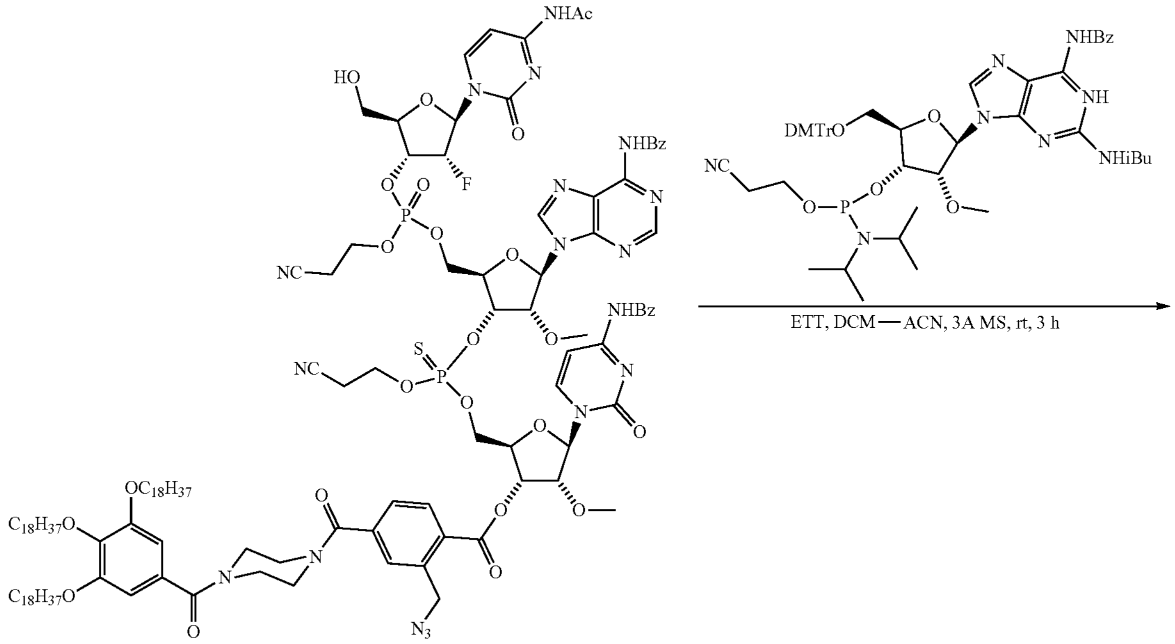

CMPD-003-117

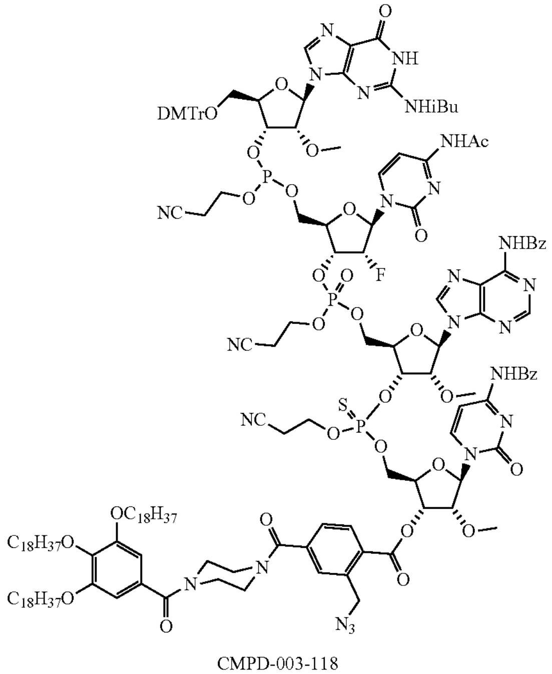

CMPD-003-118

CMPD-003-117 was dried by repeated coevaporations with dry pyridine and dry toluene. To a solution of CMPD-003-117 (1.5 g, 0.61 mmol, 1.0 eq.) in 15 mL of dichloromethane with an inert atmosphere of argon and 3A molecular sieves was added (2R,3R,4R,5R)-2-((bis(4-methoxyphenyl)(phenyl)methoxy)methyl)-5-(2-isobutyramido-6-oxo-1,6-dihydro-9H-purin-9-yl)-4-methoxytetrahydrofuran-3-yl (2-cyanoethyl) diisopropylphosphoramidite (1.06 g, 1.2 mmol, 2 eq.) and 5-(Ethylthio)-1H-tetrazole (0.24 g, 1.83 mmol, 3.0 eq.) in 1.5 mL of acetonitrile sequentially at room temperature. The resulting solution was stirred for 3 h at room temperature and used for next step without further purification.

10. Synthesis of CMPD-003-119

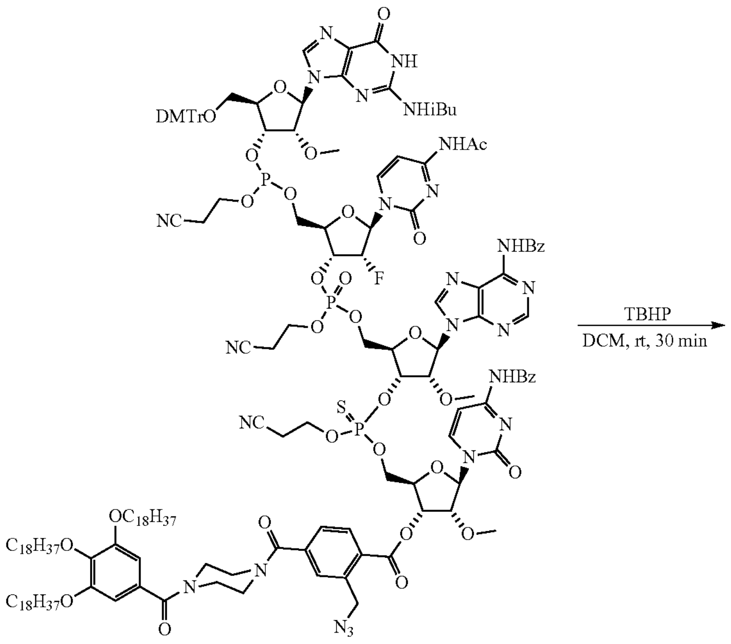

CMPD-003-118

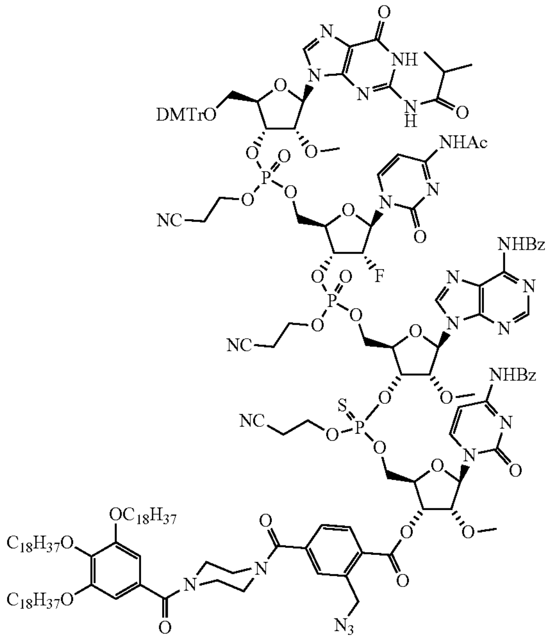

CMPD-003-119

To the resulting solution of CMPD-003-118 (0.61 mmol, 1.0 eq.) with an inert atmosphere of argon was added tert-Butyl hydroperoxide (0.39 g, 3.05 mmol, 5.0 eq.) at room temperature. The resulting solution was stirred for 1 h at room temperature. The resulting solution was filtrated and precipitated by addition of acetonitrile, and the solid was collected by filtration. 1.4 g (over two steps of 75%) of CMPD-003-119 was obtained as a white solid. MS m/z $[M/2+H]^+$ (ESI): 1624. $^{31}P$ NMR (121 MHz, DMSO-d6) δ 67.53, −2.91, −3.14.

Example 6: Cleavage and Global Deprotection of GCAC-CSS

Option A: Cleavage of Azidomethyl Link First, then De-DMT, Followed by Standard Ammonia De-Protection of Cyanoethyl and Base Protecting Groups to Provide Final Tetramer.

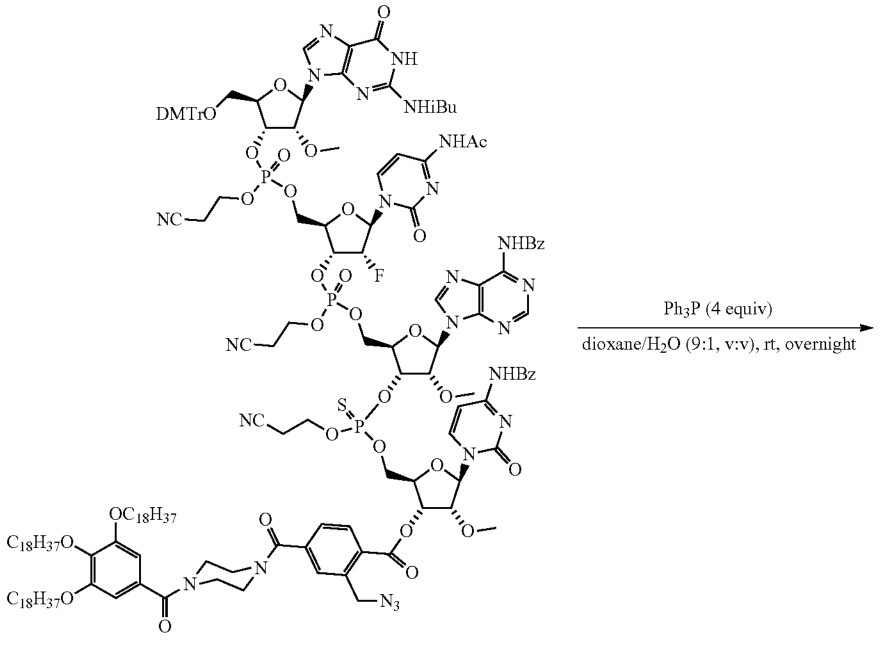

CMPD-003-119

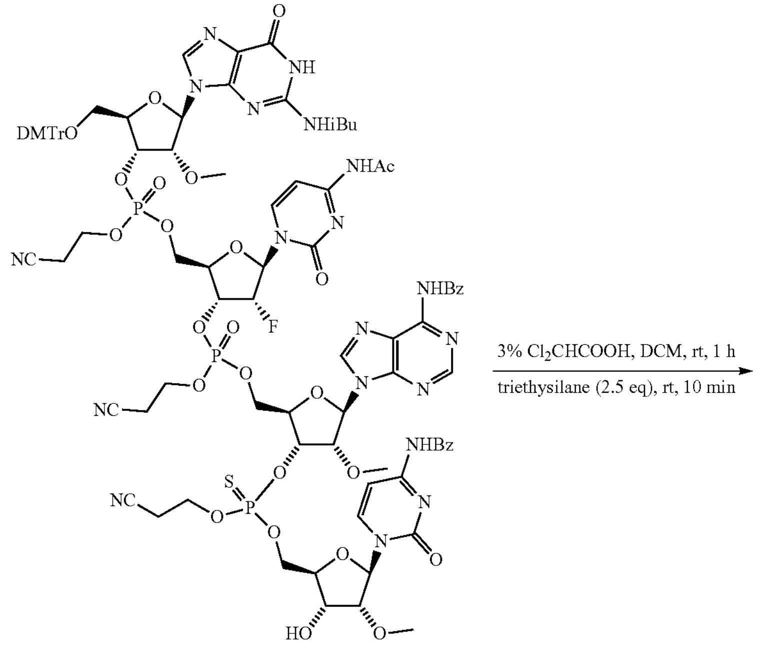

CMPD-003-200

-continued
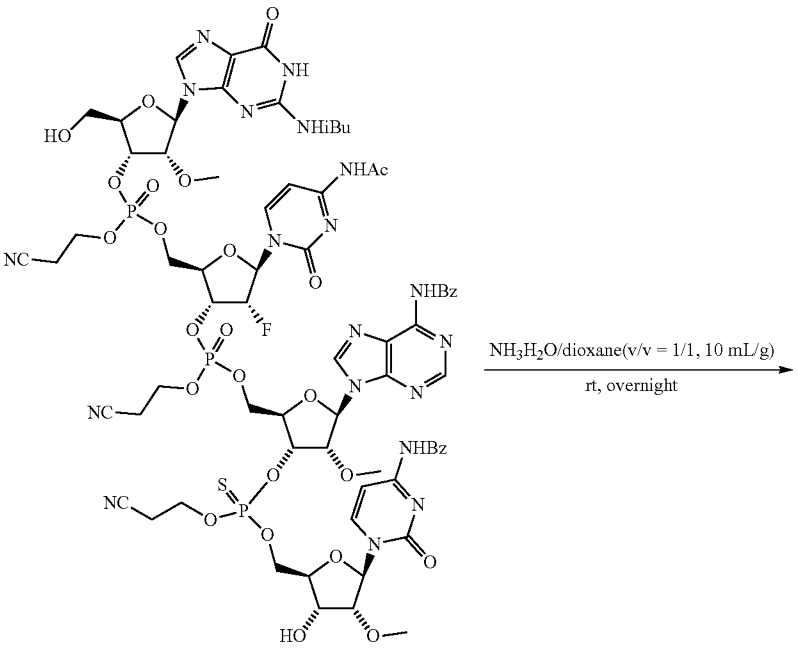
CMPD-003-201
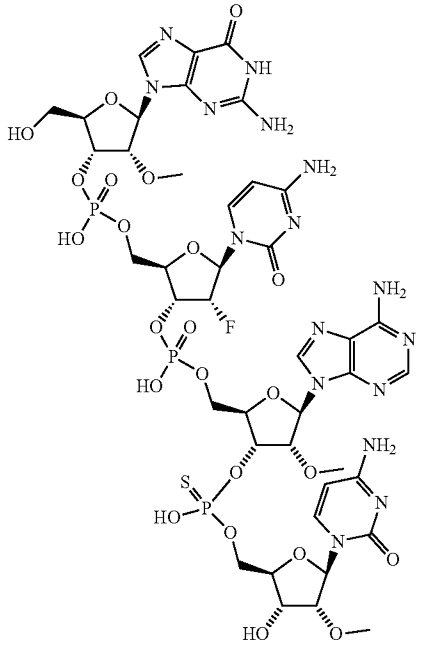
CMPD-003-202

1. Synthesis of CMPD-003-200

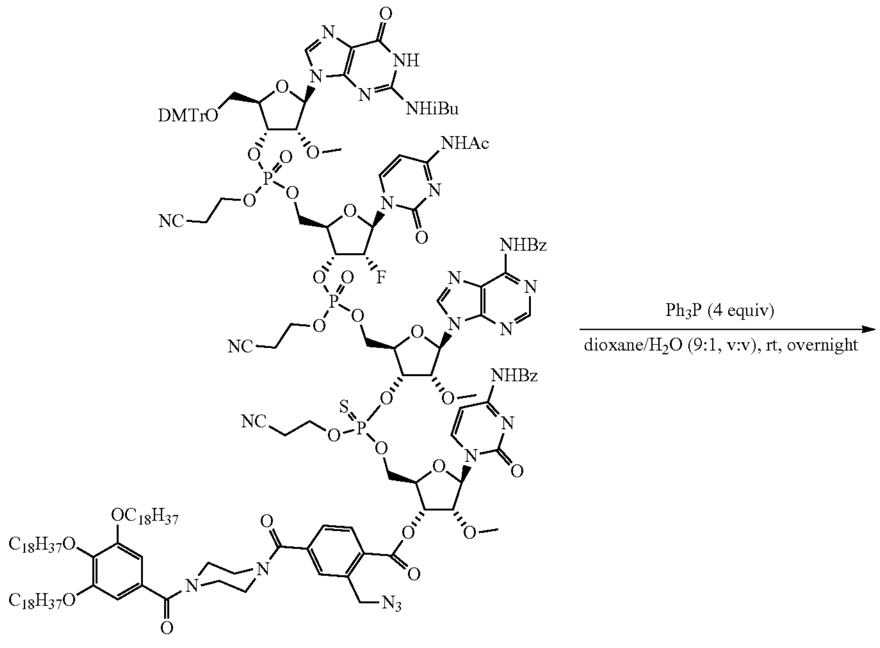

CMPD-003-119

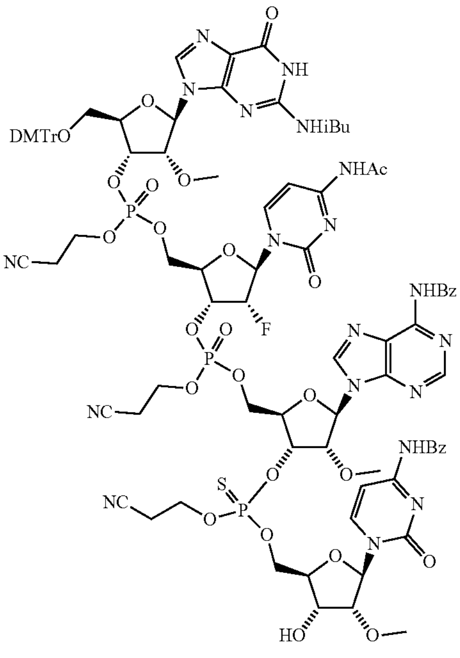

CMPD-003-200

To a solution of CMPD-003-119 (200 mg, 0.06 mmol, 1.0 eq.) in 2 mL of dioxane/water (9/1, v/v) with an inert atmosphere of argon, was added triphenylphosphine (65 mg, 0.25 mmol, 4.0 eq.) at room temperature. The reaction solution was stirred overnight at room temperature. The resulting solution was precipitated by addition of acetonitrile, and the solid was collected by filtration. The organic phase was concentrated under reduced pressure. The residue was purified by Flash-Prep-HPLC with the following conditions: Column, C18 silica gel; mobile phase, water (containing 0.04% $NH_4HCO_3$) and acetonitrile (20% acetonitrile up to 100% in 15 min); Detector, UV 254 nm. 100 mg (82%) of CMPD-003-200 was obtained as a white solid. MS m/z $[M/2+H]^+$ (ESI): 1033.

Alternative Cleavage Condition by the Following Conditions:
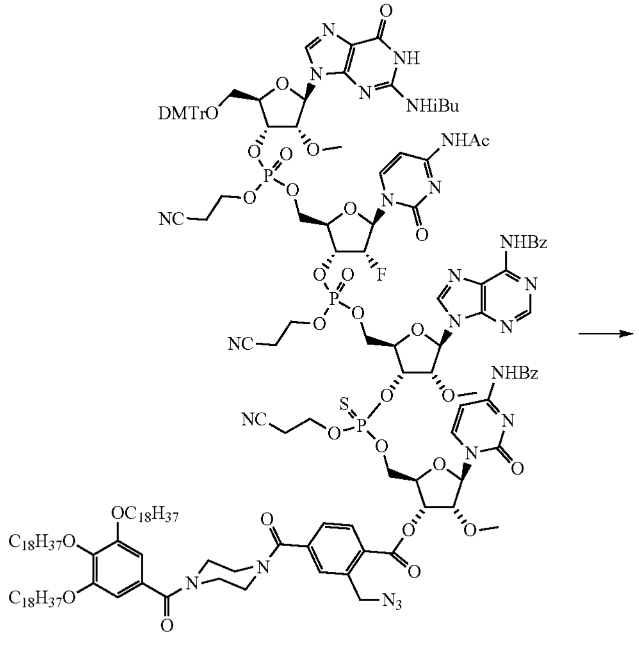
CMPD-003-119
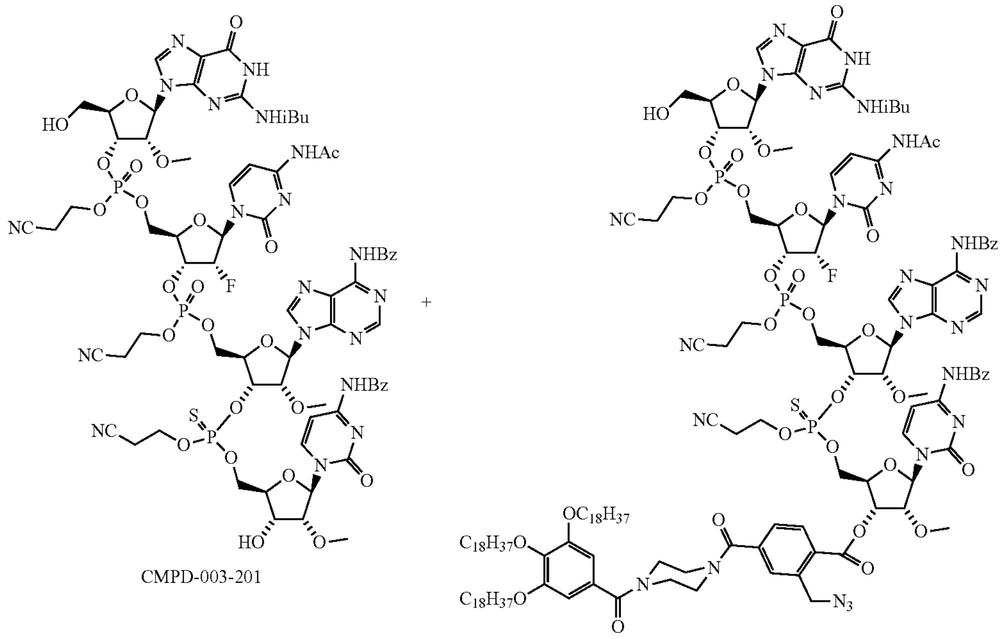
CMPD-003-201
D: Cyclohexadiene (10 eq.), Pd/C (50%, w/w), THE (50 mL/g), rt overnight, SM disappeared, 75% CMPD-003-201, 700 de-DMTr ion signal in SFC-MS for 20 mg scale.

2. Synthesis of CMPD-003-201

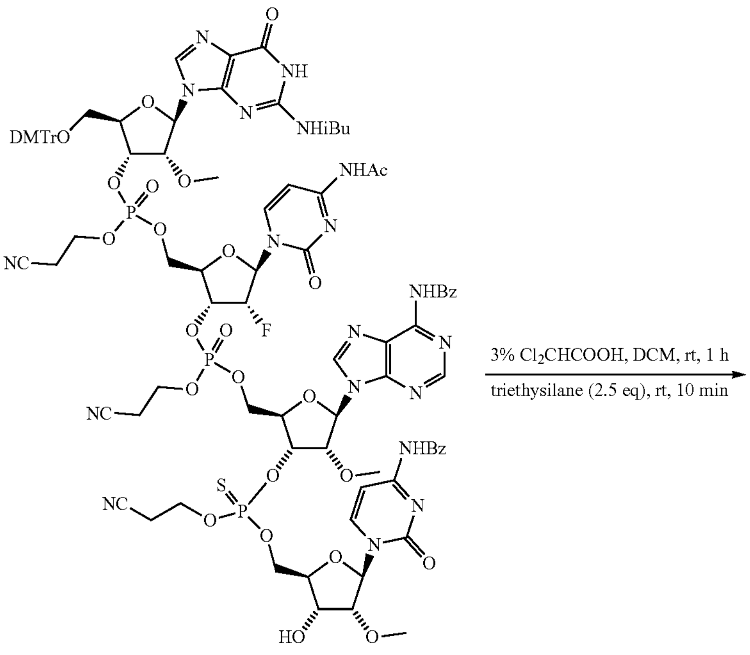

CMPD-003-200

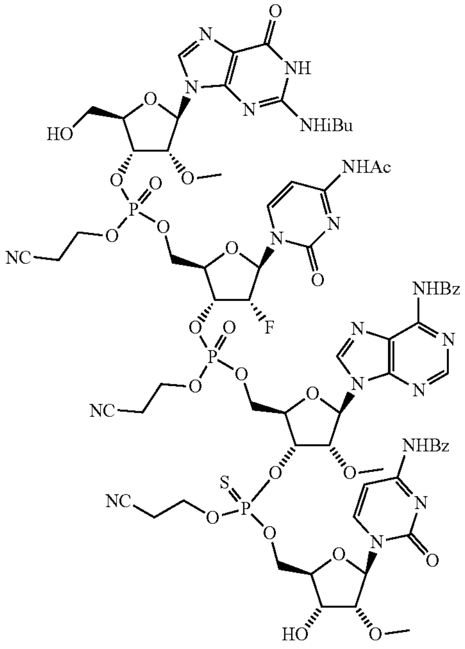

CMPD-003-201

To a solution of CMPD-003-200 (100 mg, 0.05 mmol, 1.0 eq) in 1 mL of dichloromethane was added 0.03 mL of dichloroacetic acid and triethylsilane (14 mg, 0.12 mmoL, 2.5 eq). The resulting solution was stirred for 1 h at 25° C. The resulting solution was dissolved in 20 mL of dichloromethane, washed with 2×10 mL of saturated aqueous sodium bicarbonate and 1×10 mL of saturated aqueous sodium chloride respectively. 70 mg (82%) of CMPD-003-200 was obtained as a white solid. It used at next step without further purification. MS m/z $[M+H]^+$ (ESI): 1764.

3. Synthesis of CMPD-003-202

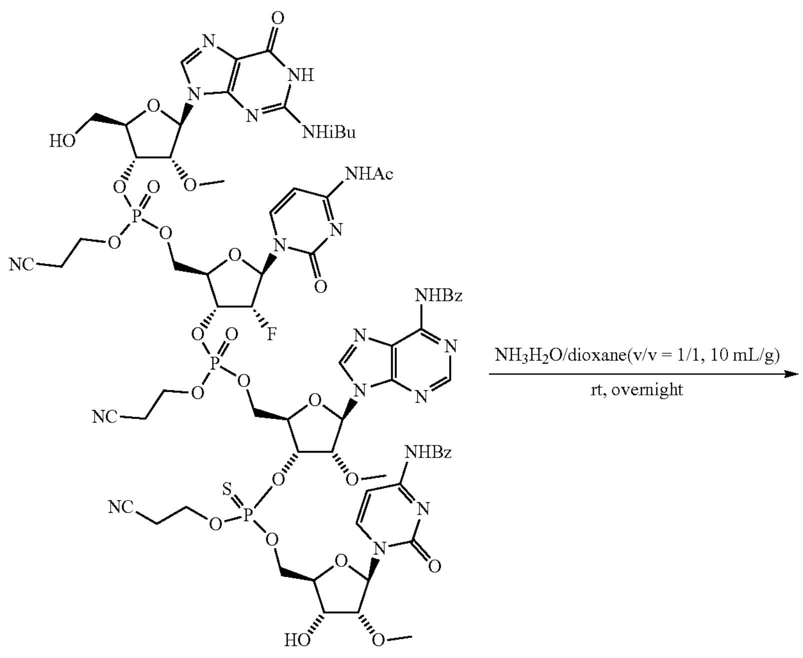

CMPD-003-201

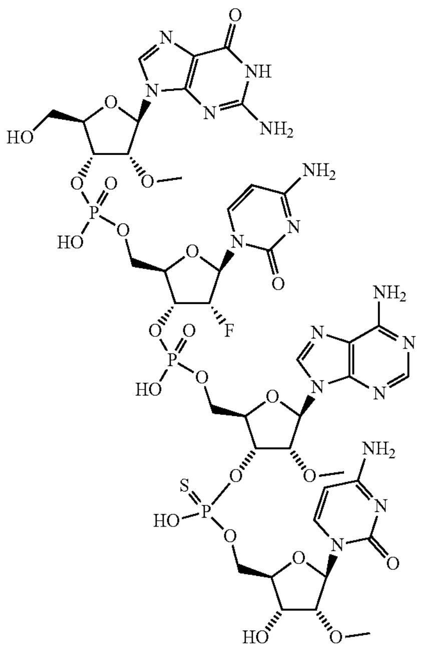

CMPD-003-202

To a solution of CMPD-003-201 (70 mg, 0.04 mmol, 1.0 eq) was added 1 mL of $NH_3H_2O$/dioxane (v/v=1/1). The resulting solution was stirred overnight at 25° C. The resulting solution was concentrated under reduced pressure. The resulting solution was precipitated by addition of dichloromethane, and the solid was collected by filtration. 20 mg of CMPD-003-200 was obtained as a white solid. MS m/z $[M+H]^+$ (ESI): 1282.

Option B: De-DMT First, then Cleavage of Azidomethyl Link, Followed by Standard Ammonia Deprotection of Cyanoethyl and Base Protecting Groups to Provide Final Tetramer.
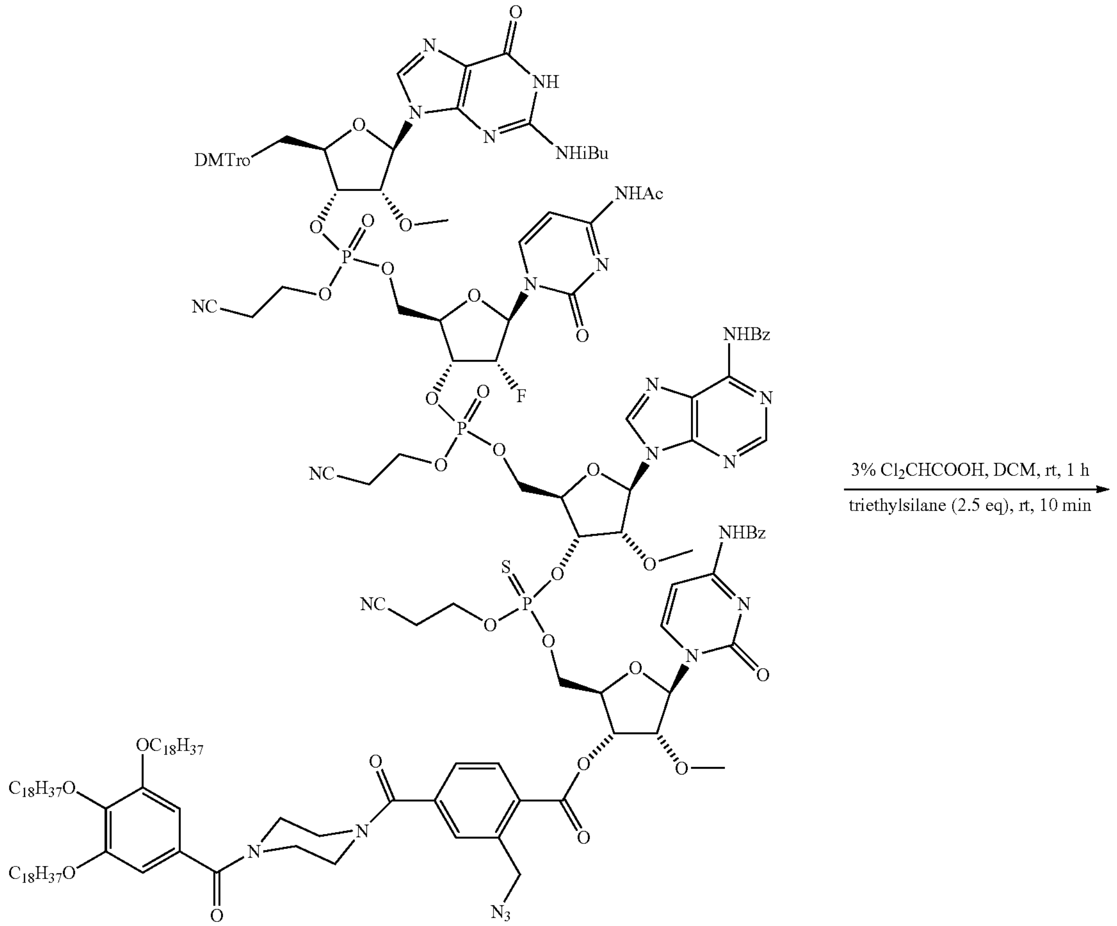
CMPD-003-119

-continued
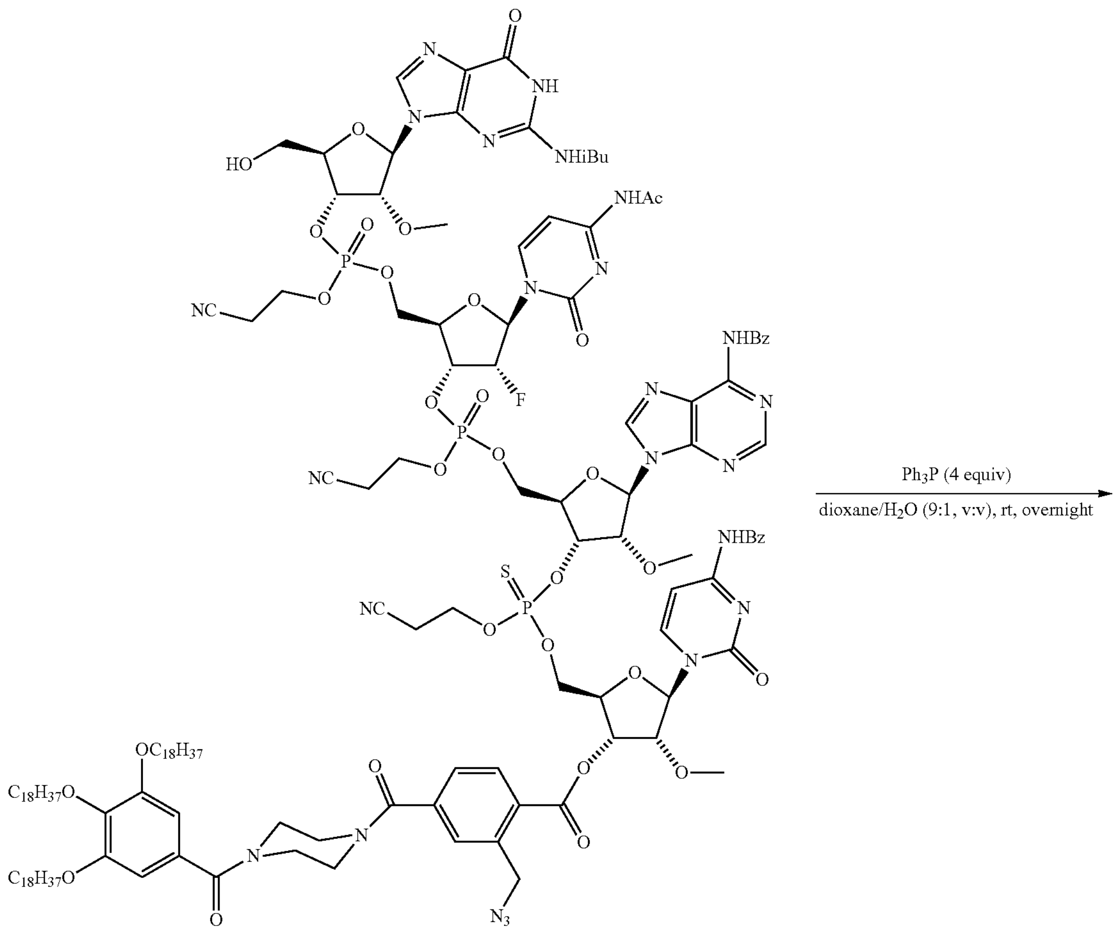
CMPD-003-300

-continued
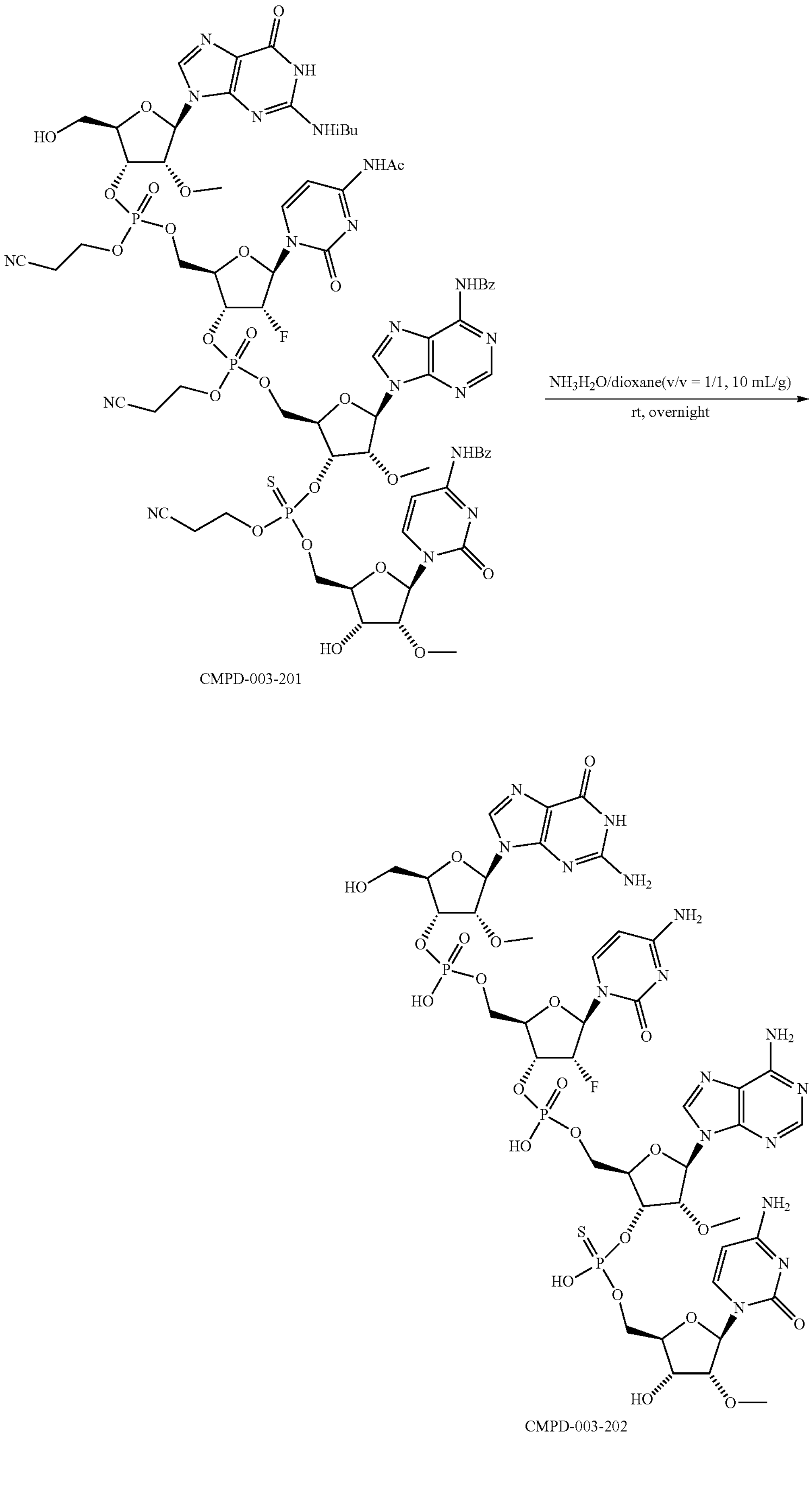
CMPD-003-201
CMPD-003-202

1. Synthesis of CMPD-003-300
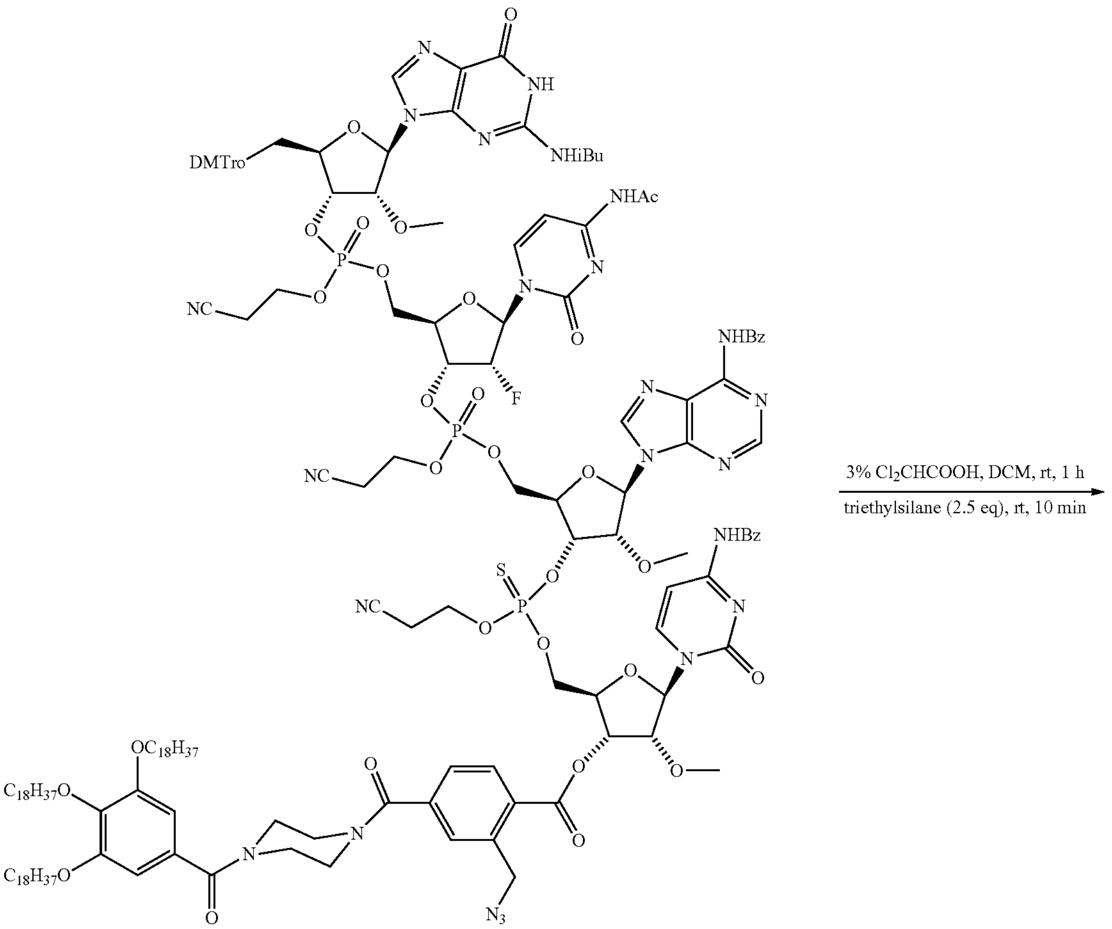
CMPD-003-119

-continued
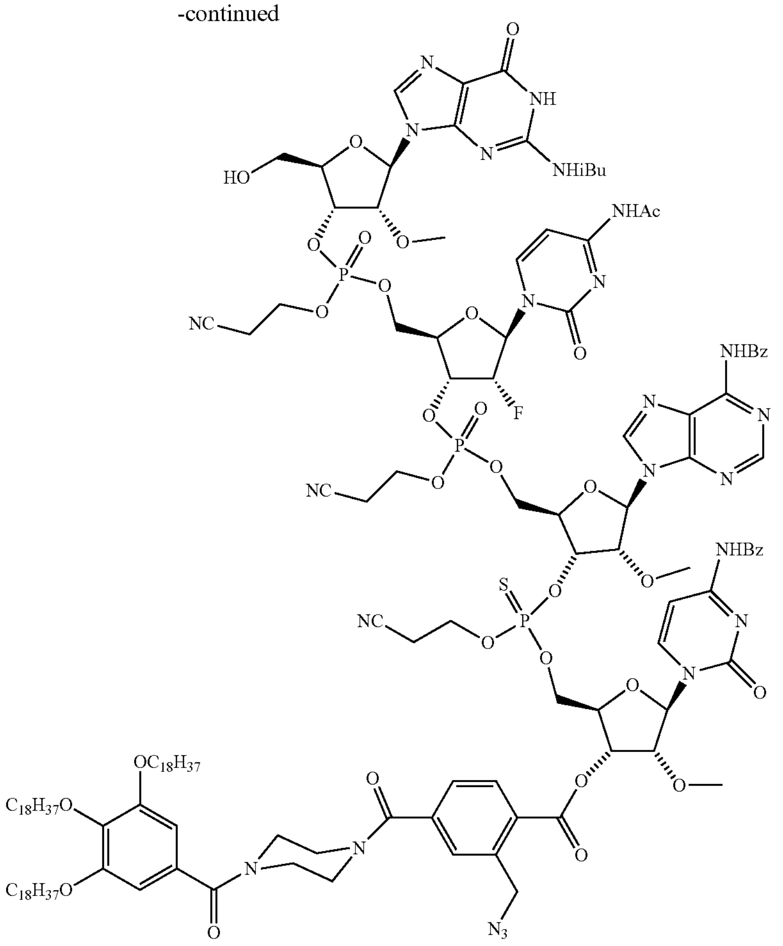
CMPD-003-300
To a solution of CMPD-003-119 (200 mg, 0.06 mmol, 1.0 eq) in 2 mL of dichloromethane was added 0.03 mL of dichloroacetic acid and triethylsilane (15 mg, 0.15 mmoL, 2.5 eq). The resulting solution was stirred for 1 h at 25° C. The resulting solution was precipitated by addition of acetonitrile, and the solid was collected by filtration. 140 mg (78%) of CMPD-003-300 was obtained as a white solid. MS m/z $[M/2+H]^+$ (ESI): 1472.

3. Synthesis of CMPD-003-201
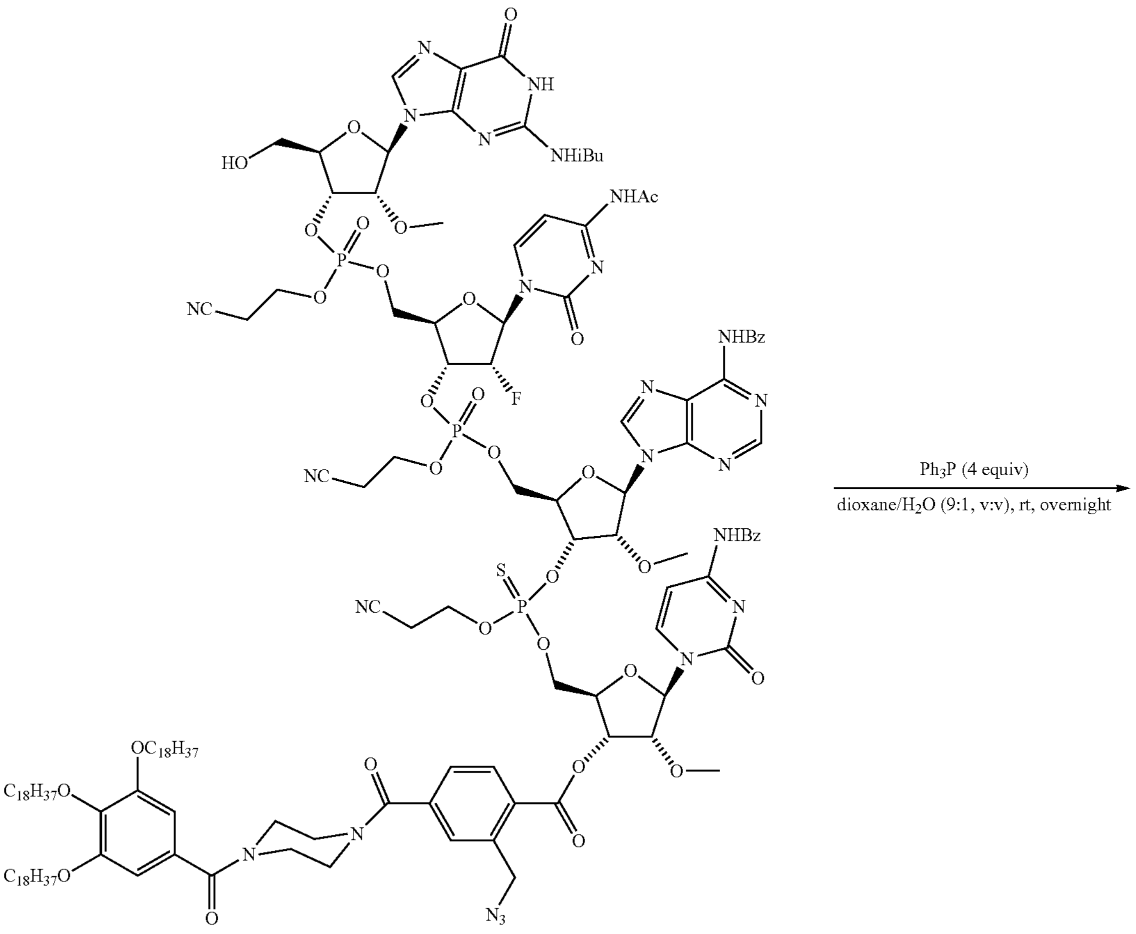
CMPD-003-300

-continued

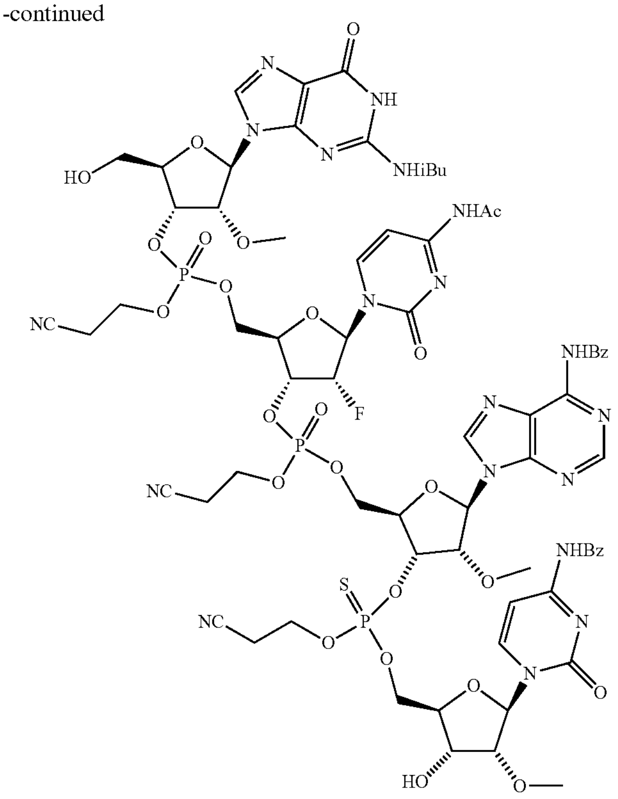

CMPD-003-201

To a solution of CMPD-003-119 (140 mg, 0.05 mmol, 1.0 eq.) in 1.5 mL of dioxane/water (9/1, v/v) with an inert atmosphere of Ar, was added triphenylphosphine (52 mg, 0.20 mmol, 4.0 eq.) at room temperature. The reaction solution was stirred overnight at room temperature. The resulting solution was precipitated by addition of acetonitrile, and the solid was collected by filtration. The organic phase was concentrated under reduced pressure. The residue was purified by Flash-Prep-HPLC with the following conditions: Column, C18 silica gel; mobile phase, water (containing 0.04% $NH_4HCO_3$) and acetonitrile (20% acetonitrile up to 100% in 15 min); 50 mg (60%) of CMPD-003-201 was obtained as a white solid. MS m/z $[M+H]^+$ (ESI): 1762.

4. Synthesis of CMPD-003-202
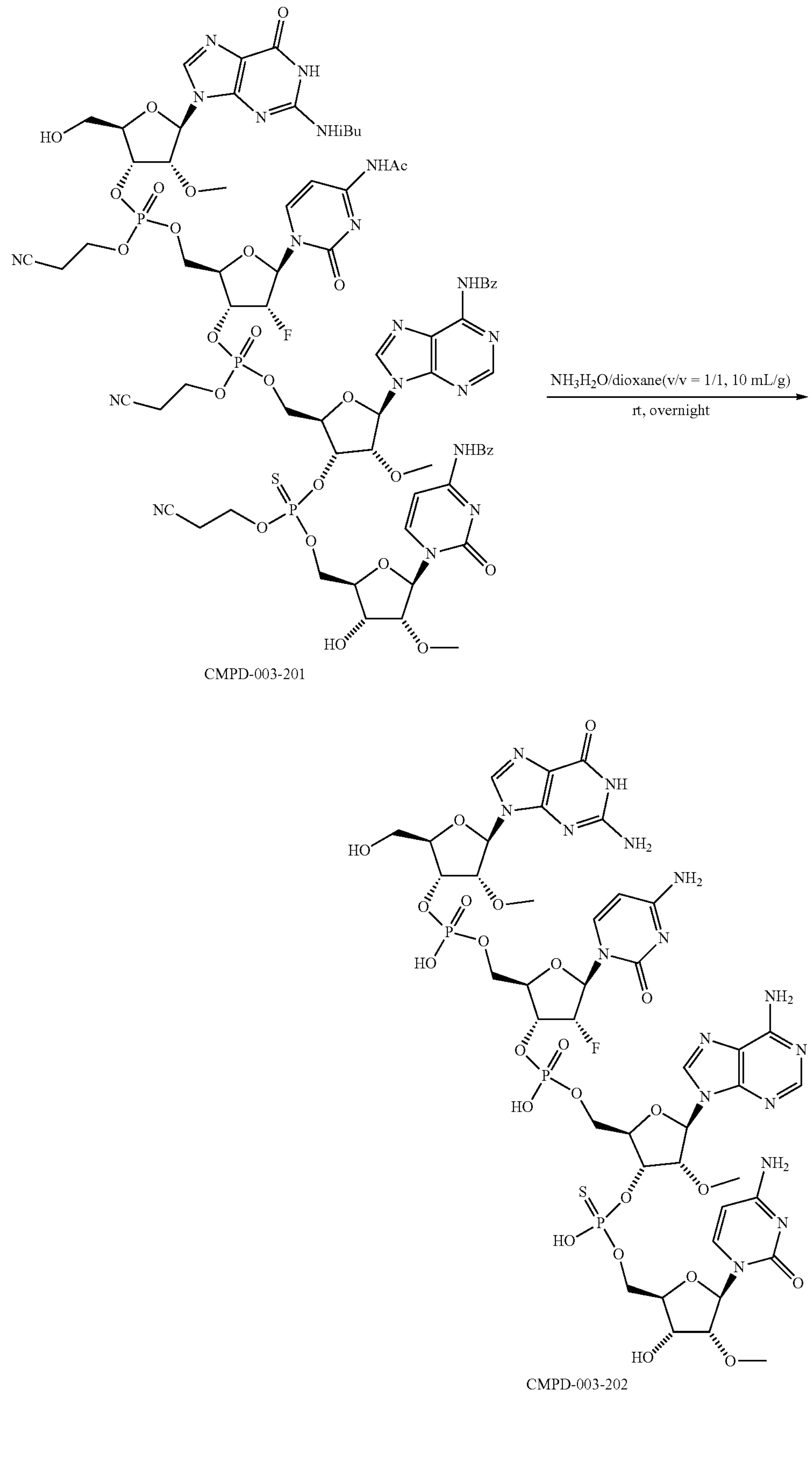
CMPD-003-201
CMPD-003-202

To a solution of CMPD-003-201 (50 mg, 0.03 mmol, 1.0 eq) was added 1 mL of $NH_3 \cdot H_2O$/dioxane (v/v=1/1). The resulting solution was stirred for overnight at 25° C. The resulting solution was concentrated under reduced pressure. The resulting solution was precipitated by addition of dichloromethane, and the solid was collected by filtration. 20 mg CMPD-003-200 was obtained as a white solid. MS m/z $[M+H]^+$ (ESI). 1282.

Example 7: Synthesis of 5'-cholesterol Conjugate of a Pentamer Oligonucleotide

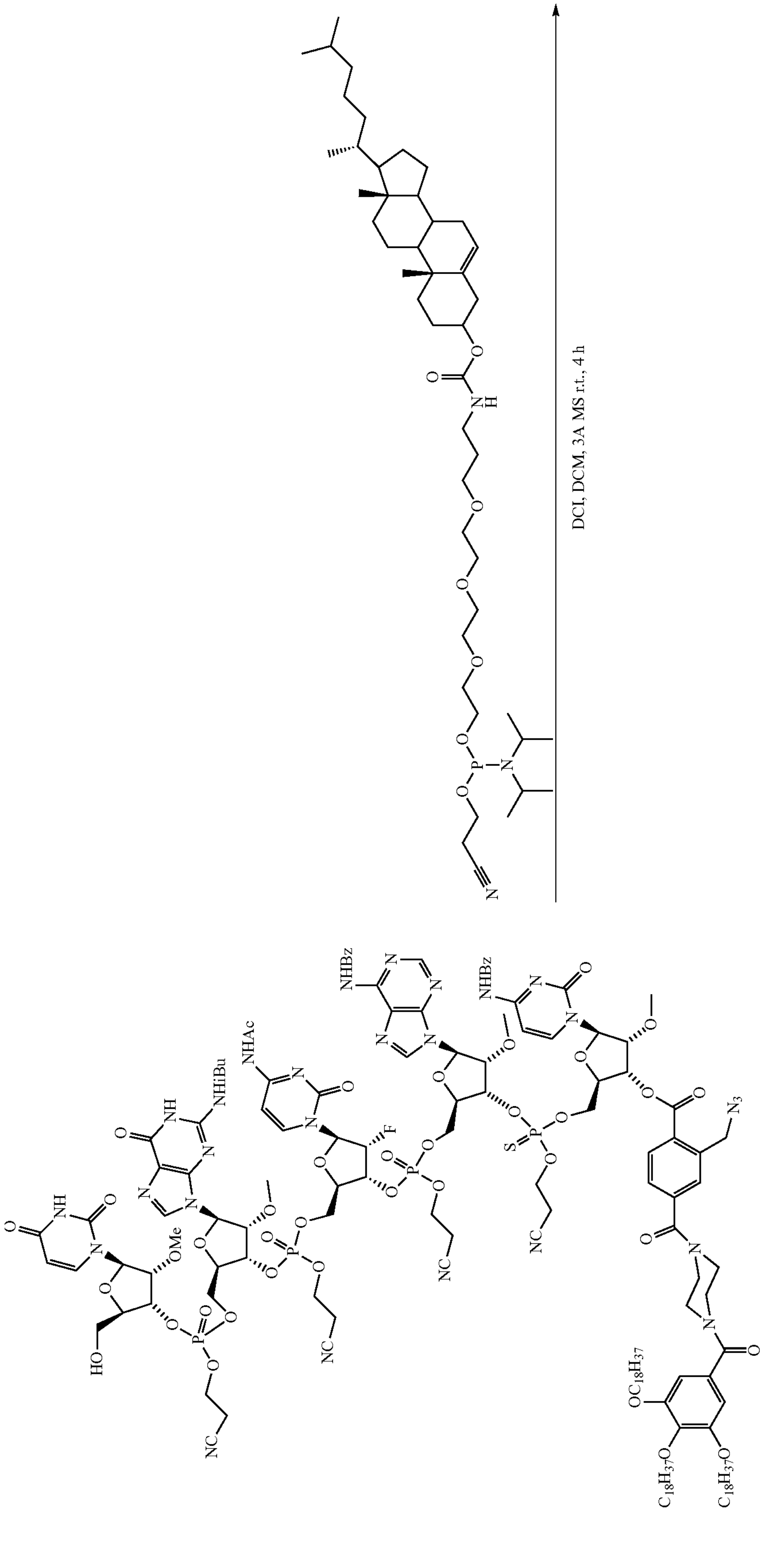
CMPD-004-001

-continued
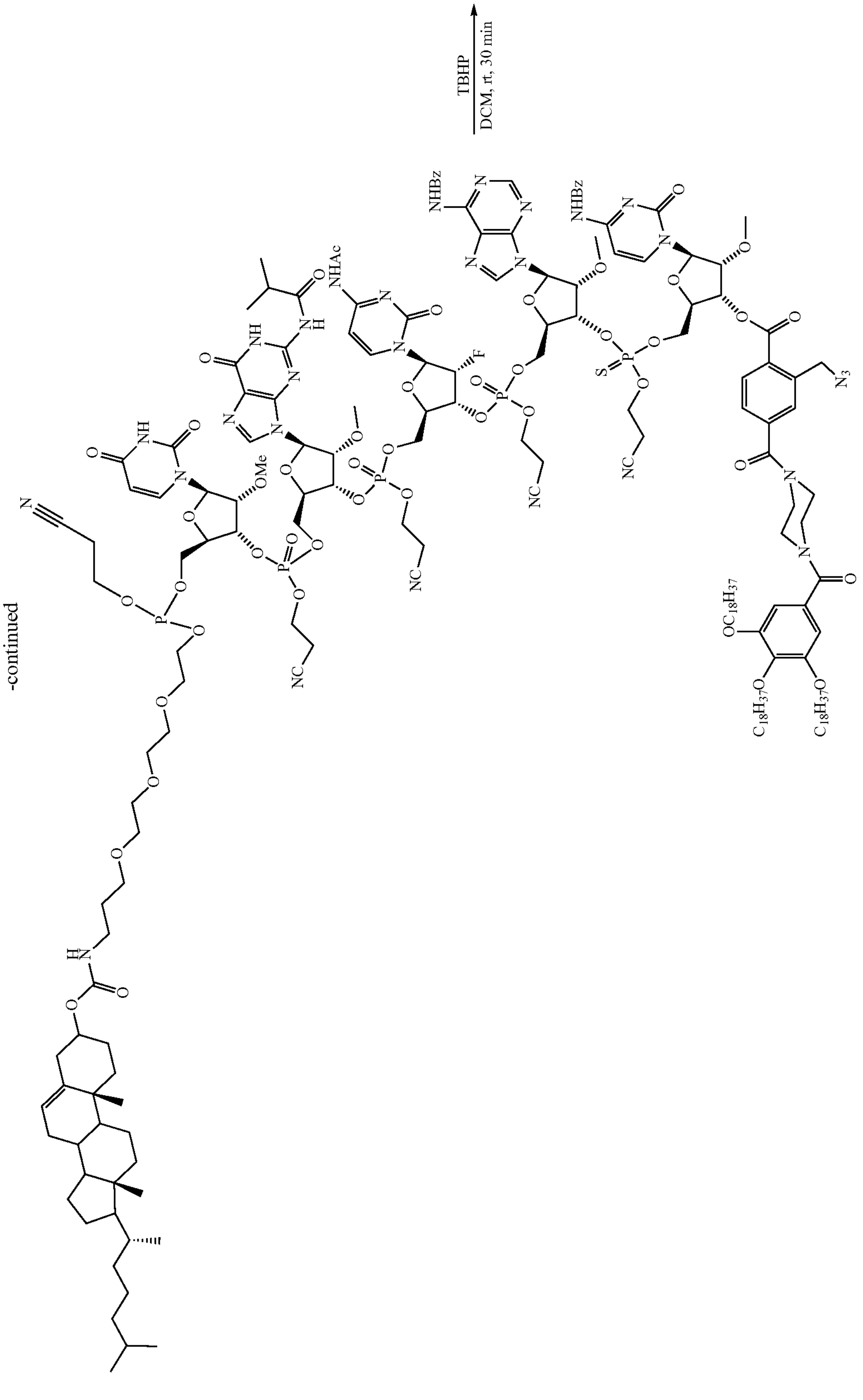
CMPD-004-002

-continued
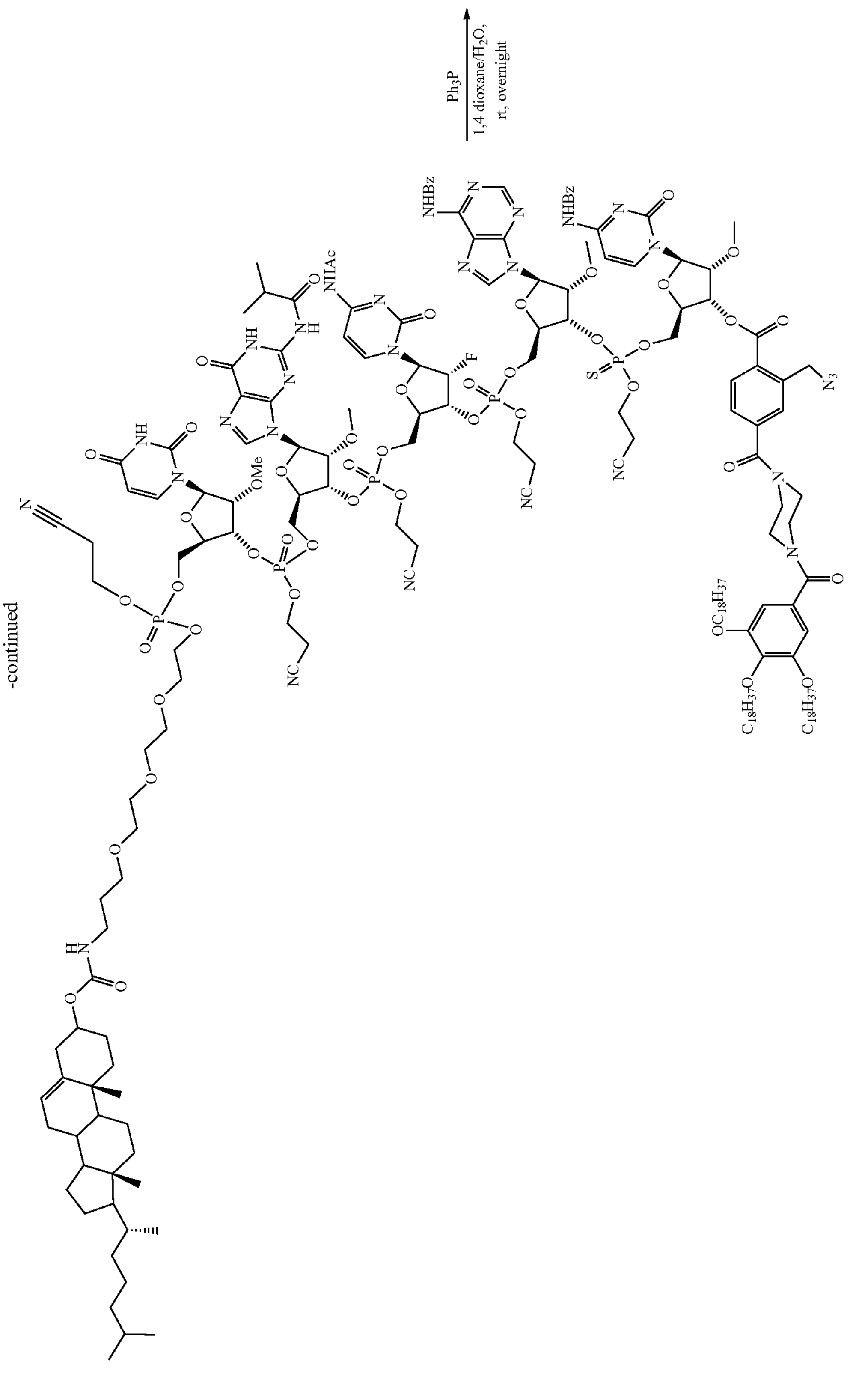
CMPD-004-003

-continued
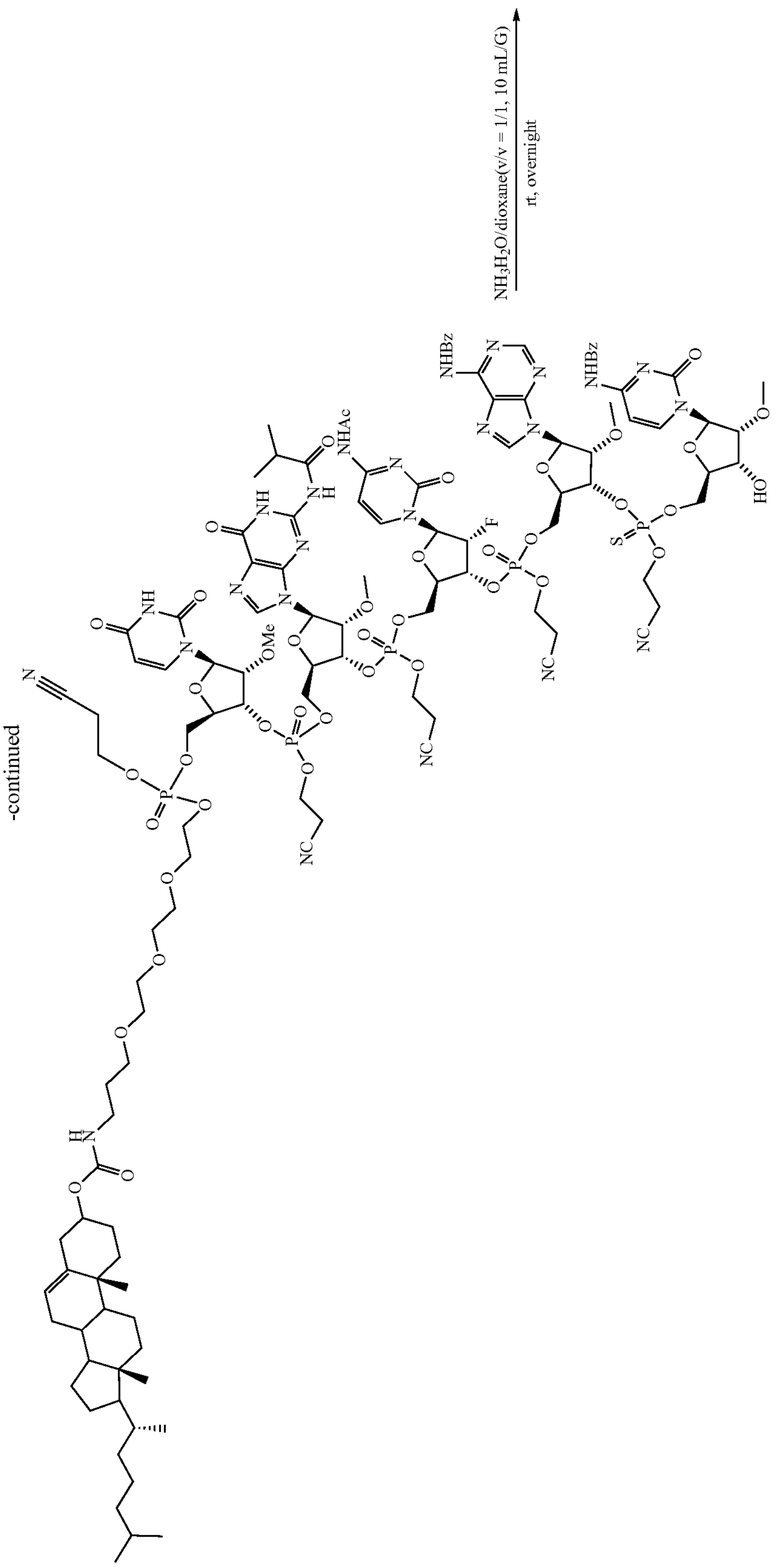
CMPD-004-004

-continued
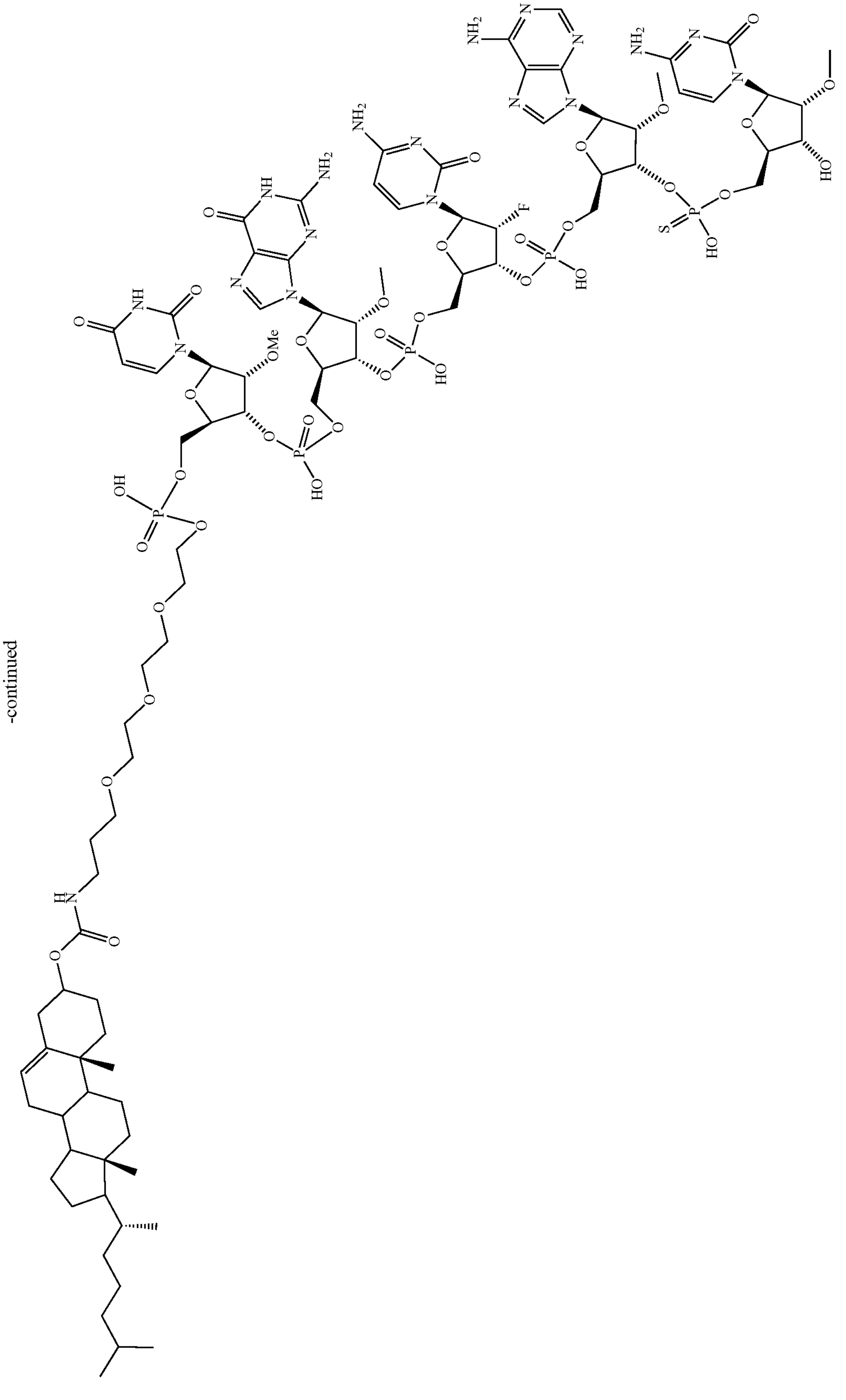
CMPD-004-005

1. CMPD-004-002

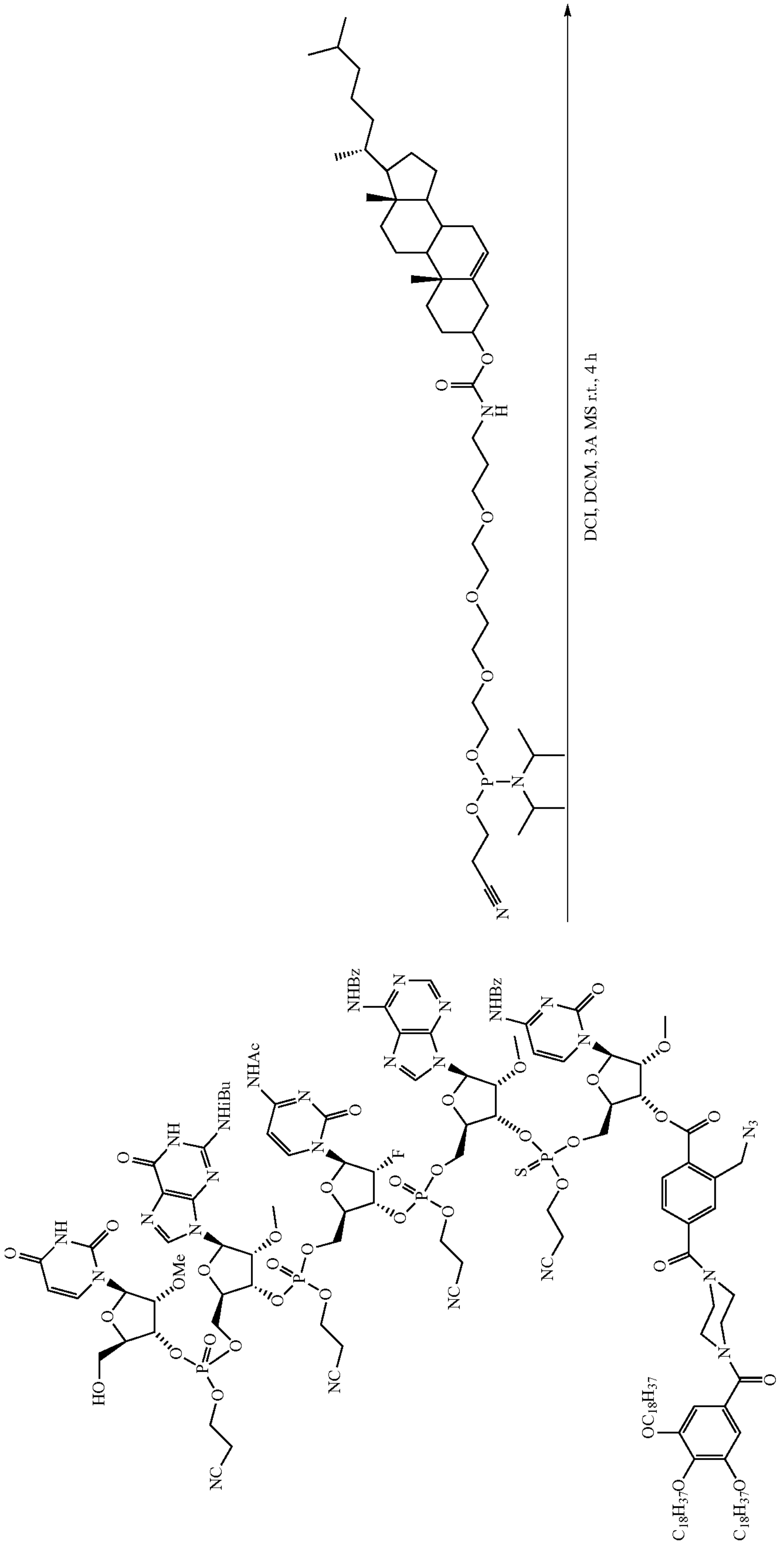
CMPD-004-001

-continued
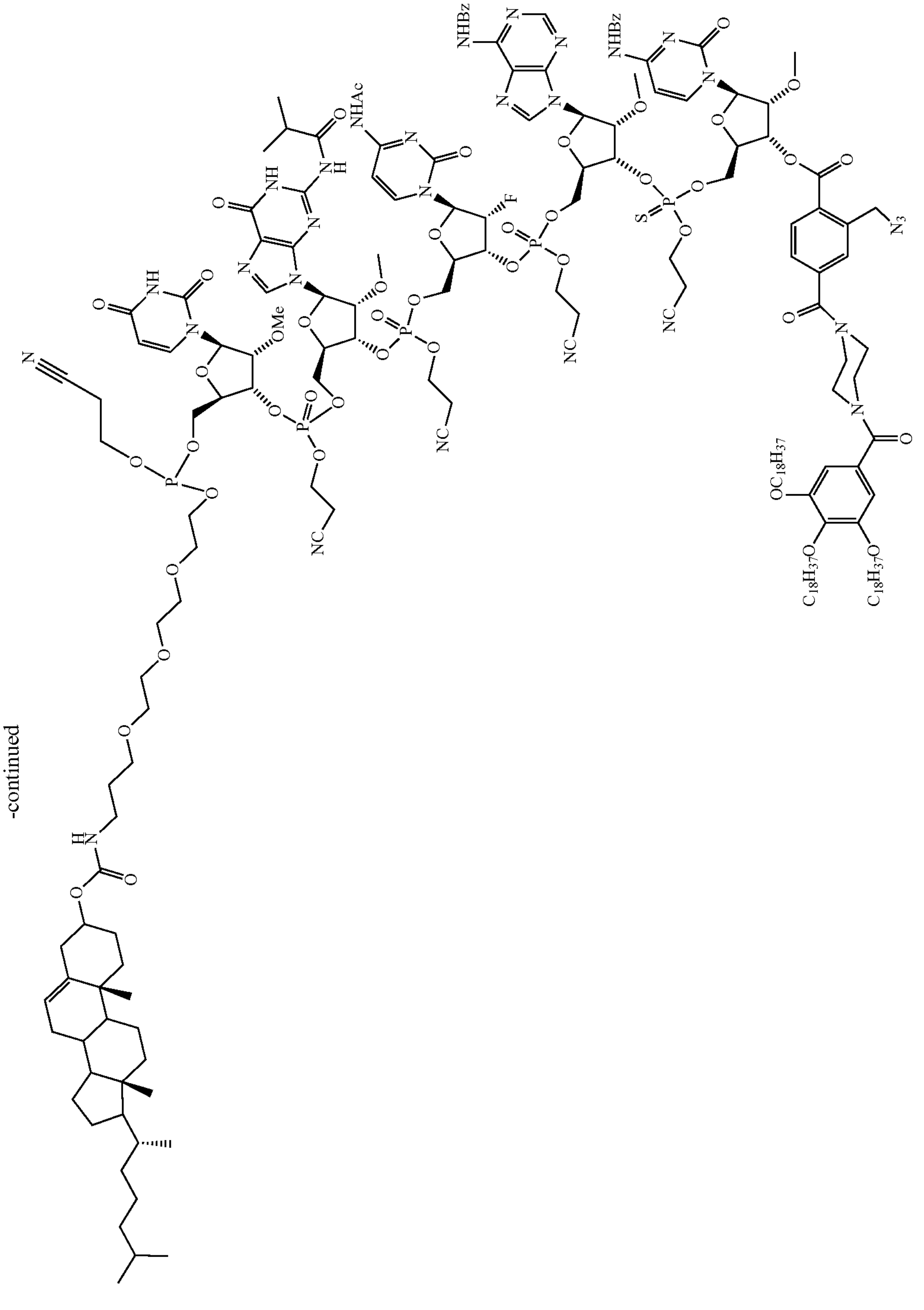
CMPD-004-002

CMPD-004-001 was dried by co-evaporated with pyridine three times, toluene three times respectively. To a solution of CMPD-004-001 (50 mg, 0.015 mmol, 1.0 equiv) in 0.5 mL of dichloromethane with an inert atmosphere of Argon and 3A molecular sieves was added the solution of 5'-Cholesteryl-TEG Phosphoramidite (24.7 mg, 0.03 mmol, 2.0 equiv) in dichloromethane (0.1 mL) and 4,5-Dicyanoimidazole (2.67 mg, 0.02 mmoL, 1.5 equiv) at room temperature. The reaction solution was stirred 4 h at room temperature. Then it was used at next step without further purification.

2. CMPD-004-003

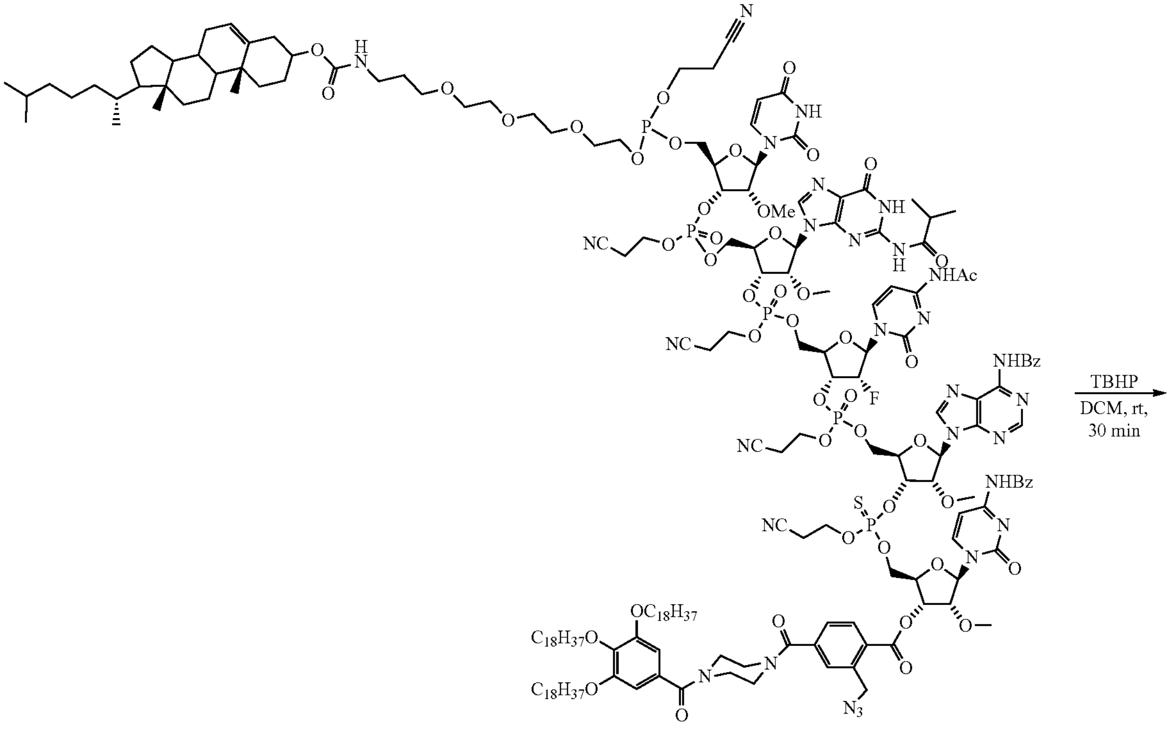

CMPD-004-002

-continued

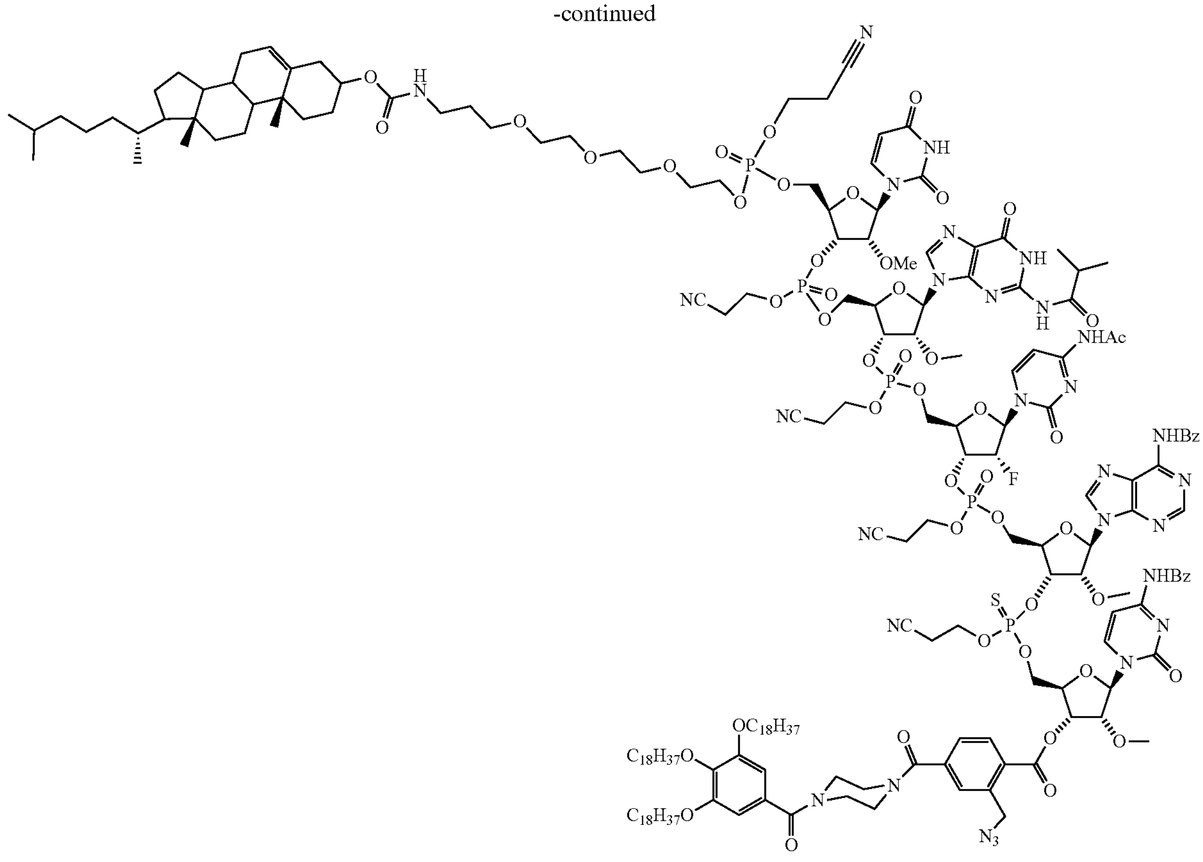

CMPD-004-003

The resulting solution of CMPD-004-002 with an inert atmosphere of Argon was added tert-butyl hydroperoxide (2.7 mg, 0.03 mmol, 2.0 equiv) at room temperature. The resulting solution was stirred for 30 min at room temperature. The 3A molecular sieves were removed by filtration, and the filtrate was precipitated by addition of acetonitrile. The solid was collected by filtration.

3. CMPD-004-004
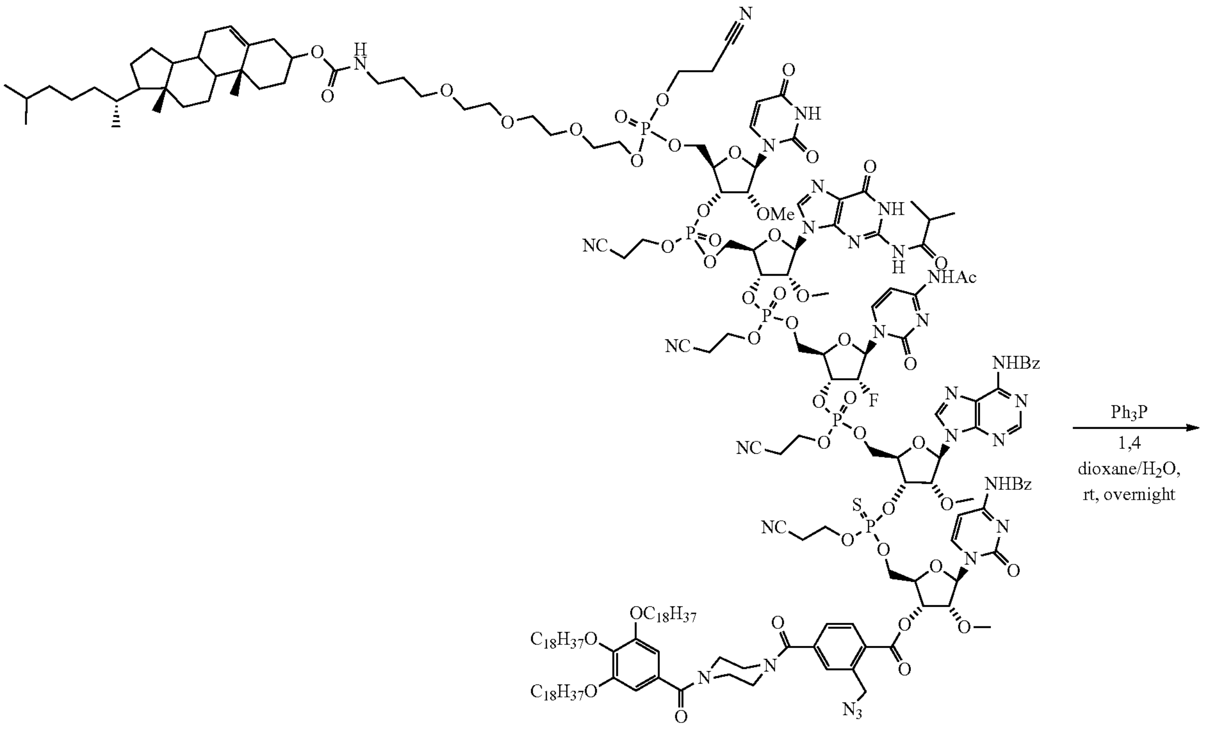
CMPD-004-003
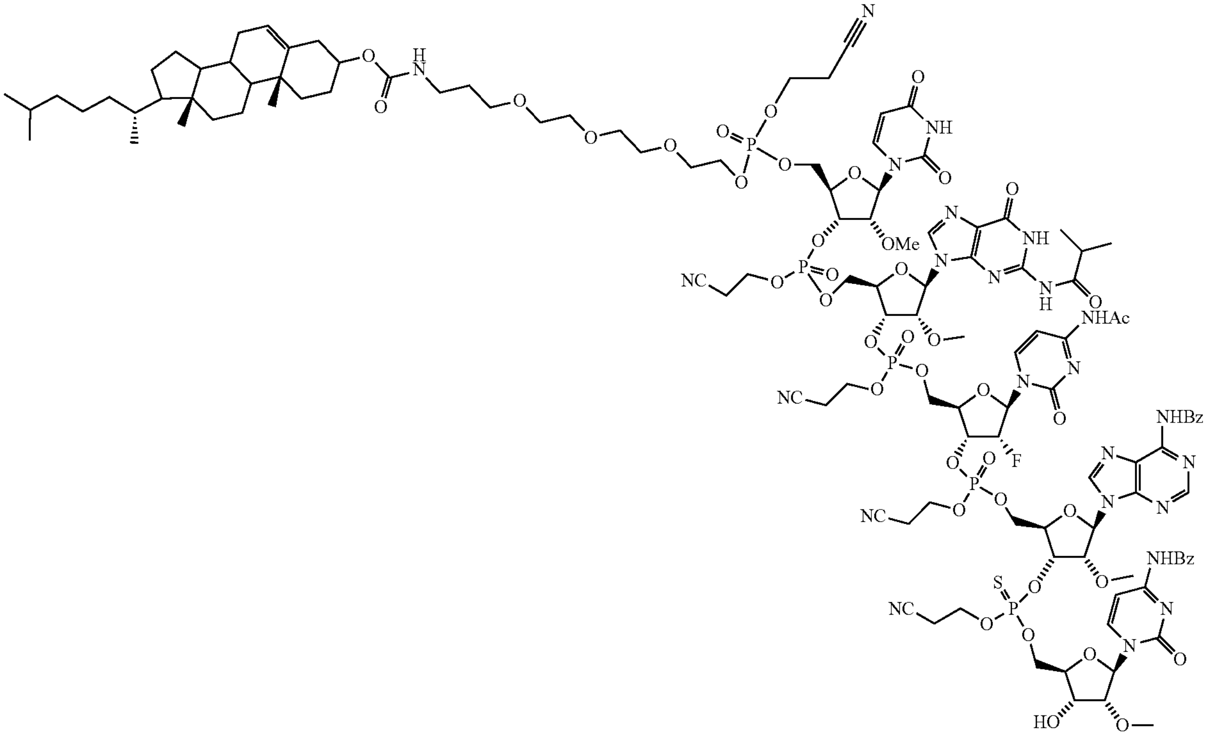
CMPD-004-004
To a solution of CMPD-004-003 (50 mg, 0.012 mmol, 1.0 equiv) in 1.0 mL of dioxane/water (10/1, v/v) with an inert atmosphere of Argon, is added triphenylphosphine (13 mg, 0.05 mmol, 4.0 equiv) at room temperature. The reaction solution is stirred overnight at room temperature, and is monitored by LCMS. The crude product is purified by Flash-Prep-HPLC on a C18 column with acetonitrile/water.
4. CMPD-004-005

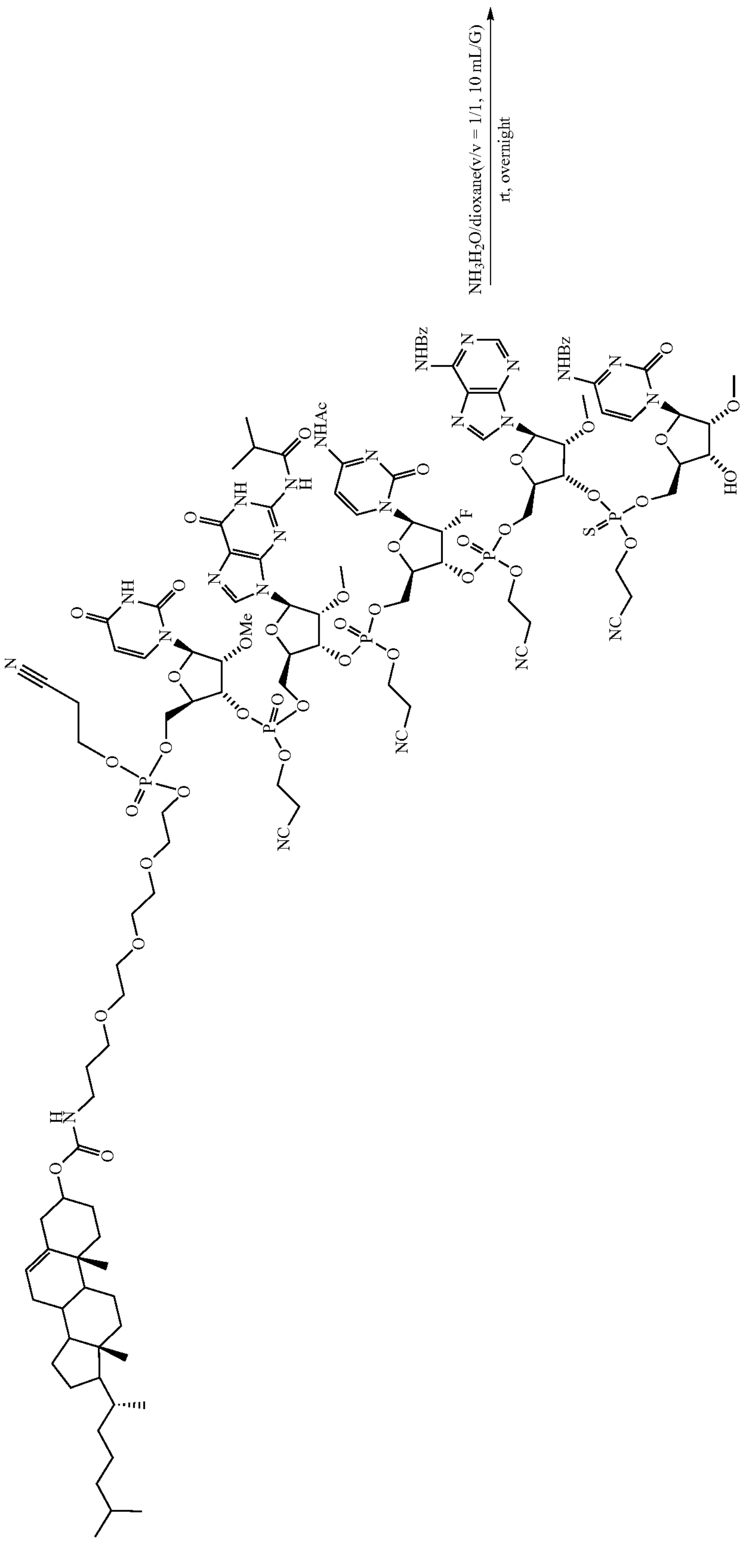
CMPD-004-004

-continued
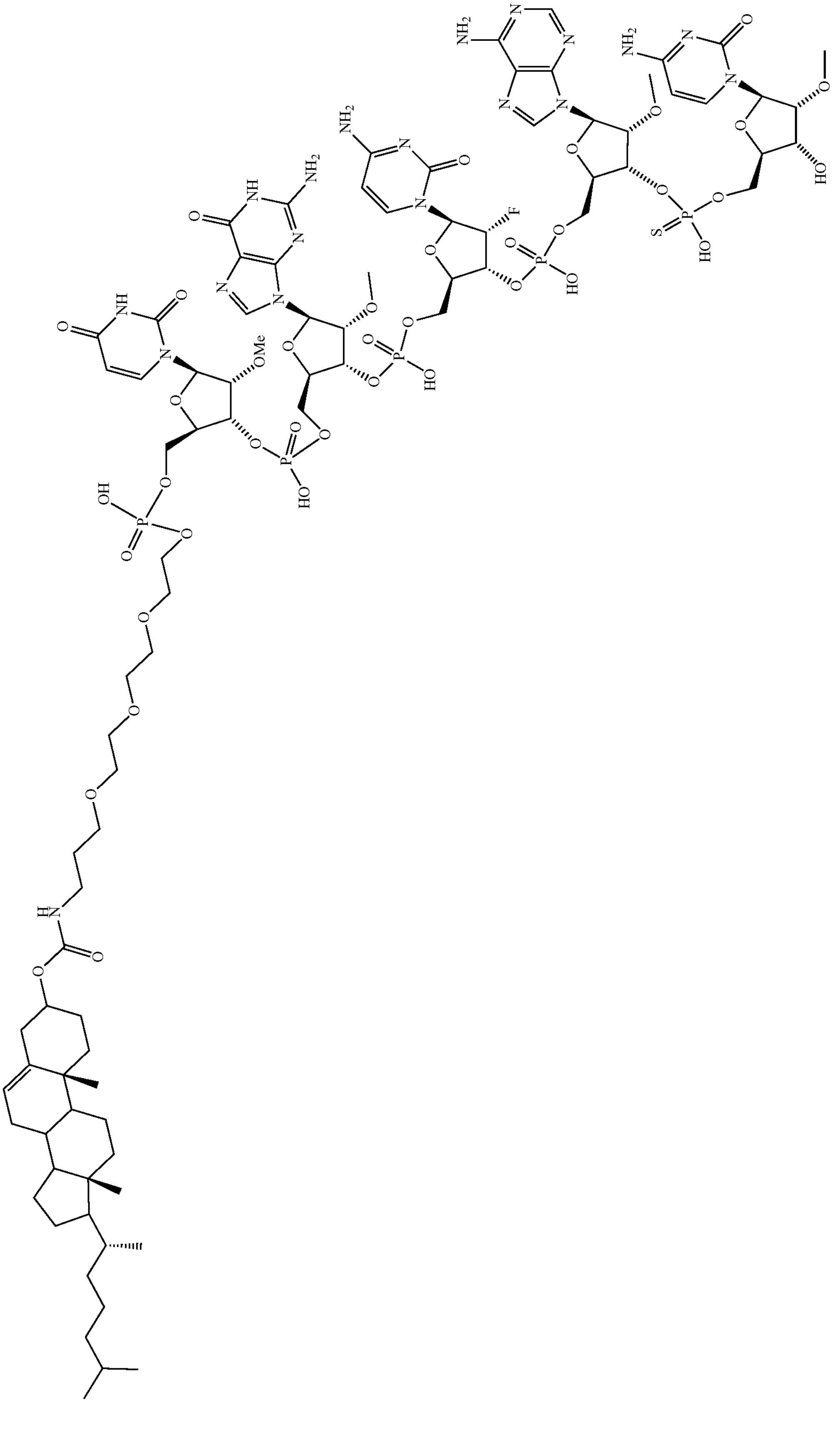
CMPD-004-005

To a solution of CMPD-004-004 (50 mg 0.017 mmoL, 1 equiv) in 0.5 mL of Ammonium hydroxide/dioxane (1/1, v/v) with an inert atmosphere of Argon is stirred 12 h at room temperature. The reaction is monitored by LCMS. MS m/z $[M+H]^+$ (ESI):

Example 8: Synthesis of 3'-cholesterol Conjugate of a Pentamer Oligonucleotide

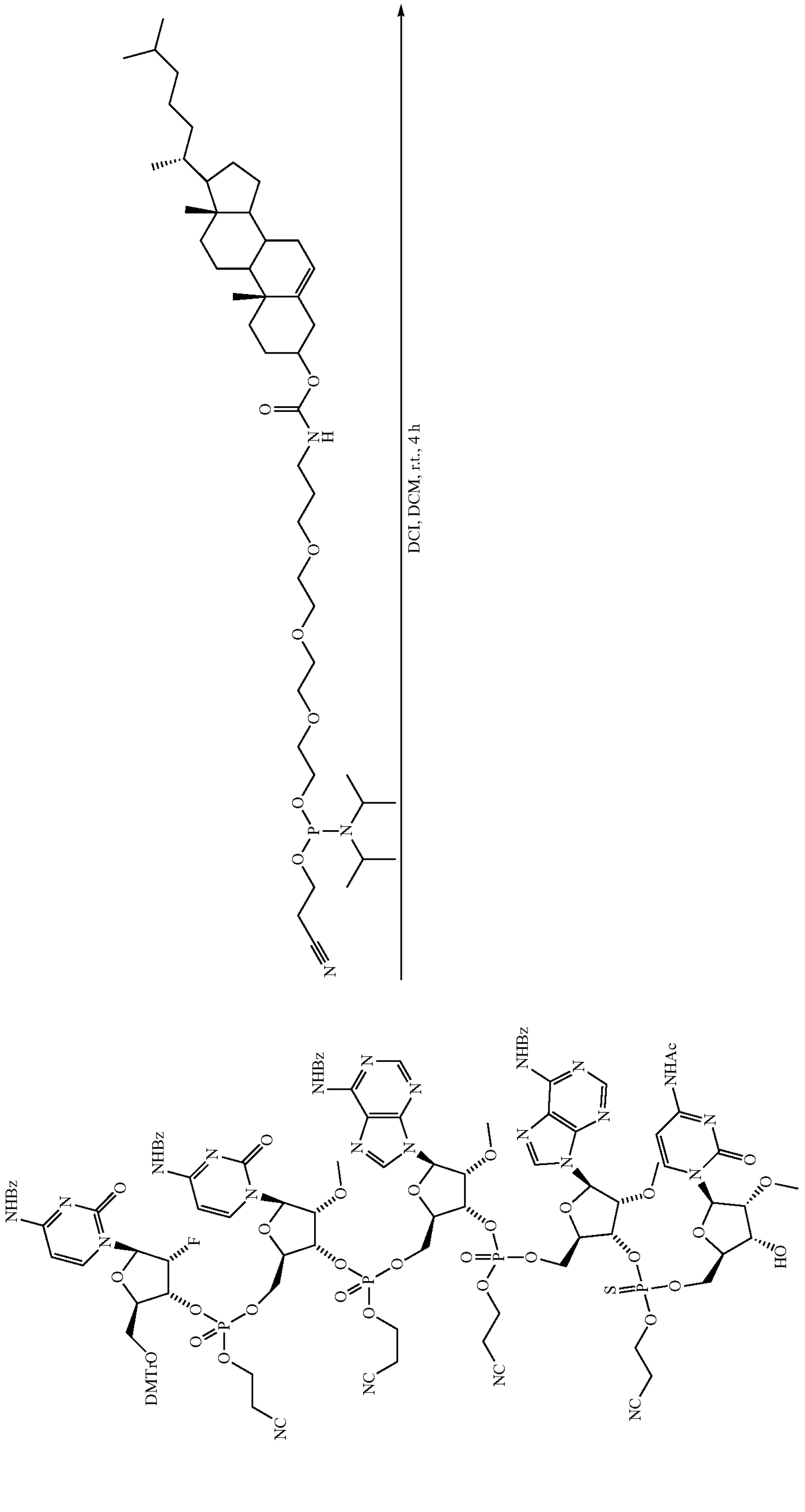
CMPD-005-001

-continued
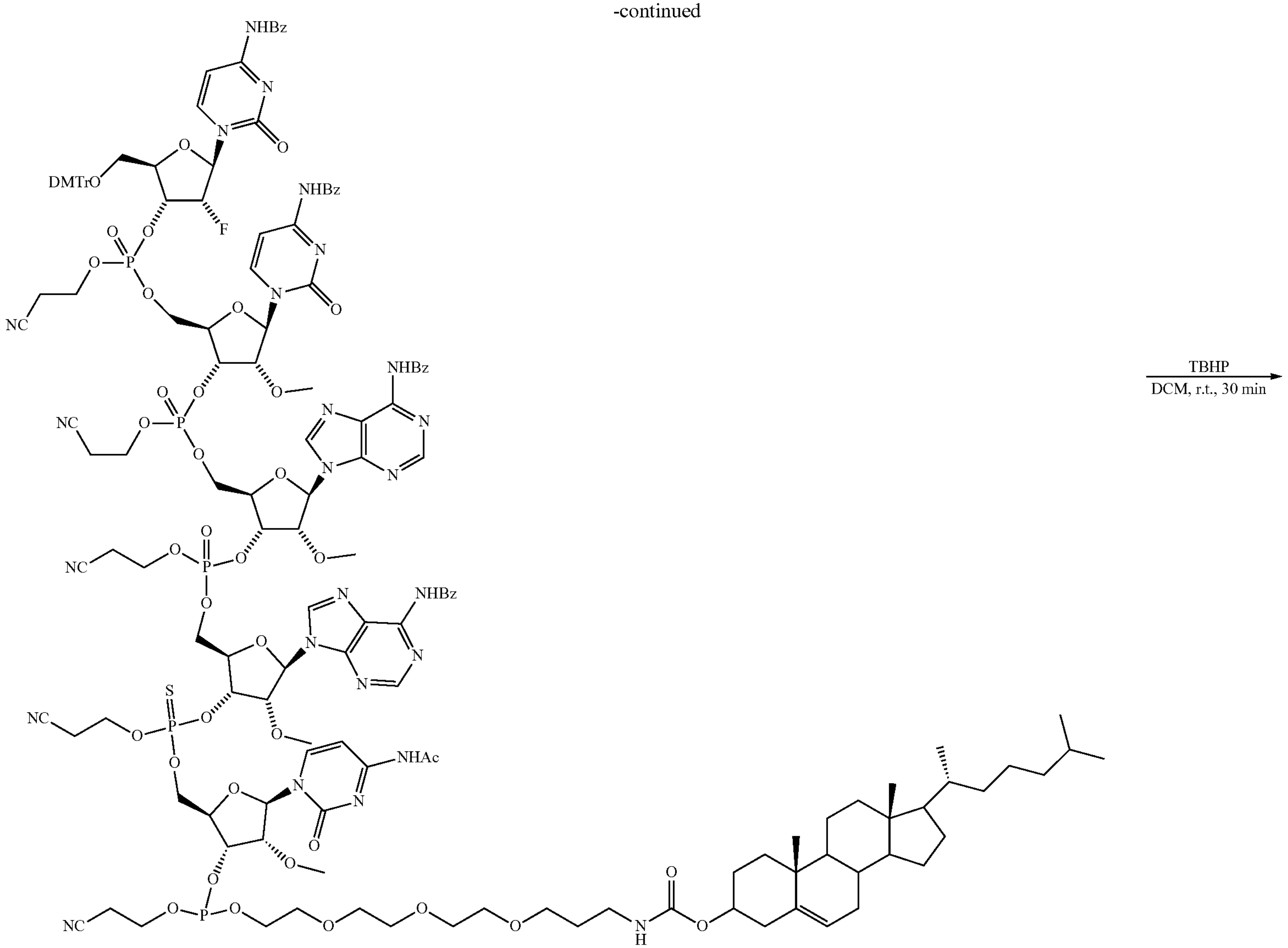
CMPD-005-002

-continued
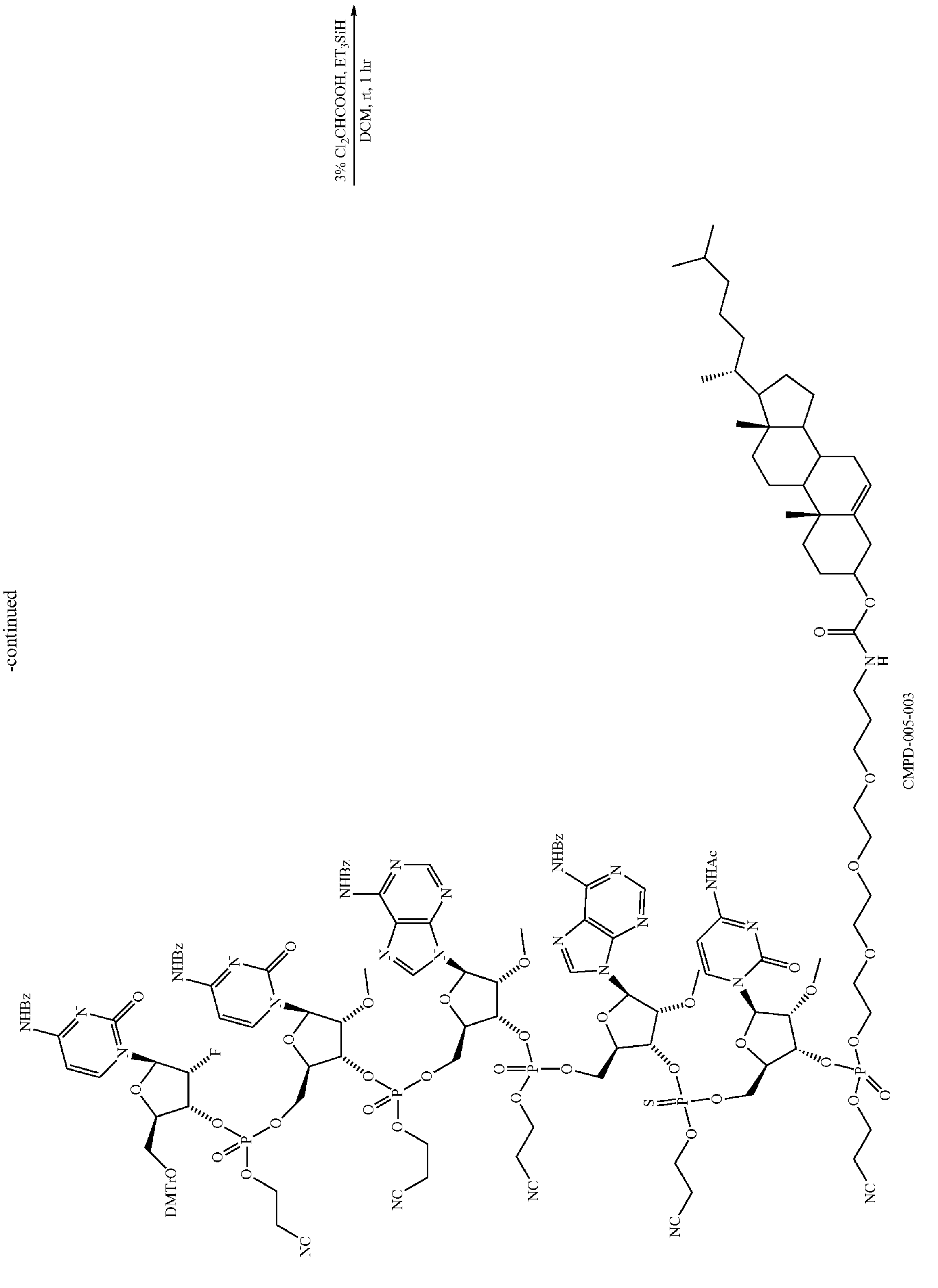
CMPD-005-003

-continued
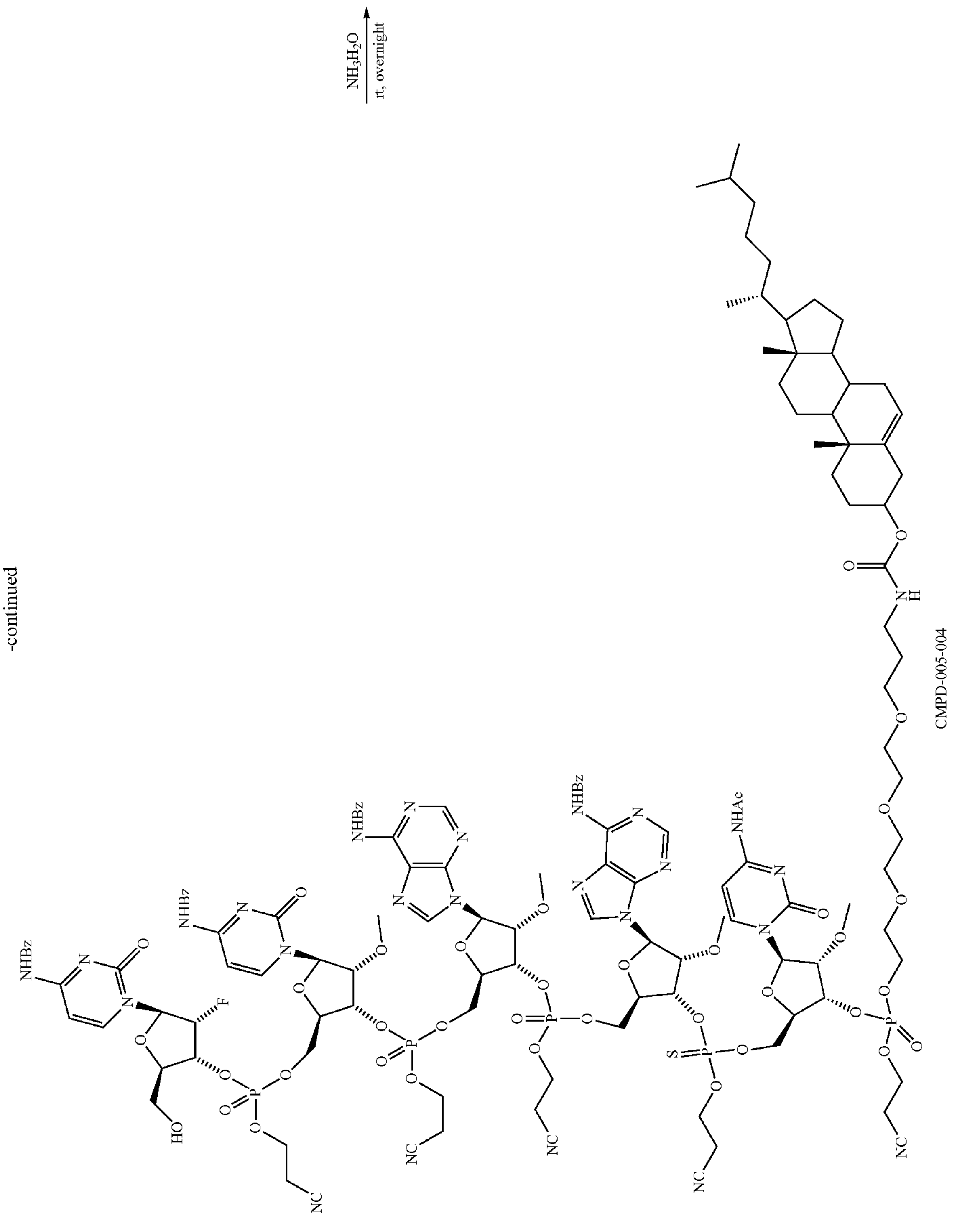
CMPD-005-004

-continued
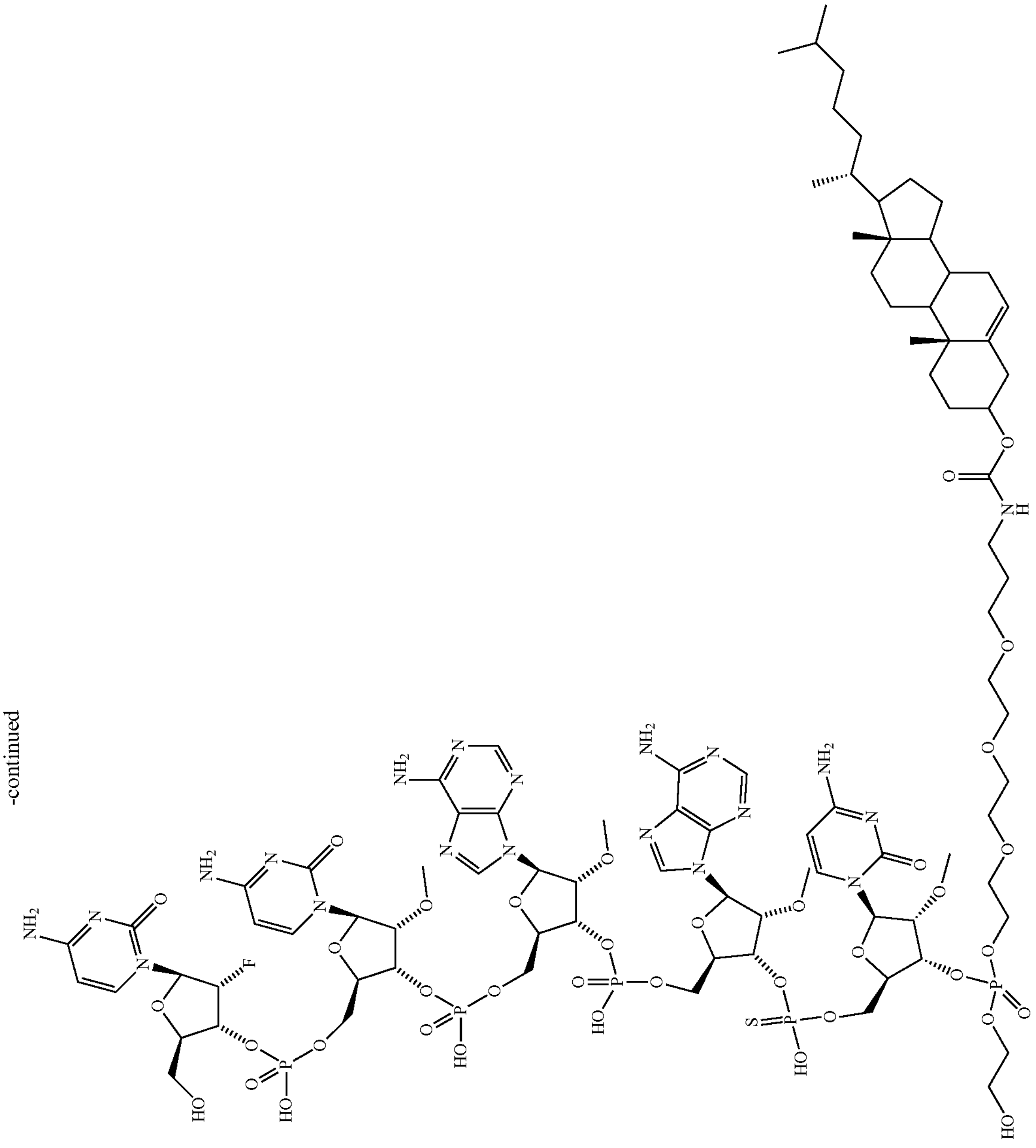
CMPD-005-005

1. CMPD-005-002

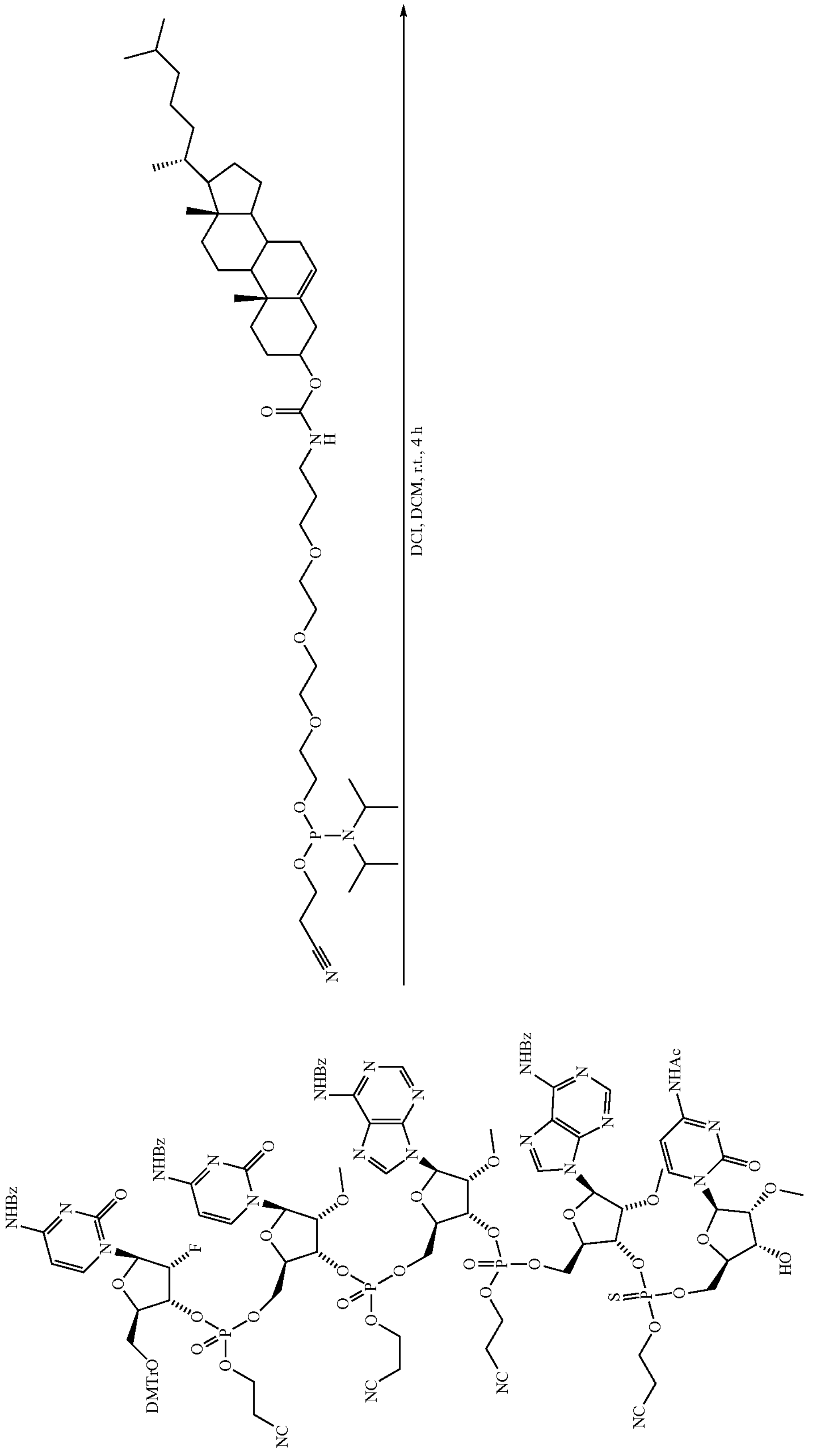
CMPD-005-001

-continued
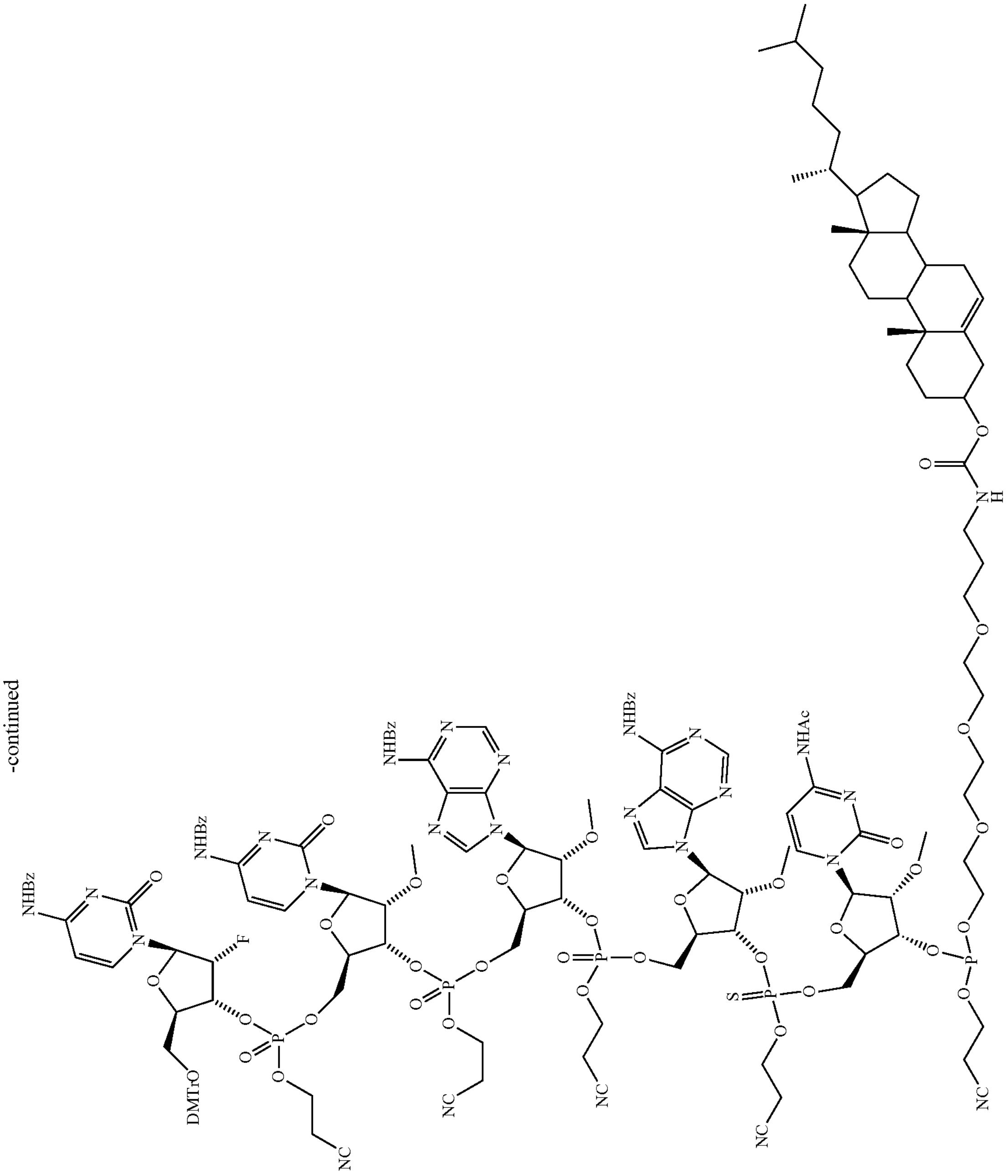
CMPD-005-002

CMPD-005-001 is dried by co-evaporated with pyridine three times, toluene three times respectively. To a solution of CMPD-005-001 (50 mg, 0.02 mmol, 1.0 eq.) in 1 mL of dichloromethane with an inert atmosphere of Argon and 3A molecular sieves was added 5'-Cholesteryl-TEG Phosphoramidite (33 mg, 0.04 mmol, 2.0 eq.) and 4,5-Dicyanoimidazole (7.1 mg, 0.06 mmoL, 3.0 eq.) at room temperature. The reaction solution was stirred 4 h at room temperature and used at next step without further purification. MS m/z $[M/2+H]^+$ (ESI): 1640

2. CMPD-005-003

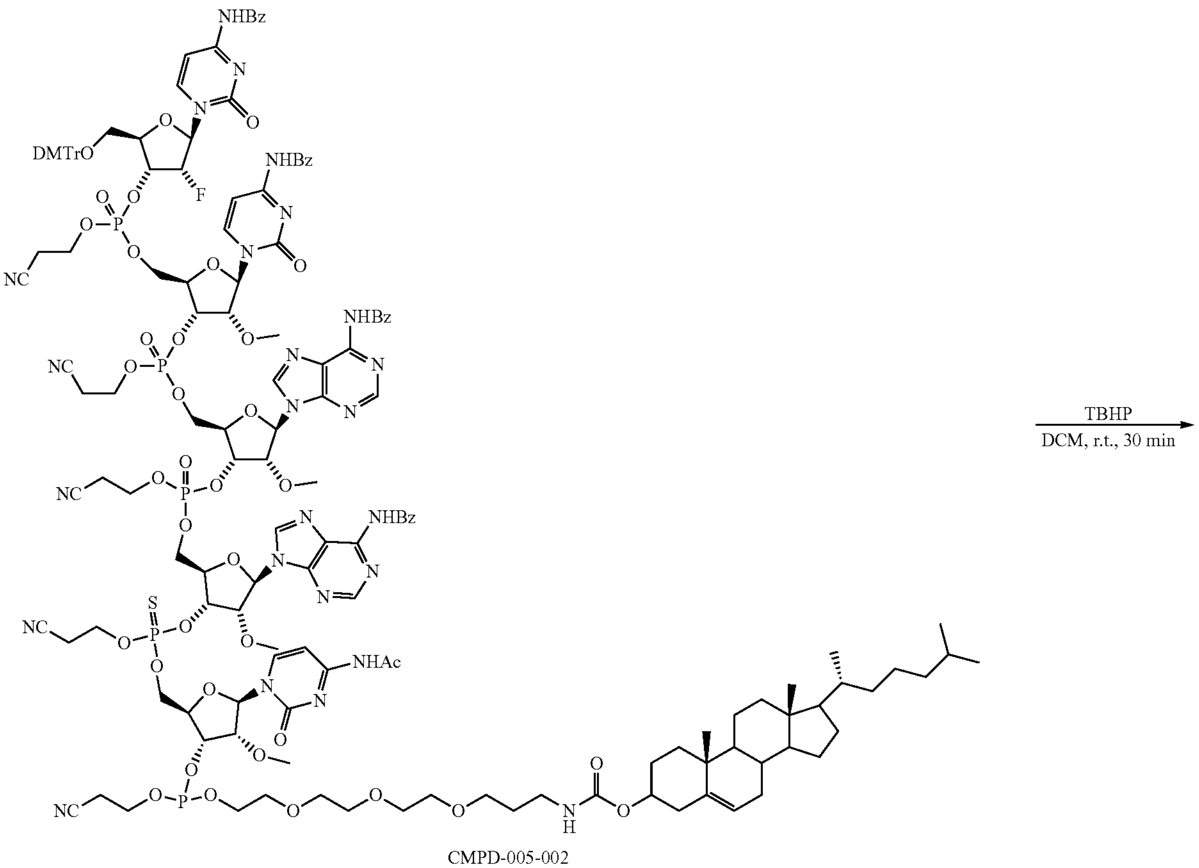

CMPD-005-002

-continued

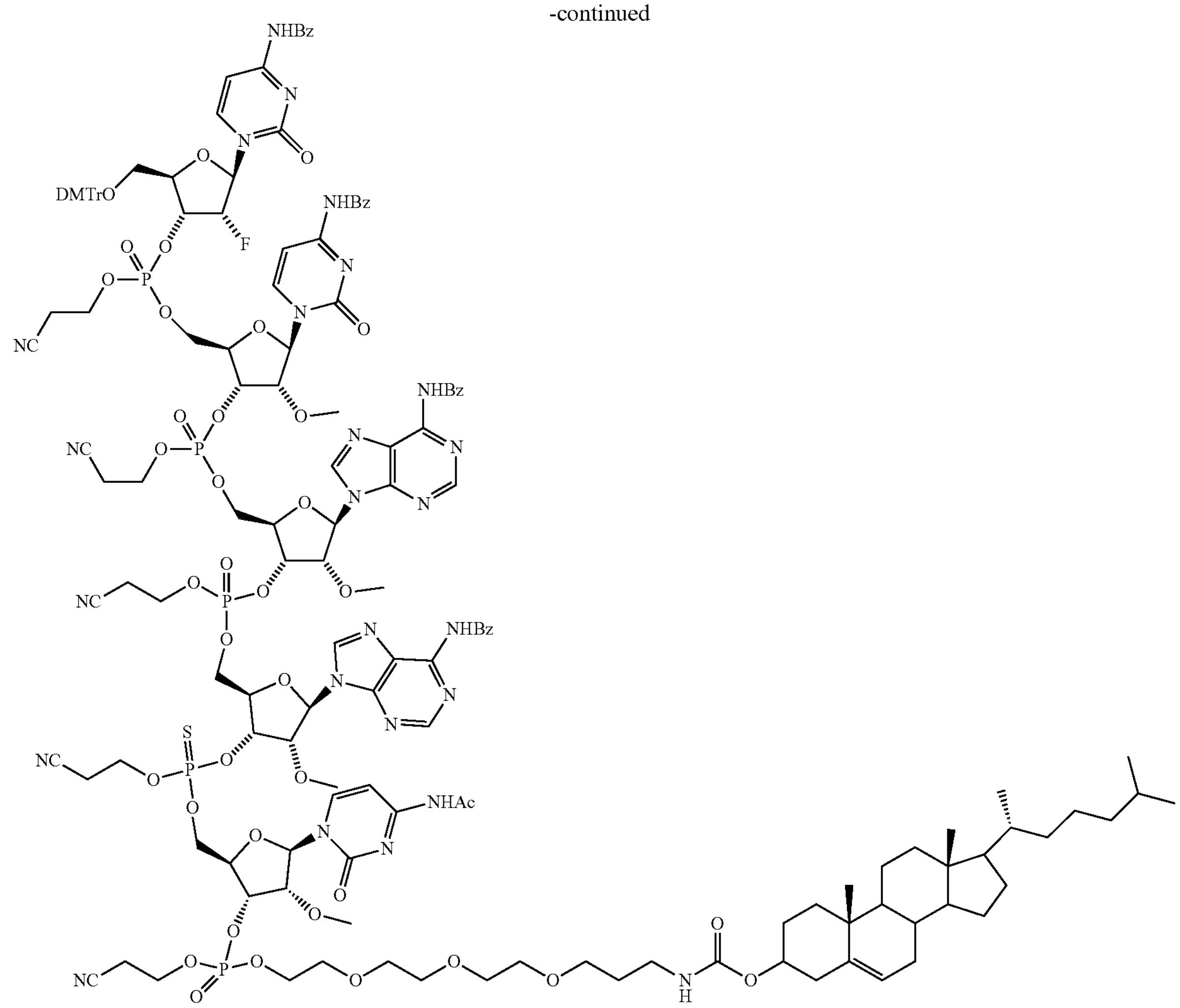

CMPD-005-003

The resulting solution of CMPD-005-002 (0.02 mmol, 1.0 eq.) with an inert atmosphere of Argon was added tert-Butyl hydroperoxide (13 mg, 0.1 mmol, 5.0 eq.) at room temperature. The resulting solution was stirred for 30 min at room temperature. 3A molecular sieve was retained in the reaction system and removed by the first filtration after oxidization. The filtrate was precipitated by addition of tert-Butyl methyl ether filtrated. PH-CMPD-005-003 is obtained as a white solid. MS m/z $[M/2+H]^+$ (ESI): 1648

3. CMPD-005-004
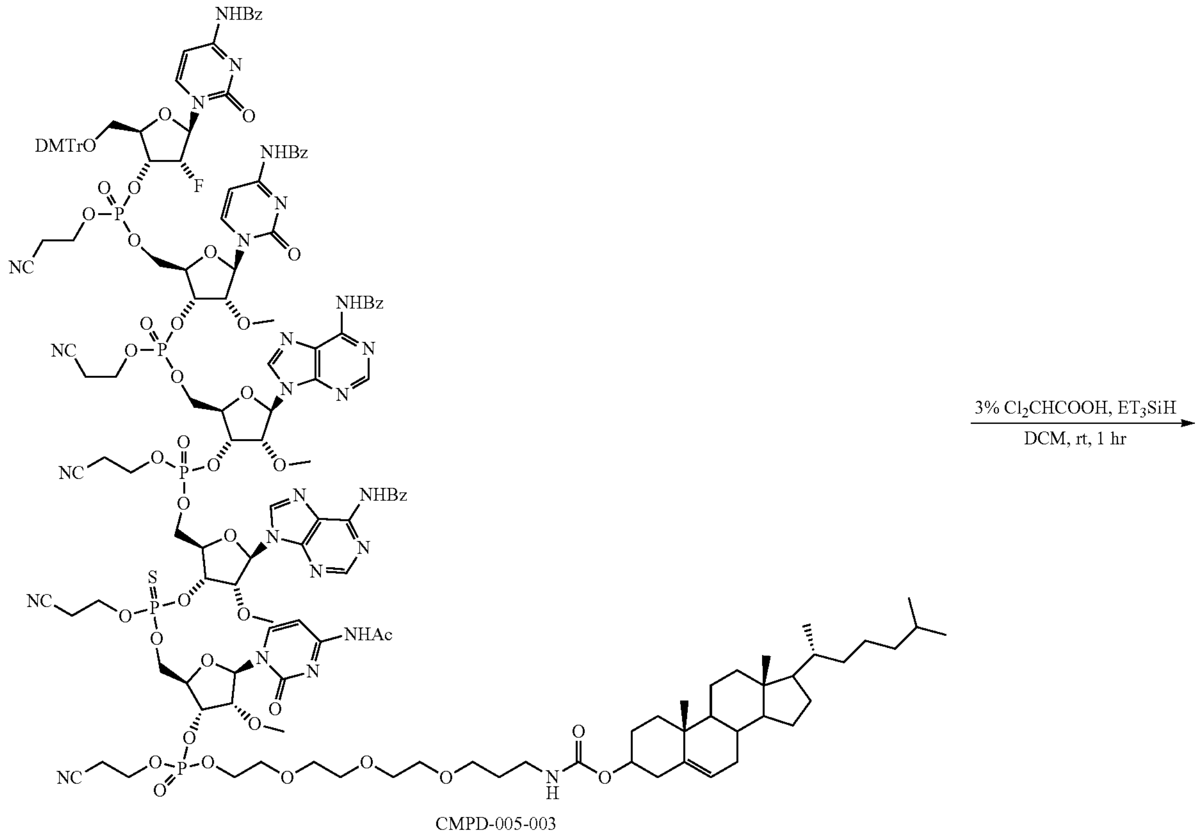
CMPD-005-003

-continued

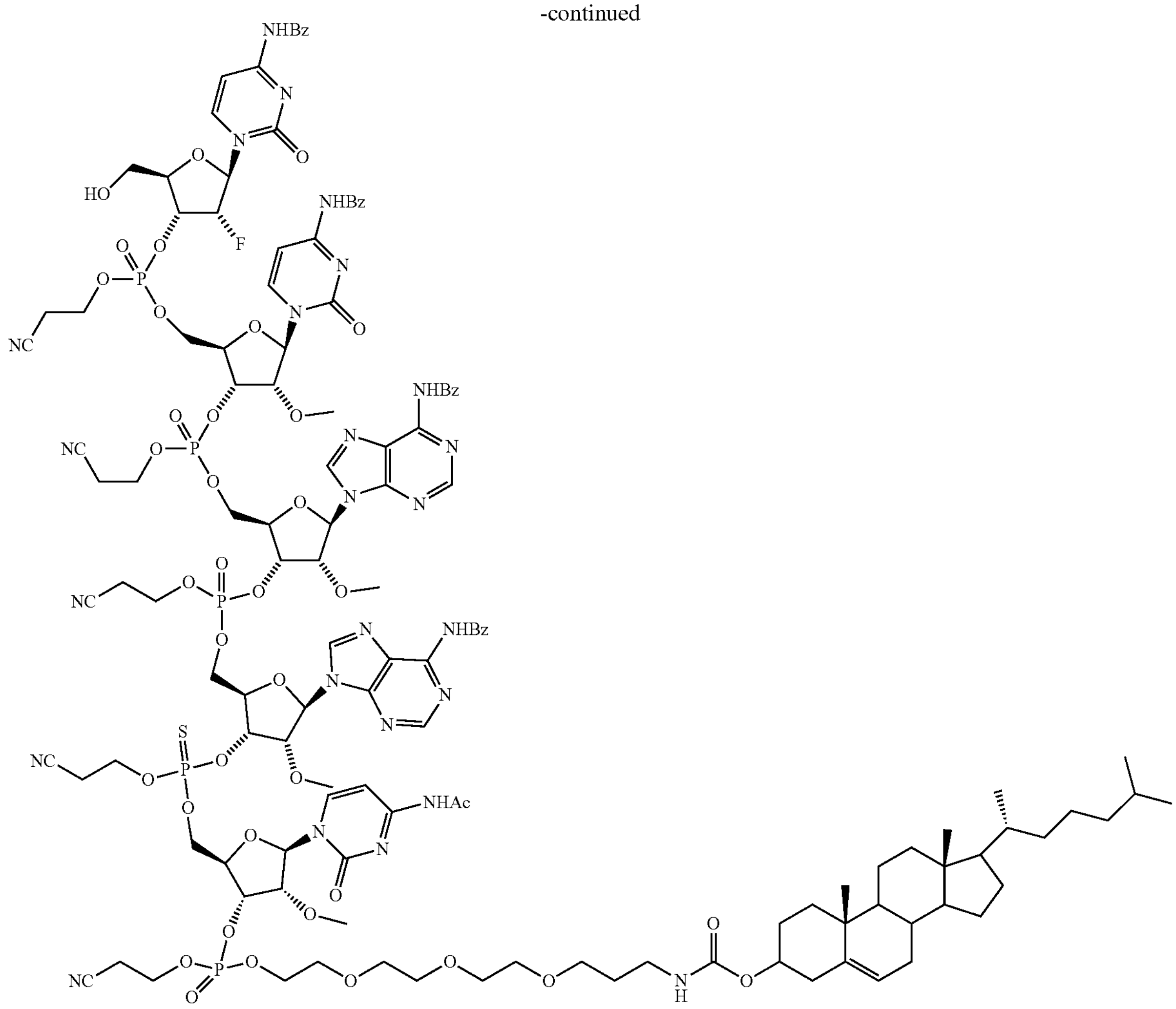

CMPD-005-004

To a solution of CMPD-005-003 (37 mg, 0.011 mmol, 1.0 eq.) in 1 mL of dichloromethane was added 0.03 mL of dichloroacetic acid and triethylsilane (3.2 mg, 0.027 mmol, 2.5 eq.). The resulting solution was stirred for 1 h at room temperature. The resulting solution was precipitated by tert-butyl methyl ether, and the solid was collected by filtration. CMPD-005-004 is obtained as a white solid. MS m/z $[M/2+H]^+$ (ESI): 1496.

4. CMPD-005-005
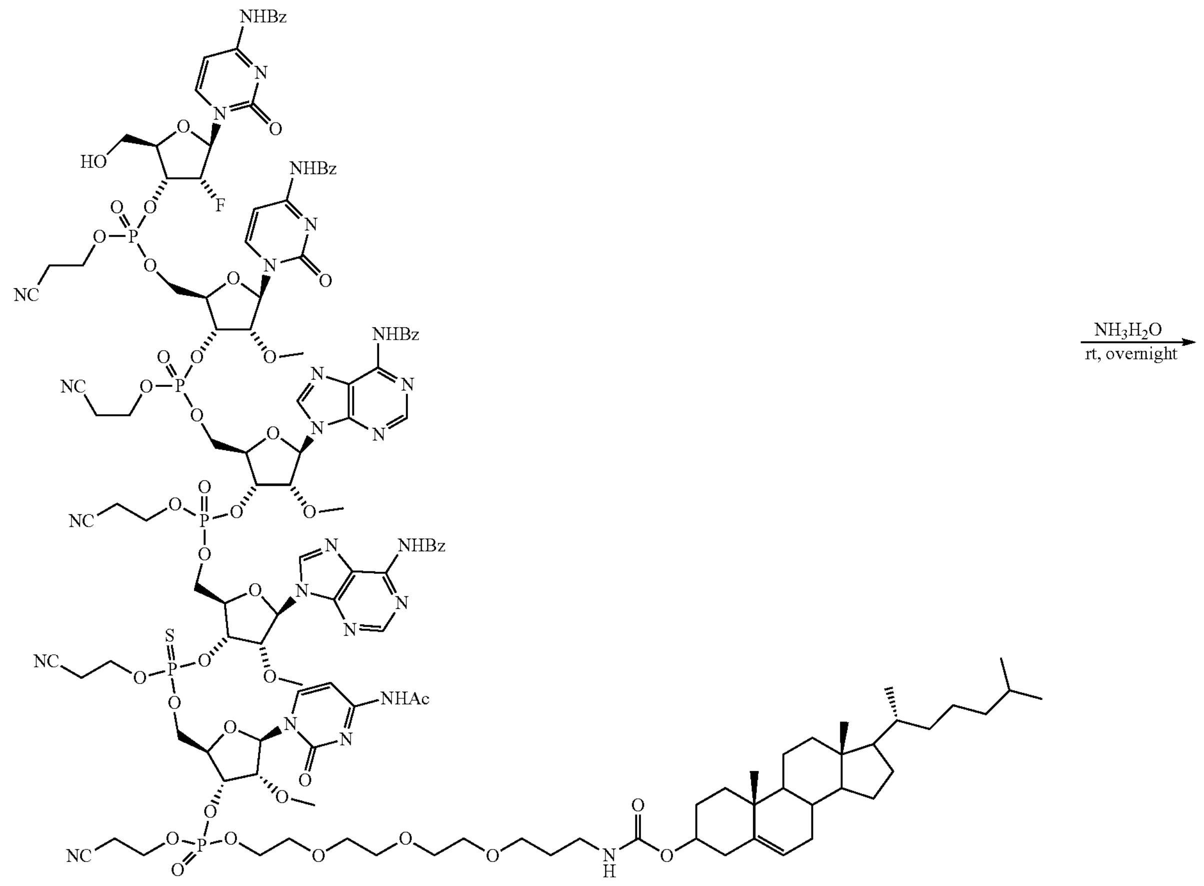
CMPD-005-004

-continued
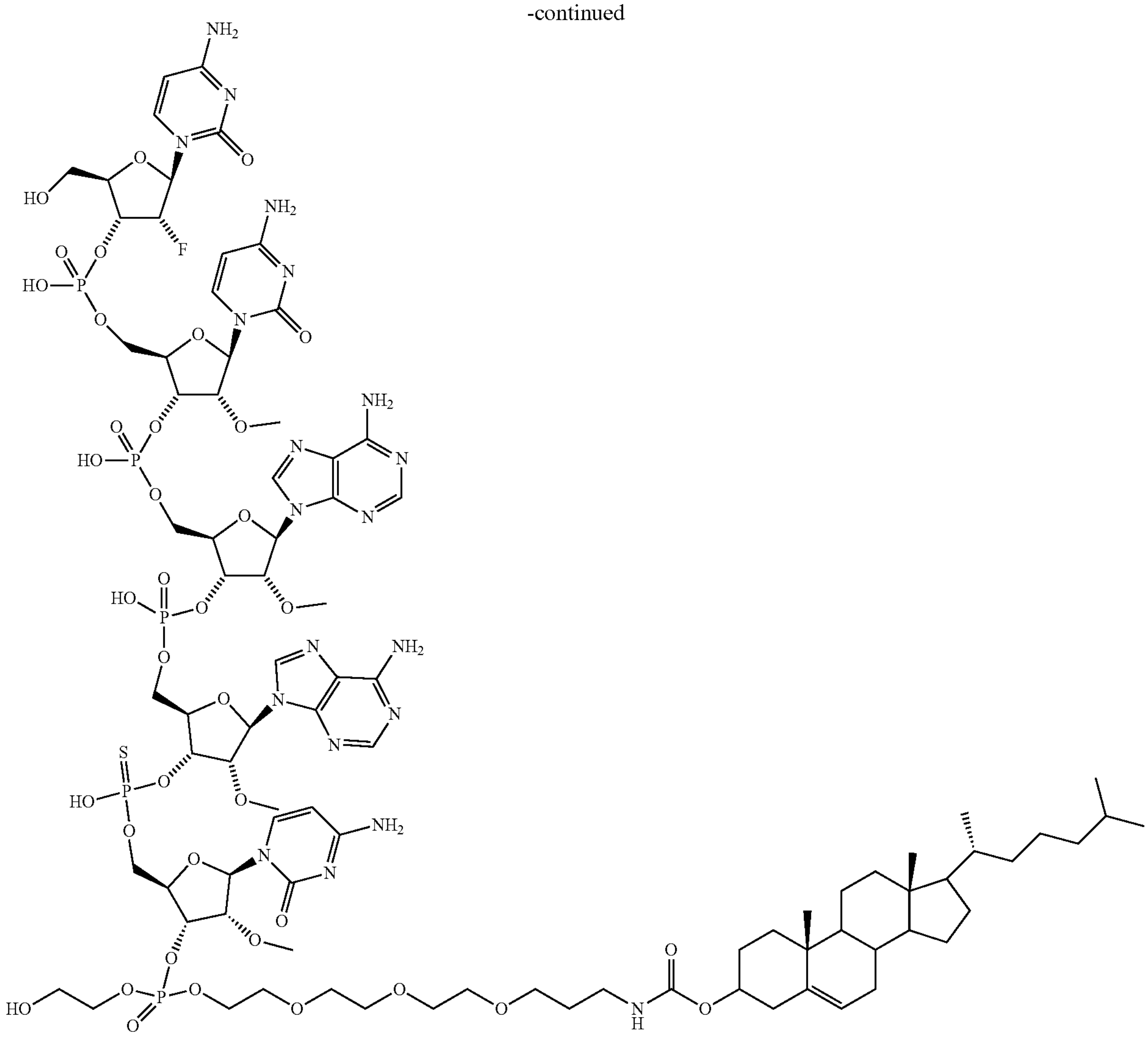
CMPD-005-005
A mixture of CMPD-005-004 (0.008 mmol, 1.0 eq.) in 3 mL of Ammonium hydroxide was stirred for overnight at room temperature and washed with 3×5 mL of dichloromethane. The aqueous phase was concentrated under reduced pressure. PH-CMPD-005-005 is obtained as a white solid. MS m/z $[M/2+H]^+$ (ESI): 1135.

Example 9: Synthesis of CPG-Nucleoside Cleavable by Azidomethyl Chemistry
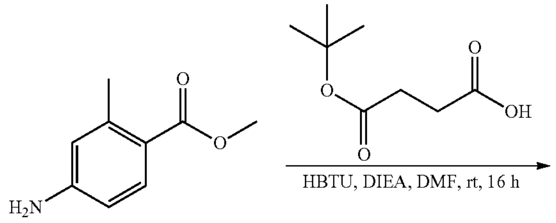
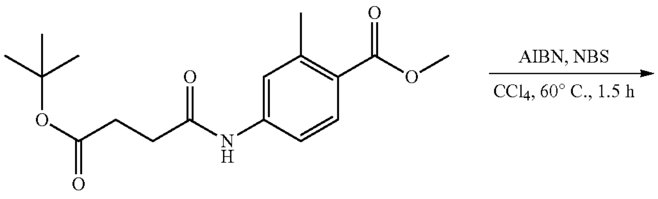
CMPD-006-001
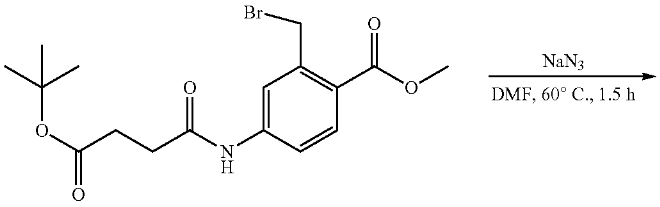
CMPD-006-002
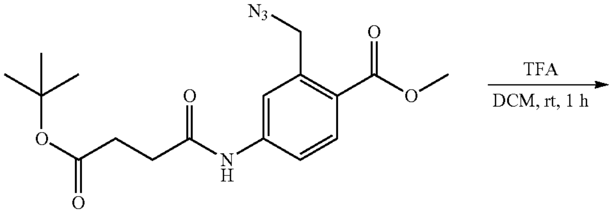
CMPD-006-003
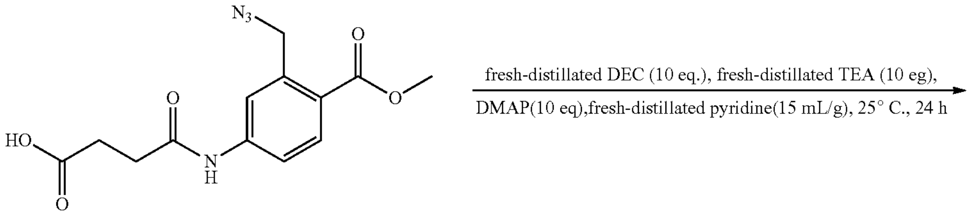
CMPD-006-004
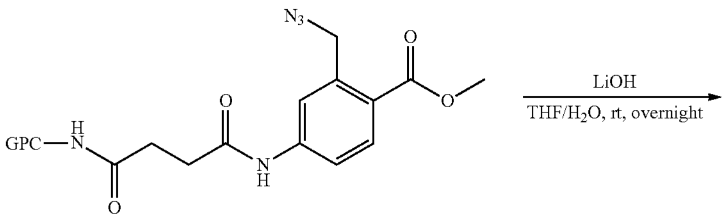
CMPD-006-005

-continued

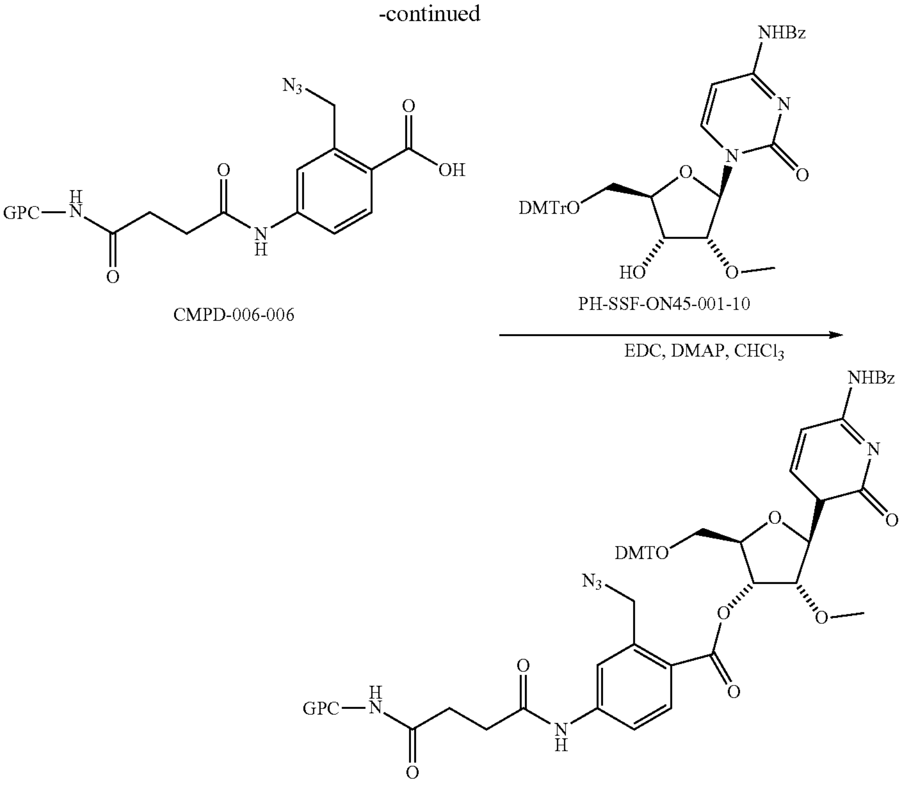

CMPD-006-006

PH-SSF-ON45-001-10

CMPD-006-007

1. CMPD-006-001

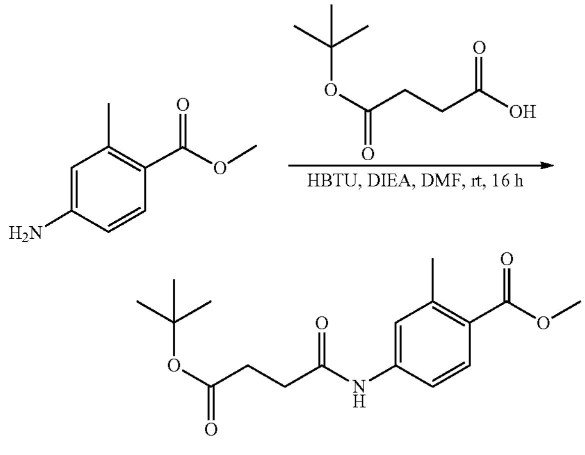

CMPD-006-001

To a solution of 4-(tert-butoxy)-4-oxobutanoic acid (5 g, 28.73 mmol, 1.1 equiv) in 30 mL of N, N-dimethylformamide with an inert atmosphere of nitrogen was added O-Benzotriazole-N, N, N-etramethyl-uronium-hexafluorophosphate (12.6 g, 33.33 mmol, 1.1 equiv), N, N-diisopropylethylamine (15 mL, 90.9 mmol, 3.00 equiv) at room temperature. After 5 min, a solution of methyl 4-amino-2-methylbenzoate (5 g, 30.3 mmol, 1.00 equiv) in 20 mL of N, N-dimethylformamide was added at room temperature. The resulting solution was stirred for 16 h at room temperature then diluted with 200 ml of ethyl acetate, washed with 2×100 mL of saturated sodium chloride. The organic phase was dried over anhydrous sodium sulfate, filtered, and concentrated under reduced pressure. The crude product was purified by Flash-Prep-HPLC with the following conditions: Column, C18 silica gel; mobile phase, water with 0.04% $NH_4HCO_3$ and acetonitrile (30% acetonitrile up to 100% in 15 min and hold 100% for 4 min); Detector, UV 254 nm. The fractions (00 mL) was diluted with 1000 mL of dichloromethane and dried over anhydrous sodium sulfate. The solid was filtered out. The filtrate was concentrated under reduced pressure. 6 g of CMPD-006-001 was obtained as brown oil and confirmed by LCMS. MS m/z $[M+H]^+$ (ESI): 322.

2. CMPD-006-002

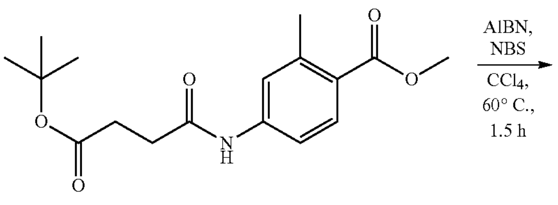

CMPD-006-001

-continued

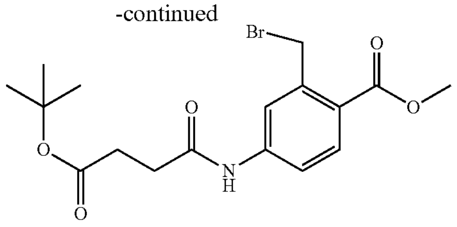

CMPD-006-002

To a solution of CMPD-006-001 (5.5 g, 17.13 mmol, 1.0 equiv) in 60 mL of carbon tetrachloride with an inert atmosphere of nitrogen was added 2,2'-Azobis(2-methylpropionitrile) (1.68 g, 10.28 mmol, 0.6 equiv), N-Bromosuccinimide (4.56 g, 25.71 mmol, 1.5 equiv) in order at 25° C. The resulting solution was dried over anhydrous sodium sulfate, filtered, and concentrated under reduced pressure. The crude product was purified by Flash-Prep-HPLC with the following conditions: Column, C18 silica gel; mobile phase, water with 0.04% $NH_4HCO_3$ and acetonitrile (30% acetonitrile up to 100% in 15 min and hold 100% for 4 min); Detector, UV 254 nm. The fractions (500 mL) was diluted with 600 mL of dichloromethane and dried over anhydrous sodium sulfate. The solid was filtered out. The filtrate was concentrated under reduced pressure. 2.5 g of CMPD-006-001 is obtained as brown oil and confirmed by LCMS. MS m/z $[M+H]^+$ (ESI): 400.

3. CMPD-006-003

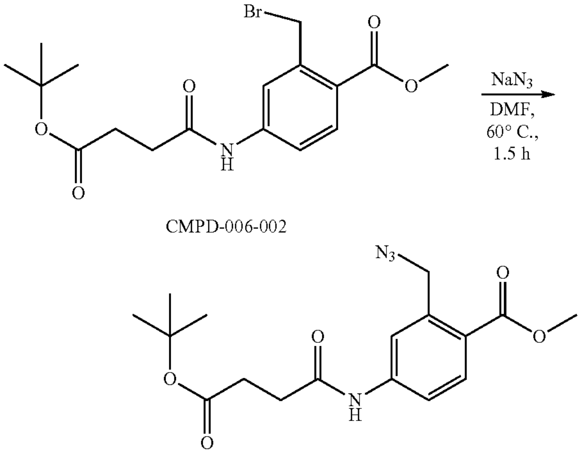

CMPD-006-002

CMPD-006-003

To a solution of CMPD-006-002 (1.5 g, 3.76 mmol, 1.0 equiv) in 20 mL of N, N-dimethylformamide with an inert atmosphere of nitrogen was added sodium azide (0.73 g, 11.28 mmol, 3.0 equiv) at 25° C. The resulting solution was stirred for 1.5 h at 60° C. then diluted with 100 ml of dichloromethane, washed with 1×100 mL of saturated sodium bicarbonate and 1×100 mL of saturated sodium chloride respectively (The aqueous phase is deal with Sodium hypochlorite solution). The organic phase was dried over anhydrous sodium sulfate, filtered, and concentrated under reduced pressure. The crude product was purified by Flash-Prep-HPLC with the following conditions: Column, C18 silica gel; mobile phase, water with 0.04% $NH_4HCO_3$ and acetonitrile (30% acetonitrile up to 100% in 15 min and hold 100% for 4 min); Detector, UV 254 nm. The fractions (200 mL) was diluted with 300 mL of dichloromethane and dried over anhydrous sodium sulfate. The solid is filtered out. The filtrate was concentrated under reduced pressure. 1.1 g of CMPD-006-003 was obtained as yellow oil and confirmed by LCMS. MS m/z $[M+H]^+$ (ESI): 363.

4. CMPD-006-004

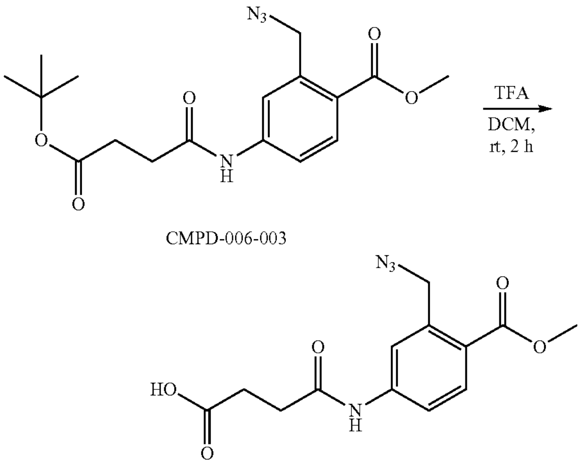

CMPD-006-003

CMPD-006-004

To a solution of CMPD-006-003 (500 mg, 1.38 mmol, 1.0 equiv) is added 5 mL of dichloromethane/trifluoroacetic acid (1:1) with an inert atmosphere of nitrogen at 0° C. The resulting solution is stirred for 2 h at 0° C. then concentrated under reduced pressure. The crude product purified by Flash-Prep-HPLC with the following conditions: Column, C18 silica gel; mobile phase, water with 0.05% TFA and acetonitrile (20% acetonitrile up to 100% in 15 min and hold 100% for 4 min); Detector, UV 254 nm. The fractions (200 mL) is diluted with 300 mL of dichloromethane and dried over anhydrous sodium sulfate. The solid is filtered out. The filtrate is concentrated under reduced pressure. 300 mg of CMPD-006-004 is obtained as yellow oil and confirmed by LCMS. MS m/z $[M+H]^+$ (ESI): 307.

5. CMPD-006-005

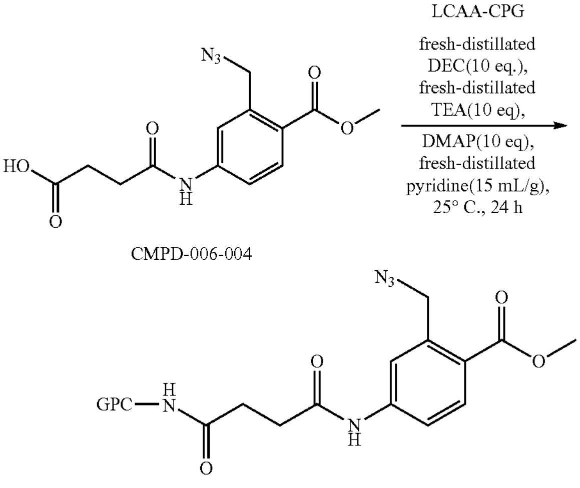

CMPD-006-004

CMPD-006-005

A mixture of CMPD-006-004 (48 mg, 0.156 mmol, 1.0 equiv), LCAA-CPG (400 mg), 4-Dimethylaminopyridine (192 mg, 1.56 mmol, 10.0 equiv), triethylamine (0.22 mL, 1.56 mmol, 10.0 equiv), (2-chloroethyl)diethylamine hydrochloride (244 mg, 1.56 mmol, 10 equiv)), and anhydrous pyridine (0.7 mL) are combined in a sealed, argon-purged 8 mL vial. The mixture is sonicated (ultrasound water bath) for 1-2 min and shaken at room temperature for 48 h in a shaking table. The solid is filtered off and washed successively with tetrahydrofuran, dichloromethane. 360 mg CMPD-006-005 is obtained as a yellow solid.

6. CMPD-006-006

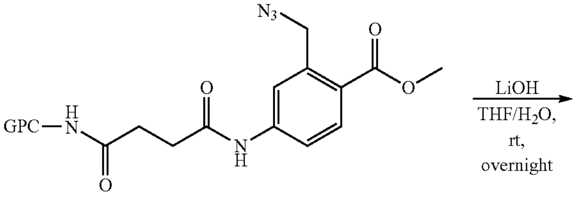

CMPD-006-005

-continued

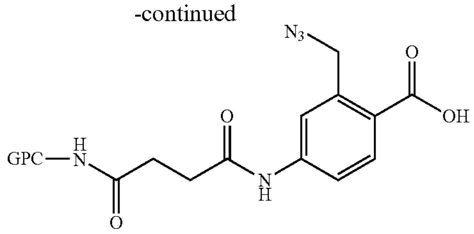

CMPD-006-006

A mixture of CMPD-006-005 (100 mg, 0.041 mmol, 1.00 equiv) in 0.4 mL of tetrahydrofuran/water (4:1) is added lithium hydroxide (6.9 mg, 0.166 mmol, 4.0 equiv) at room temperature. The mixture is shaken at room temperature for 16 h in a shaking table. The pH value of the solution is adjusted to 6 with hydrochloric acid (1 mol/L). The solid is filtered off and washed successively with water, tetrahydrofuran, dichloromethane and confirmed by LCMS. 80 mg CMPD-006-006 is obtained as off-white solid.

7. CMPD-006-007

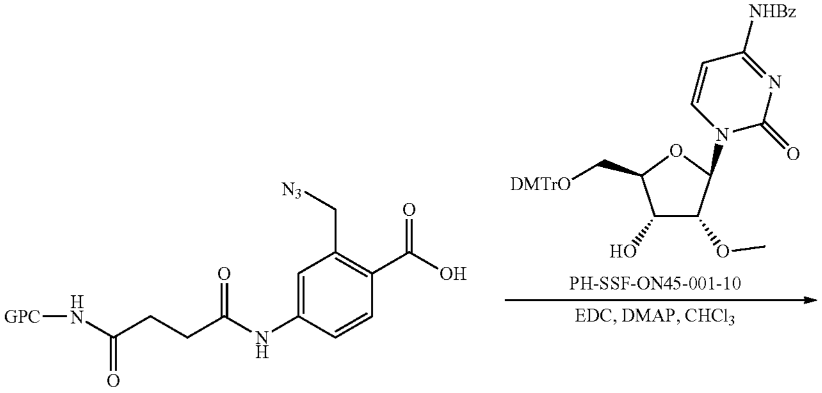

CMPD-006-006

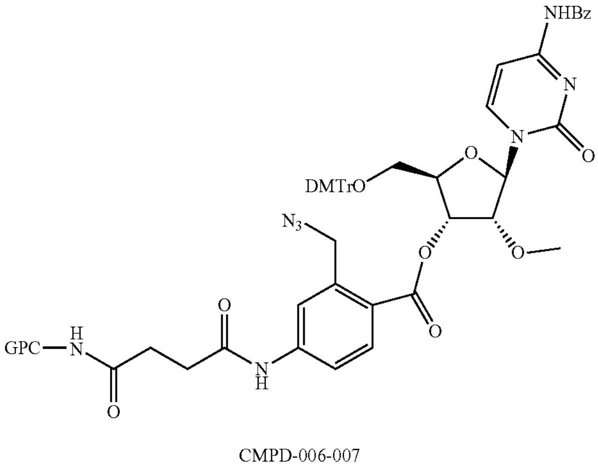

CMPD-006-007

A mixture of CMPD-006-006 (80 mg, 0.035 mmol, 1.00 equiv) in 0.4 mL of chloroform with an inert atmosphere of nitrogen, is added CMPD-006-007 (46 mg, 0.07 mmol, 2.0 equiv), 1-(3-Dimethylaminopropyl)-3-ethylcarbodiimide hydrochloride (10 mg, 0.052 mmol, 1.5 equiv) and 4-Dimethylaminopyridine (6.3 mg, 0.052 mmol, 1.5 equiv) in order at room temperature. The resulting solution is shaken at room temperature for 16 h in a shaking table. The mixture is filtered off and washed successively with water, tetrahydrofuran, dichloromethane.

Example 10: Solid Phase Synthesis of Oligonucleotide Using a Solid Support Loaded Nucleoside with Azidomethyl Linker 1. Solid Phase Synthesis to Elongate the Sequence:

Sequence info: 21mer

5'-mAfGmUfUJmAfUmUfCmAfGmGfAmAfG-mUfCmUJTfArmC-3'

The synthesis of above oligonucleotide sequence uses standard solid phase oligonucleotide synthesis with phosphoramidite chemistry using solid support loaded nucleoside with azidomethyl linker. The oligos synthesis is carried by a stepwise addition of nucleotide residues to the 5-terminus of the growing chain until the desired sequence is assembled. Each addition is referred to as a synthetic cycle Scheme A: Solid Phase Synthesis of Oligonucleotide using solid support loaded nucleoside with Azidomethyl linker

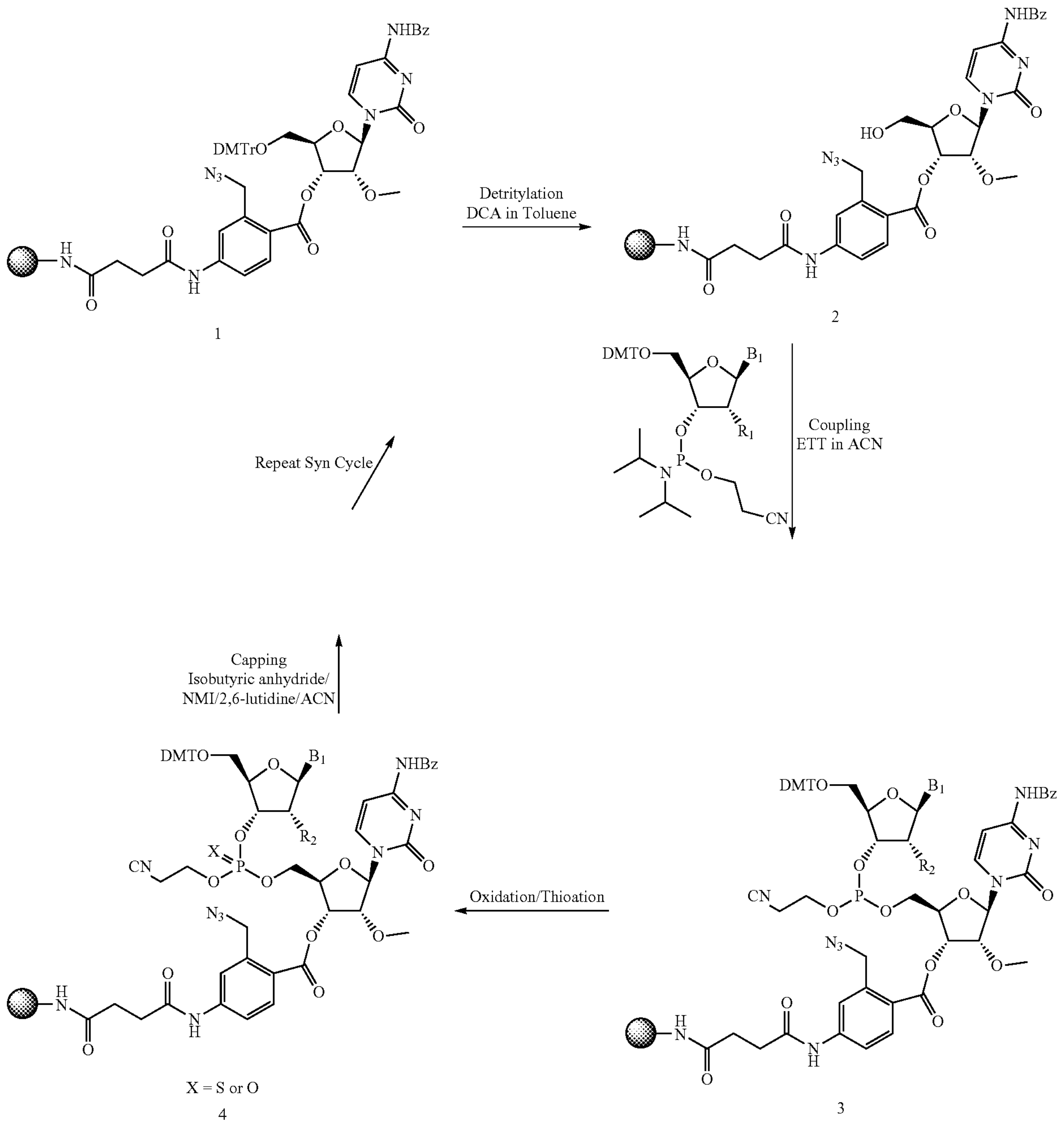

(Scheme A) and consists of four chemical reactions: 1) Detritylation 2) coupling, 3) Oxidation/Thioation, and 4) capping.

All amidites and all other synthesis reagents and solvents are obtained from commercially available sources and used as such. The chemicals and solvents for post-synthesis workflow are purchased from commercially available sources and used without any purification or treatment. Solvent (Acetonitrile) and solutions (amidite and activator) were stored over molecular sieves during synthesis.

The synthesis of the above sequence is performed at 1 um scale in ABI-394 synthesizer. The amidite solutions are prepared at 0.1M concentration and ethyl thio tetrazole (ETT) (0.5M in acetonitrile) is used as activator.

2. On Column Detritylation and Decyanoethylation (Trityl_Off)

Scheme B: on column detritylation and decyanoethylation

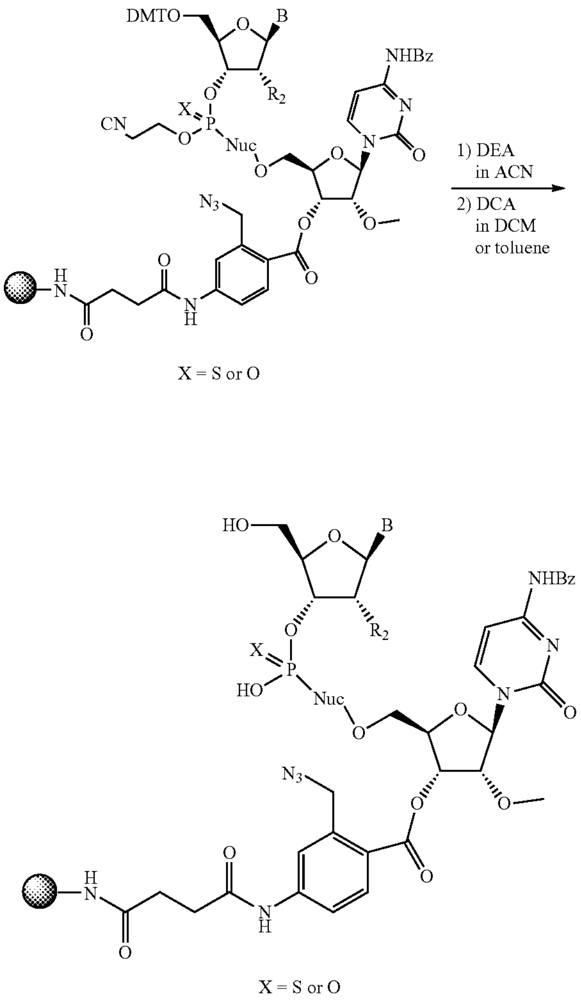

Once the full length of oligonucleotide synthesis completes, the final detriylation and decyanoethylation are performed on synthesizer with solid support attached (Scheme B);

3. Cleavage of Solid Support and Nucleobase Deprotection (Trityl_Off)

Scheme C: Solid support cleavage and nucleobase deprotection

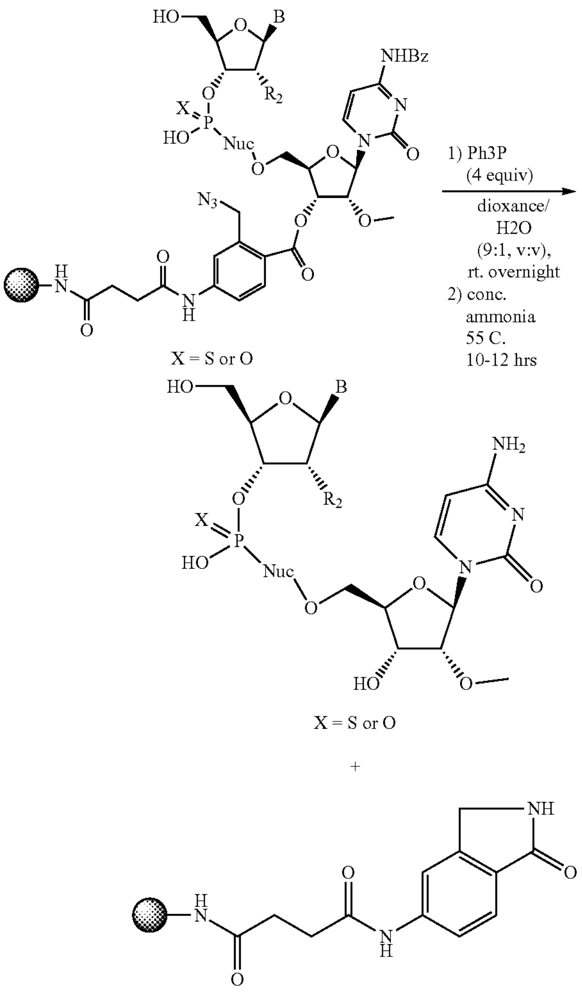

Then solid support loaded oligonucleotide is cleaved with Ph3P in dioxane/H2O (9:1, v/v), rt, overnight. After filtration to remove the solid support, the phosphate cyanoethyl ester and the nucleobases of the crude samples are deprotected using cone. ammonia solution at 55 C overnight.

The crude sequences are precipitated using acetone:ethanol (80:20) mix and the pellet are re-suspended in 0.02M sodium acetate buffer. Samples from each sequence are analyzed by LC-MS to confirm the identity, UV for quantification.

The crude sample then is purified on AKITA explorer purification system using source 15Q column. A column temperature of 65° C. is maintained during purification. Sample injection and collection is performed in an automatic sample collector. A single peak corresponding to the full length sequence is collected in the eluent. The purified sequence is desalted on a Sephadex G25 column using AKTA purifier. The desalted oligo sequence is analyzed for concentration (by UN measurement at A260) and identity and purity (by ion exchange HPLC or LCMS).

4. Cleavage of Solid Support and Nucleobase Deprotection (Trityl_on)

Scheme D: Solid support cleavage and deprotection (Trityl_on)

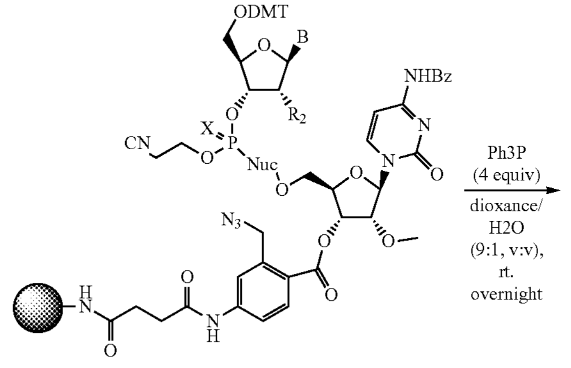

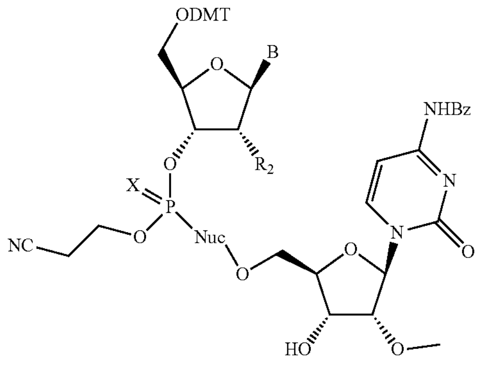

+

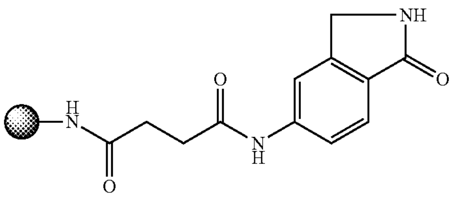

-continued

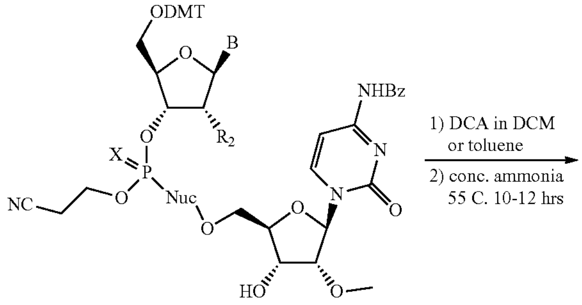

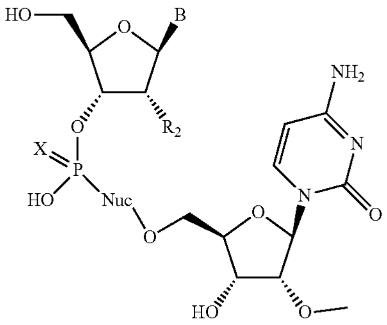

X = S or O

Then solid support loaded oligonucleotide is cleaved with Ph3P in dioxane/H2O (9:1, v/v), rt, overnight to provide fully protected oligo sequence. After filtration to remove the solid support, the nucleobases and cyanoethyl groups of the crude samples are deprotected using conc. ammonia solution at 55° C. overnight, followed by final detritlylation with 80% acetic acid at room temperature for one hour to provide fully deprotected oligo sequences (Scheme D).

The resulting crude product is separated and characterized as described above.

Synthesis of Trimer 5'-fUmUmC-3' on Solid Support (CMPD-A1)

Oligonucleotide with the above sequence 5'-fUmUmC-3' was synthesized by standard solid phase synthesis with phosphoramidite chemistry using solid support loaded 2'-OMe(Bz)C with 2-(azidomethyl)benzoyl linker. Synthesis was performed at 2 μmol scale on MM-12 synthesizer.

Cleavage of Trimer CMPD-A1 from Solid Support

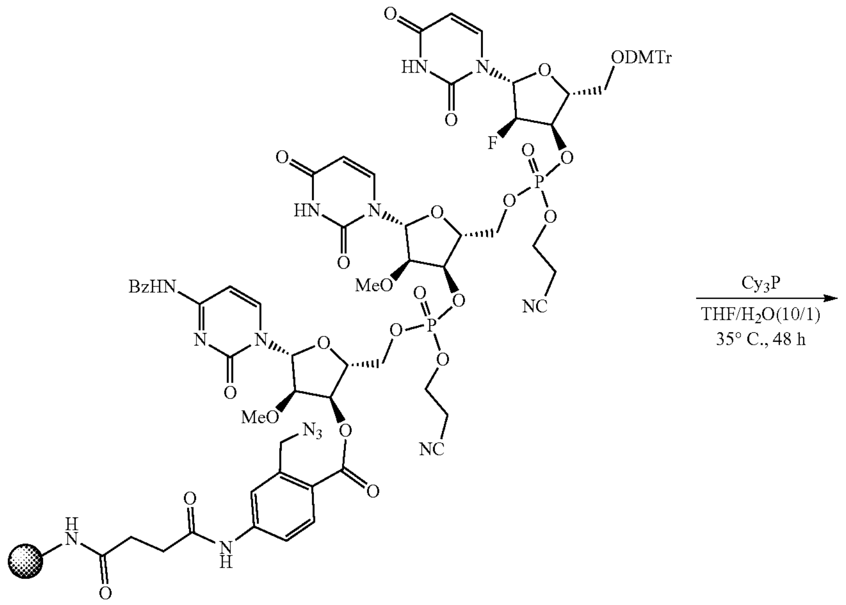

CMPD-A1

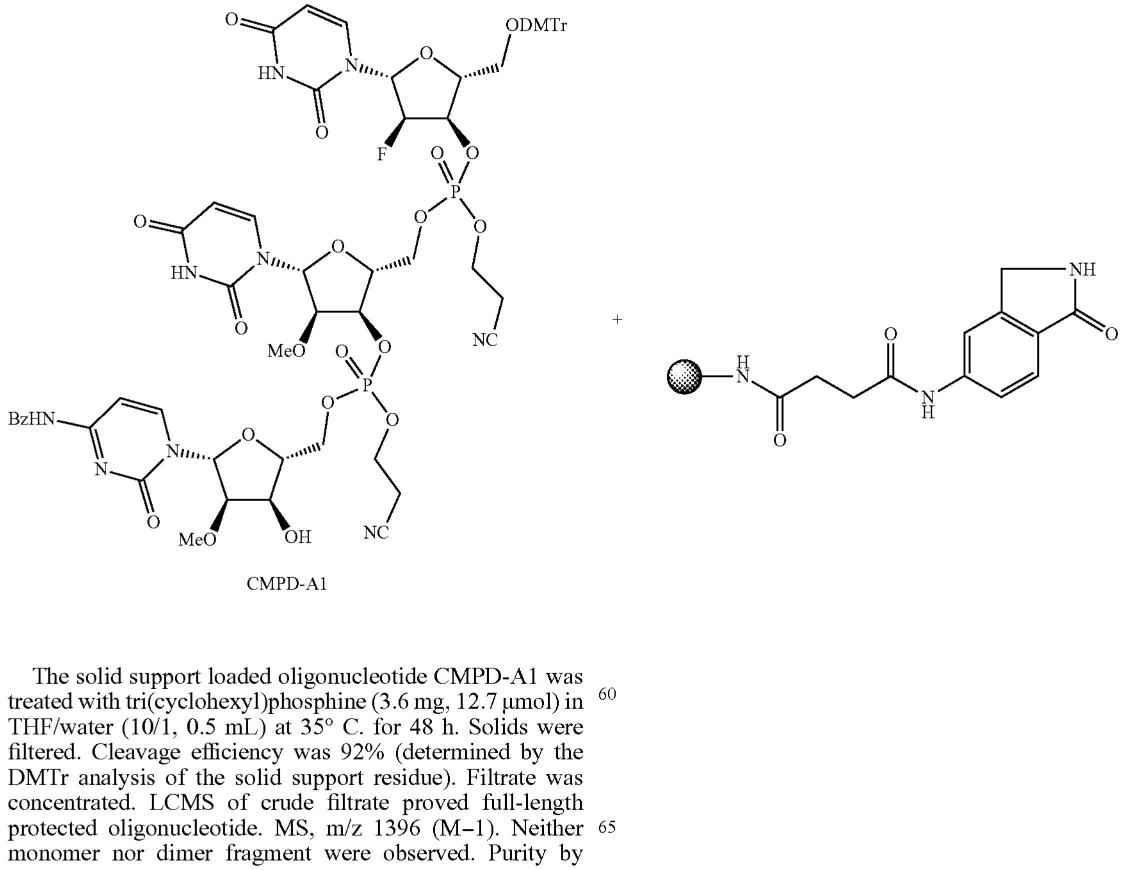

CMPD-A1

The solid support loaded oligonucleotide CMPD-A1 was treated with tri(cyclohexyl)phosphine (3.6 mg, 12.7 μmol) in THF/water (10/1, 0.5 mL) at 35° C. for 48 h. Solids were filtered. Cleavage efficiency was 92% (determined by the DMTr analysis of the solid support residue). Filtrate was concentrated. LCMS of crude filtrate proved full-length protected oligonucleotide. MS, m/z 1396 (M−1). Neither monomer nor dimer fragment were observed. Purity by LCMS: 45%.

Deprotection of CMPD-A2

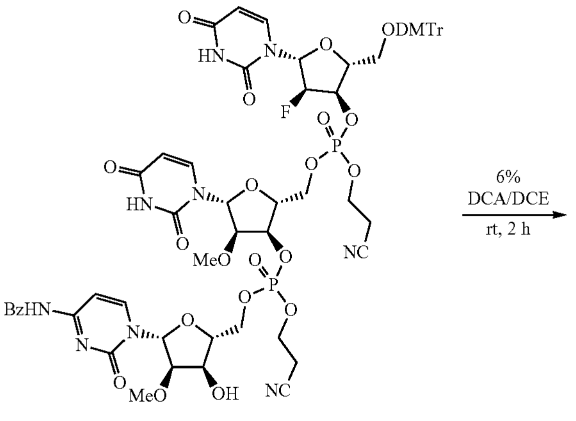

CMPD-A2

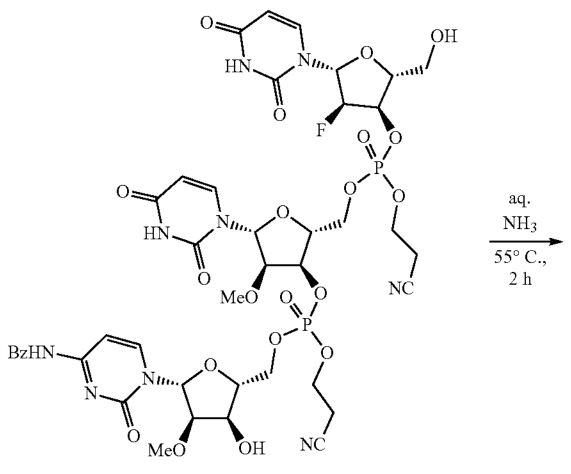

CMPD-A3

-continued

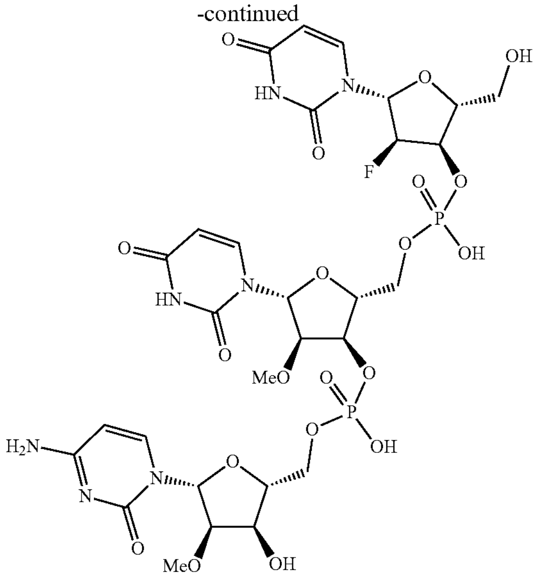

CMPD-A4

Crude evaporated residue CMPD-A2 from previous step was treated with 6% DCA in DCE at rt for 2 h. Starting material disappeared, 58% desired product CMPD-A3 by LCMS: m/z 1096 (M+1). Neither monomer nor dimer fragment were observed. Yield of CMPD-A3 (determined by DMTr analysis) was 93%. The reaction was quenched with TES and concentrated under reduced pressure.

Crude evaporated residue was treated with aq. $NH_3$ at 55° C. for 2 h to obtain fully deprotected trimer CMPD-A4. Neither monomer nor dimer fragment were observed. The reaction mixture was concentrated under reduced pressure. The crude residue was dissolved in water, adjusted to pH-3 with 0.5M aq. HCl at 3° C. and extracted four times with $Et_2O$ at 3° C. to remove DMTr and benzoic acid. The yield of CMPD-A4 was 91% (determined by measuring absorption of aqueous layer by UV spectroscopy at 260 nm), purity 65% (by LCMS). MS, m/z 884 (M−1).

Synthesis of Tetramer 5'-mAmGmUmC-3' on Solid Support (CMPD-A5)

Oligonucleotide with the above sequence was synthesized by standard solid phase synthesis with phosphoramidite chemistry using solid support loaded 2'-OMe(Bz)C with 2-(azidomethyl)benzoyl linker. Synthesis was performed at 2 µmol scale on MM-12 synthesizer.

Cleavage of Tetramer CMPD-A5 from Solid Support

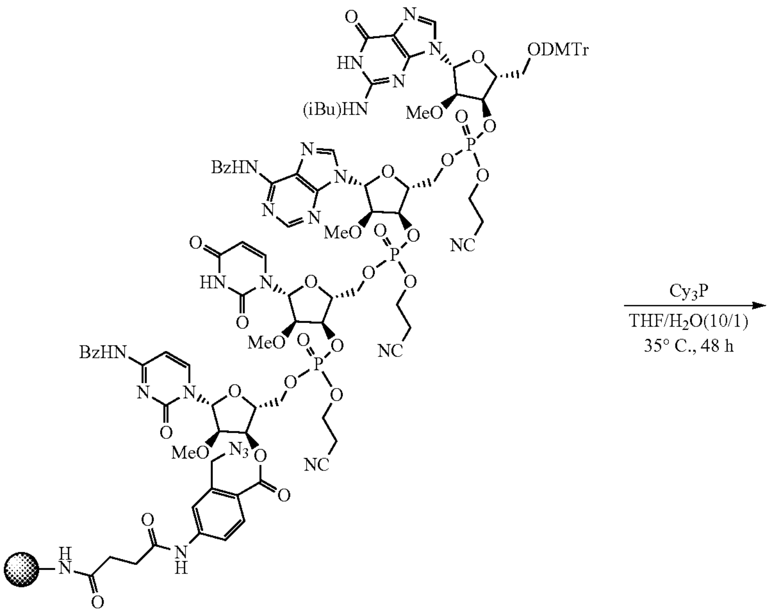

CMPD-A5

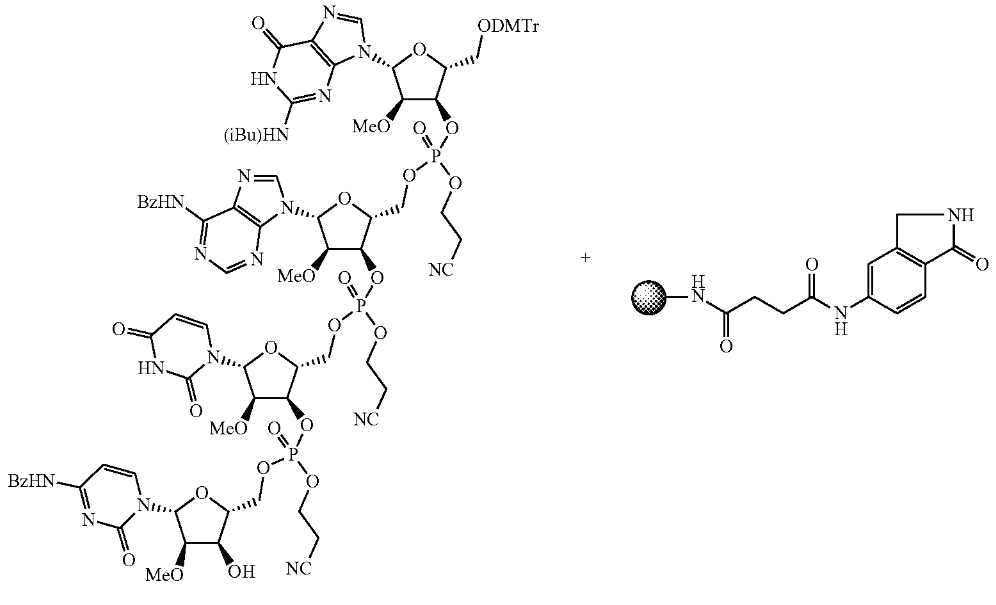

CMPD-A6

The solid support loaded oligonucleotide CMPD-A5 was treated with tri(cyclohexyl)phosphine (3 mg, 10 μmol) in THF/water (10/1, 0.5 mL) at 35° C. for 48 h. Solids were filtered. Cleavage efficiency was 91% (determined by the DMTr analysis of the solid support residue). Filtrate was concentrated. LCMS of crude filtrate proved full-length protected oligonucleotide CMPD-A6. MS, m/z 1011 (M/2+1), purity 46%. No monomer, dimer and trimer fragments were observed.

Deprotection of CMPD-A6

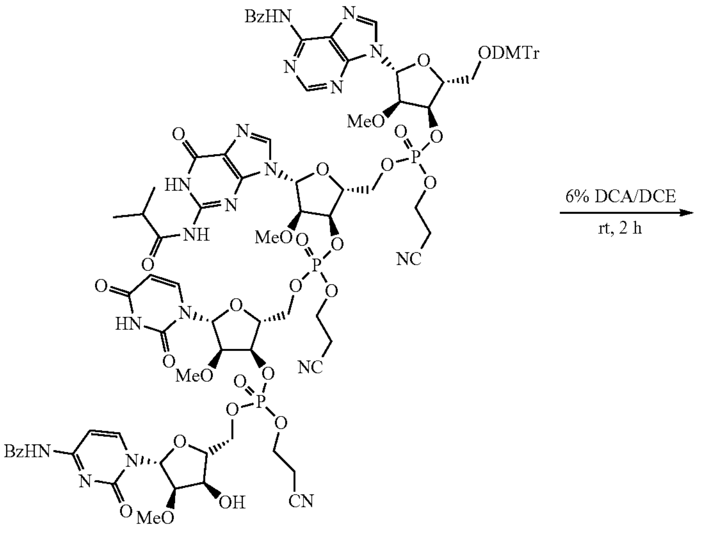

CMPD-A6

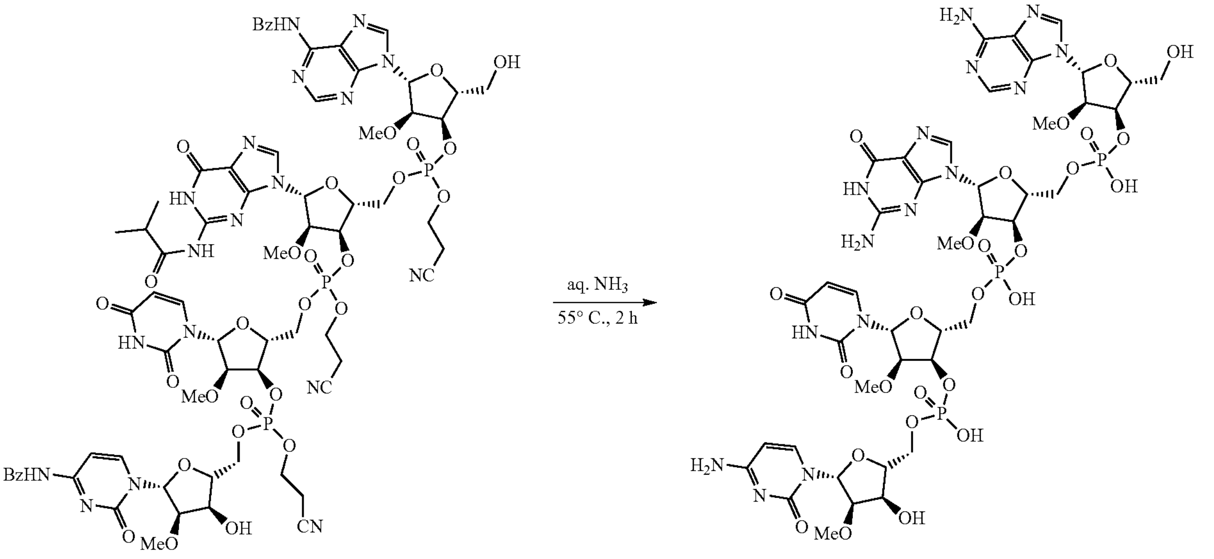

CMPD-A7

CMPD-A8

Crude evaporated residue CMPD-A6 from previous step was treated with 6% DCA in DCE at rt for 2 h. Starting material disappeared, 45% desired product signal for CMPD-A7 by LCMS; MS, m/z 1717 (M+1). No monomer, dimer or trimer fragments were observed. Yield of CMPD-A7 was 92% (determined by the DMTr analysis). The reaction was quenched with TES and concentrated under reduced pressure.

Crude evaporated residue was treated with aq. $NH_3$ at 55° C. for 2 h to obtain fully deprotected tetramer CMPD-A8. No monomer, dimer and trimer fragments were observed. The reaction mixture was concentrated under vacuum. The crude residue was dissolved in water, adjusted to pH-3 with 0.5M HCl aqueous at 3° C. and extracted four times with $Et_2O$ at 3° C. to remove DMTr and benzoic acid. Yield of CMPD-A8 was 81% (determined by measuring absorption of aqueous layer by UV spectroscopy at 260 nm) purity 60% (by LCMS). MS, m/z 1278 (M−1).

EQUIVALENTS

The present disclosure is not to be limited in terms of the particular embodiments described in this application, which are intended as single illustrations of individual aspects of the present disclosure. Many modifications and variations of this present disclosure can be made without departing from its spirit and scope, as will be apparent to those skilled in the art. Functionally equivalent methods and apparatuses within the scope of the present disclosure, in addition to those enumerated herein, will be apparent to those skilled in the art from the foregoing descriptions. Such modifications and variations are intended to fall within the scope of the present disclosure. It is to be understood that this present disclosure is not limited to particular methods, reagents, compounds compositions, or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as “up to,” “at least,” “greater than,” “less than,” and the like, include the number recited and refer to ranges which can be subsequently broken down into subranges as discussed above. Finally, as will be understood by one skilled in the art, a range includes each individual member. Thus, for example, a group having 1-3 items refers to groups having 1, 2, or 3 items. Similarly, a group having 1-5 items refers to groups having 1, 2, 3, 4, or 5 items, and so forth.

All patents, patent applications, provisional applications, and publications referred to or cited herein are incorporated by reference in their entirety, including all figures and tables, to the extent they are not inconsistent with the explicit teachings of this specification.

What is claimed is:

1. A compound having the structure of Formula (I-A) or (II-A)

(I-A)

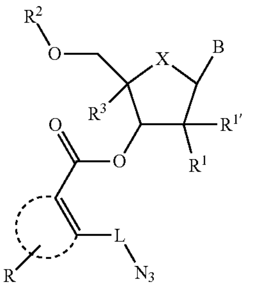

(II-A)

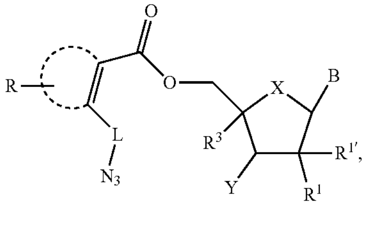

or a salt thereof, wherein

X is selected from the group consisting of —O—, —S—, —NR''— and —C(R')$_2$—;

Y is selected from the group consisting of —OR'', —OPG, —NHPG, and —NHR';

B is an optionally protected natural or unnatural nucleobase;

L is an optionally substituted $C_{1-4}$ alkyl;

the dashed curve

represents an aryl moiety;

R is a support moiety attached to the aryl moiety through one or more linkers;

$R^1$ is selected from the group consisting of —OPG, F, —OR'', and —O(CR'$_2$)$_{1-2}$OCR'$_3$;

$R^{1'}$ is selected from the group consisting of H, OPG, F, —OR'', and —O(CR'$_2$)$_{1-2}$OCR'$_3$;

$R^2$ is selected from the group consisting of a $C_{2-12}$alkyl, a $C_{1-12}$haloalkyl, PG, an optionally protected nucleotide, a prodrug moiety, and an optionally protected oligonucleotide;

$R^3$ is selected from the group consisting of H, —OPG, F, and —OR'', or $R^1$ and $R^3$ together form an optionally substituted 2 to 4 atom bridge;

each R' is independently selected from the group consisting of H, F, aryl, a $C_{1-12}$alkyl, and a $C_{1-12}$haloalkyl;

each R'' is independently selected from the group consisting of aryl, a $C_{1-12}$alkyl, and a $C_{1-12}$haloalkyl; and each PG is independently selected from the group consisting of 2,2,2-trichloroethyl carbonate (Troc), 2-methoxyethoxymethyl ether (MEM), 2-naphthylmethyl ether (Nap), 4-methoxybenzyl ether (PMB), acetate (Ac), benzoate (Bz), benzyl ether (Bn), benzyloxymethyl acetal (BOM), methoxymethyl acetal (MOM), methoxypropyl acetal (MOP), methyl ether, and tetrahydropyranyl acetal (THP).

2. The compound of claim 1, wherein L has the structure of

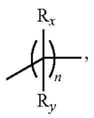

wherein Rx and Ry are each independently selected from the group consisting of H, Me, Et, Pr, and Bu, or wherein Rx and Ry together form a 4 to 6-membered ring; and wherein n is an integer between 1 and 4.

3. The compound of claim 1, wherein L is methylene or ethylene.

4. The compound of claim 1, wherein the compound is represented by Formula (Ia) or (IIa)

(Ia)

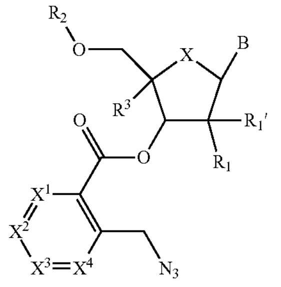

-continued (IIa)

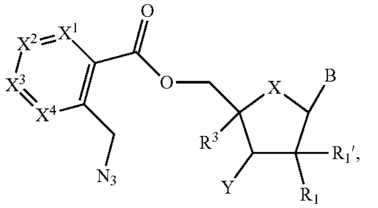

wherein $X^1$, $X^2$, $X^3$, and $X^4$ are each independently selected from the group consisting of —CR—, —$CR^4$—, and —N—, wherein at least one of $X^1$, $X^2$, $X^3$, and $X^4$ is —CR—, and optionally wherein any two adjacent $X^1$, $X^2$, $X^3$, and $X^4$ are linked together to form an optionally substituted ring;

R is a support moiety attached through one or more linkers; and each $R^4$ is independently selected from the group consisting of H, alkyl, alkoxyl, aryl, halogen, $NO_2$, and substituted carbonyl.

5. The compound of claim 1, wherein X is O; $R^1$ is F or OR"; and $R^{1'}$ is H.

6. The compound of claim 1, wherein R is a solid support moiety or a soluble support moiety attached through one or more linkers to the aryl moiety.

7. The compound of claim 1, wherein R is represented by:

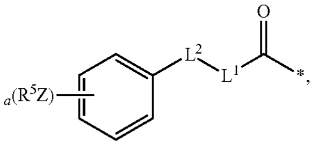 or

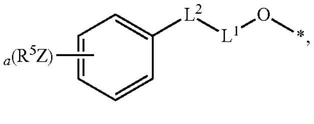

wherein $L^1$ is selected from the group consisting of a bond, an optionally substituted $C_{1-6}$alkylene group, an optionally substituted $C_{2-6}$alkenylene group, an optionally substituted$C_{2-6}$ alkynylene group, an optionally substituted $C_{3-8}$cycloalkyl group, an optionally substituted $C_{6-10}$aryl group, an optionally substituted 5-10 membered heteroaryl group, and an optionally substituted 4 to 8 membered heterocyclic group;

$L^2$ is selected from the group consisting of a single bond, —O—, —N(R')—, and —C(O)—;

each Z is independently selected from the group consisting of —O—, —N(R")—, and a bond;

each $R^5$ is independently selected from the group consisting of an alkyl group, an alkenyl group, an alkynyl group, and an ethylene glycol group;

a is an integer of 1 to 3; and

* represents the point of attachment to the aryl moiety.

8. The compound of claim 7, wherein $L^1$ is a saturated 4 to 8 membered heterocyclic group;

or $L^2$ is —C(O)—; or a is 3, Z is O, and $R^5$ is a $C_{10-40}$alkyl group.

9. The compound of claim 1, wherein R is represented by

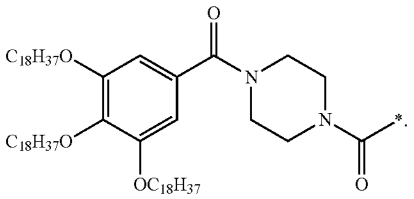

wherein * represents the point of attachment to the aryl moiety.

10. The compound of claim 1, wherein the compound is represented by the following Formula (Ib):

(Ib)

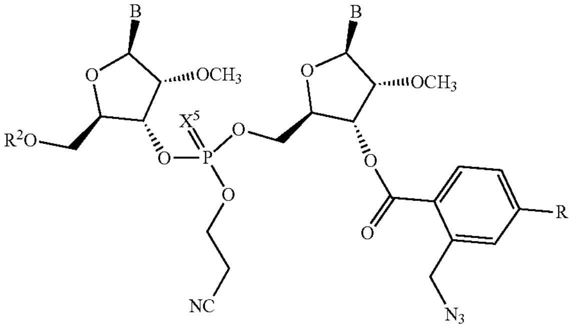

wherein $X^5$ is absent, O, or S;

the compound is represented by the following Formula (Ic):

(Ic)

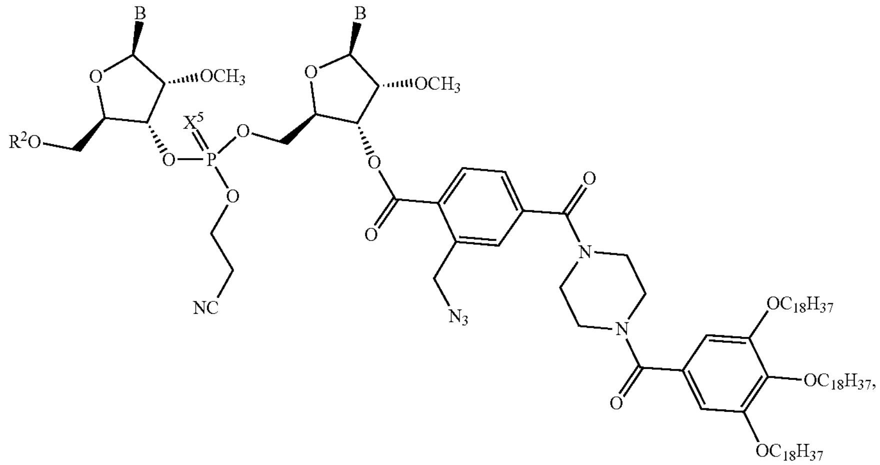

wherein $X^5$ is absent, O, or S; or the compound is represented by the following Formula (If):

(If)

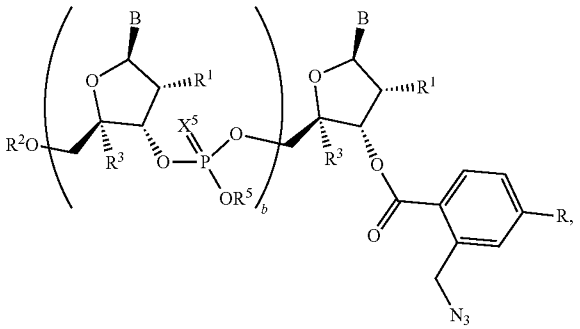

wherein $X^5$ is absent, O, or S;

$R^2$ is PG;

$R^5$ is selected from the group consisting of a counterion, methyl, and 2-cyanoethyl; and b is an integer of 1 to 30.

11. A method of selectively conjugating an oligomer having protected nucleobases at its 3'-position, wherein the oligomer having protected nucleobases is represented by Formula (I-A) or (II A), (I-A)

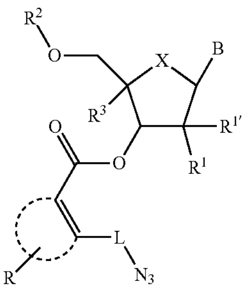

-continued (II-A)

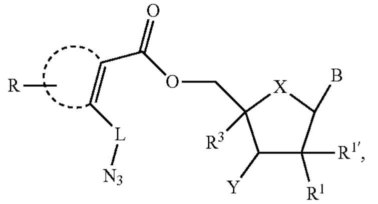

or a salt thereof, wherein

X is selected from the group consisting of —O—, —S—, —NR"—, and —C(R')$_2$—;

B is a protected natural or unnatural nucleobase;

$R^1$ is selected from the group consisting of —OPG, F, —OR", and —O(CR'$_2$)$_{1-2}$OCR'$_3$;

$R^{1'}$ is selected from the group consisting of H, —OPG, F, —OR", and —O(CR'$_2$)$_{1-2}$OCR'$_3$;

$R^2$ is an oligonucleotide that is protected at the 5'-position, the oligonucleotide comprising protected natural or unnatural nucleobases;

$R^3$ is selected from the group consisting of H, —OPG, F, and —OR", or $R^1$ and $R^3$ together form an optionally substituted 2-4 atom bridge;

each R' is independently selected from the group consisting of H, F, aryl, a $C_{1-12}$alkyl, and a $C_{1-12}$haloalkyl;

each R" is independently selected from the group consisting of H, aryl, a $C_{1-12}$alkyl, and a $C_{1-12}$haloalkyl;

each PG is independently selected from the group consisting of 2,2,2-trichloroethyl carbonate (Troc), 2-methoxyethoxymethyl ether (MEM), 2-naphthylmethyl ether (Nap), 4-methoxybenzyl ether (PMB), acetate (Ac), benzoate (Bz), benzyl ether (Bn), benzyloxymethyl acetal (BOM), methoxymethyl acetal (MOM), methoxypropyl acetal (MOP), methyl ether, and tetrahydropyranyl acetal (THP);

L is $C_{1-4}$alkyl;

the dashed curve

represents an aryl moiety; and

R is a support moiety attached through one or more linkers to the aryl moiety, the method comprising the steps of:

(a) reacting the oligomer having protected nucleobases represented by Formula (I-A) with a phosphine reagent to form a compound of Formula (III)

(III)

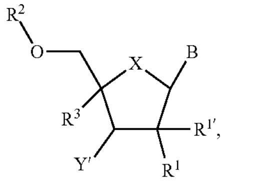

wherein B is a protected natural or unnatural nucleobase, and wherein Y' is —OH, and (b) reacting Y' of Formula (III) with a monomer or a second oligomer to form a covalent bond between the 3'-position of Formula (III) and the monomer or second oligomer, thereby selectively conjugating the oligomer having protected nucleobases represented by Formula (I-A) at its 3'-position.

12. The method of claim 11, wherein the compound of Formula (I-A) is represented by the following Formula (If):

(If)

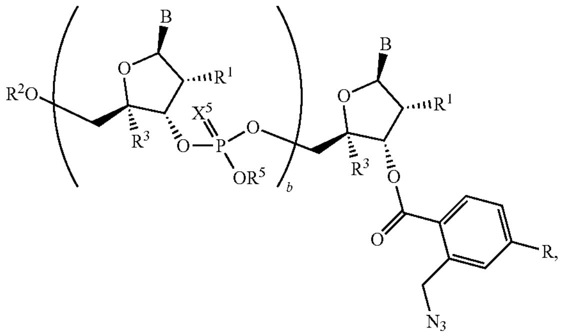

wherein $X^5$ is O or S;

$R^2$ is PG;

$R^5$ is selected from the group consisting of a counterion, methyl and 2-cyanoethyl; and b is an integer of 1 to 30.

13. The method of claim 11, wherein step (b) further comprises attaching the compound of Formula (III) at its 3'-position to a protecting group, followed by deprotecting the compound of Formula (III) at its 5'-position and reacting the resulting deprotected compound of Formula (III) at its 5'-position to form a covalent bond with a third nucleotide or an oligonucleotide, thereby conjugating the oligomer having protected nucleobases represented by Formula (I-A) at both its 3'- and 5'-positions.

14. The method of claim 11, further comprising a step of deprotecting the protected natural or unnatural nucleobases.

15. A compound of one of the following formulae:

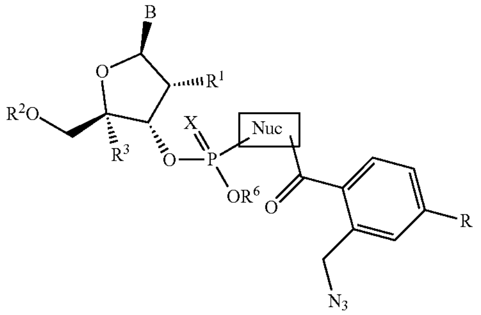

or

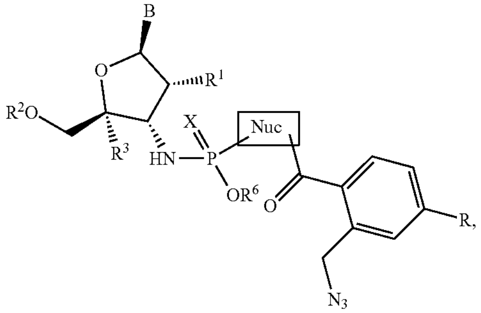

wherein

Nuc is an oligonucleotide subunit having 1 to 30 linked nucleosides;

B is a protected natural or unnatural nucleobase;

X is absent, O or S;

$R^1$ is selected from the group consisting of —OPG, F, —OR", and $—O(CR'_2)_{1-2}OCR'_3$;

$R^2$ is PG;

$R^3$ is selected from the group consisting of H, —OPG, F, and —OR", or $R^1$ and $R^3$ together form an optionally substituted 2 to 4 atom bridge;

each R' is independently selected from the group consisting of H, F, aryl, a $C_{1-12}$alkyl, and a $C_{1-12}$haloalkyl;

each R" is independently selected from the group consisting of H, aryl, a $C_{1-12}$alkyl, and a $C_{1-12}$haloalkyl;

each PG is independently selected from the group consisting of 2,2,2-trichloroethyl carbonate (Troc), 2-methoxyethoxymethyl ether (MEM), 2-naphthylmethyl ether (Nap), 4-methoxybenzyl ether (PMB), acetate (Ac), benzoate (Bz), benzyl ether (Bn), benzyloxymethyl acetal (BOM), methoxymethyl acetal (MOM), methoxypropyl acetal (MOP), methyl ether, and tetrahydropyranyl acetal (THP);

$R^6$ is selected from the group consisting of a counterion, methyl, and 2-cyanoethyl; and R is a solid support or a soluble support moiety attached through one or more linkers.

16. The method of claim 11, wherein the phosphine reagent is tri(cyclohexyl)phosphine or triphenylphosphine.

* * * * *